(12) United States Patent
Gould

(10) Patent No.: US 11,227,674 B2
(45) Date of Patent: Jan. 18, 2022

(54) HOME AUTOMATION SYSTEM GENERATING USER HEALTH SCORE AND RELATED METHODS

(71) Applicant: K4CONNECT INC., Raleigh, NC (US)

(72) Inventor: Jonathan Andrew Gould, Raleigh, NC (US)

(73) Assignee: K4CONNECT INC., Raleigh, NC (US)

( * ) Notice: Subject to any disclaimer, the term of this patent is extended or adjusted under 35 U.S.C. 154(b) by 724 days.

(21) Appl. No.: 15/196,803

(22) Filed: Jun. 29, 2016

(65) Prior Publication Data

US 2017/0004286 A1   Jan. 5, 2017

Related U.S. Application Data

(60) Provisional application No. 62/186,466, filed on Jun. 30, 2015, provisional application No. 62/186,480, (Continued)

(51) Int. Cl.
  *G16H 10/60* (2018.01)
  *G16H 40/63* (2018.01)
  (Continued)

(52) U.S. Cl.
  CPC ............ *G16H 10/60* (2018.01); *G05B 15/00* (2013.01); *G05D 23/1931* (2013.01); (Continued)

(58) Field of Classification Search
  CPC ..... G16H 50/30; H04L 12/2803; A61B 5/002; A61B 2503/08; G08B 21/0484–0492
  See application file for complete search history.

(56) References Cited

U.S. PATENT DOCUMENTS

| 7,379,778 B2 | 5/2008 | Hayes et al. |
| 7,574,693 B1 | 8/2009 | Kemink |

(Continued)

FOREIGN PATENT DOCUMENTS

WO   2000043900 A1   7/2000

OTHER PUBLICATIONS

Rajeev Piyare and Seong Ro Lee, Smart Home-Control and Monitoring System Using Smart Phone, 2013, The 1st International Conference on Convergence and Its Application, ASTL vol. 24, pp. 83-86 (Year: 2013).*

(Continued)

*Primary Examiner* — Janice A Mooneyham
*Assistant Examiner* — Karen A Hranek
(74) *Attorney, Agent, or Firm* — Allen, Dyer, Doppelt + Gilchrist, P.A.

(57) ABSTRACT

A home automation (HA) system may include addressable HA devices and a user interface device configured to permit user social networking and generate user social networking data based thereon. The HA system may also include a controller and a memory coupled thereto and configured to store measured user health data and determine user physical activity data based upon the addressable HA devices. The controller and the memory may be configured to generate a user health score based upon the user social networking data, user health data, and user physical activity data and communicate the user health score via the cloud.

13 Claims, 39 Drawing Sheets

Related U.S. Application Data filed on Jun. 30, 2015, provisional application No. 62/186,487, filed on Jun. 30, 2015, provisional application No. 62/186,491, filed on Jun. 30, 2015, provisional application No. 62/186,501, filed on Jun. 30, 2015, provisional application No. 62/186,506, filed on Jun. 30, 2015, provisional application No. 62/186,473, filed on Jun. 30, 2015, provisional application No. 62/186,469, filed on Jun. 30, 2015.

(51) Int. Cl.

| | |
|---|---|
| *G16H 50/30* | (2018.01) |
| *G16H 40/67* | (2018.01) |
| *G05D 23/19* | (2006.01) |
| *G05B 15/00* | (2006.01) |
| *H04L 12/28* | (2006.01) |
| *H04W 4/80* | (2018.01) |
| *G06Q 50/00* | (2012.01) |
| *H04L 12/26* | (2006.01) |
| *H04L 29/06* | (2006.01) |
| *G16H 20/40* | (2018.01) |
| *H04L 29/12* | (2006.01) |
| *H04L 29/08* | (2006.01) |
| *H04L 29/14* | (2006.01) |
| *F24F 11/30* | (2018.01) |
| *F24F 110/12* | (2018.01) |
| *F24F 11/62* | (2018.01) |
| *F24F 11/58* | (2018.01) |

(52) U.S. Cl.
CPC ............. *G06Q 50/01* (2013.01); *G16H 20/40* (2018.01); *G16H 40/63* (2018.01); *G16H 40/67* (2018.01); *G16H 50/30* (2018.01); *H04L 12/281* (2013.01); *H04L 12/2803* (2013.01); *H04L 12/2809* (2013.01); *H04L 12/2816* (2013.01); *H04L 12/2818* (2013.01); *H04L 12/2821* (2013.01); *H04L 12/2825* (2013.01); *H04L 12/2834* (2013.01); *H04L 12/2836* (2013.01); *H04L 43/0811* (2013.01); *H04L 61/103* (2013.01); *H04L 61/6022* (2013.01); *H04L 61/6081* (2013.01); *H04L 67/025* (2013.01); *H04L 67/10* (2013.01); *H04L 67/12* (2013.01); *H04L 67/16* (2013.01); *H04L 67/22* (2013.01); *H04L 67/303* (2013.01); *H04L 69/08* (2013.01); *H04L 69/40* (2013.01); *H04W 4/80* (2018.02); *F24F 11/30* (2018.01); *F24F 11/58* (2018.01); *F24F 11/62* (2018.01); *F24F 2110/12* (2018.01); *H04L 2012/2841* (2013.01)

(56) References Cited

U.S. PATENT DOCUMENTS

| | | | |
|---|---|---|---|
| 8,640,038 B1 | | 1/2014 | Reeser et al. |
| 8,937,930 B2 * | | 1/2015 | Sprigg ................. G06F 9/4411 370/338 |
| 9,875,450 B1 * | | 1/2018 | Hendrick, III ...... G06Q 10/0631 |
| 2004/0039459 A1 | | 2/2004 | Daugherty et al. |
| 2004/0163073 A1 | | 8/2004 | Krzyzanowski et al. |
| 2005/0278409 A1 * | 12/2005 | Kutzik ................. G16H 20/70 709/200 |
| 2006/0022999 A1 | 2/2006 | Lee et al. |
| 2007/0152837 A1 * | 7/2007 | Bischoff ............... G16H 40/67 340/573.1 |
| 2008/0001735 A1 * | 1/2008 | Tran ..................... A61B 5/0488 340/539.22 |
| 2008/0117060 A1 * | 5/2008 | Cuddihy .............. A61B 5/1118 340/573.1 |
| 2008/0203943 A1 | 8/2008 | Baaijens et al. |
| 2009/0221890 A1 * | 9/2009 | Saffer ................ A61B 5/14532 600/347 |
| 2010/0138007 A1 | 6/2010 | Clark et al. |
| 2011/0140832 A1 | 6/2011 | Vinkenvleugel et al. |
| 2012/0169482 A1 | 7/2012 | Chen et al. |
| 2013/0073303 A1 * | 3/2013 | Hsu ..................... H04L 12/2823 705/2 |
| 2013/0191755 A1 | 7/2013 | Balog et al. |
| 2013/0217979 A1 * | 8/2013 | Blackadar ........... A61B 5/0024 600/301 |
| 2013/0262357 A1 * | 10/2013 | Amarasingham ...... G16H 50/30 706/21 |
| 2013/0272223 A1 * | 10/2013 | Mathews ................ H04W 4/70 370/329 |
| 2013/0328946 A1 | 12/2013 | Zenker |
| 2014/0181704 A1 | 6/2014 | Madonna et al. |
| 2014/0333437 A1 * | 11/2014 | Hong ................. G08B 21/0484 340/573.1 |
| 2015/0089038 A1 | 3/2015 | Gayles et al. |
| 2016/0019360 A1 * | 1/2016 | Pahwa ................... G06Q 50/01 705/3 |
| 2016/0070244 A1 | 3/2016 | Cipollo et al. |
| 2016/0132031 A1 * | 5/2016 | Kozura ............... H04L 12/2816 700/275 |
| 2016/0248598 A1 * | 8/2016 | Lin ..................... H04L 12/2803 |
| 2016/0314255 A1 * | 10/2016 | Cook .................... G16H 40/67 |
| 2017/0024538 A1 * | 1/2017 | Siddiqui ............... G06Q 50/22 |

OTHER PUBLICATIONS

Mobile device, May 25, 2015, Wikipedia (Year: 2015).*
Wilson et al., Using Many Simple Sensors for Automatic Monitoring in the Home, 2008, Carnegie Mellon University Robotics Institute (Year: 2008).*
Roston, HIRIS 'wearable computer': home automation control on your wrist, Jan. 22, 2015, Slashgear.com (Year: 2015).*
Moorhead, The Problem With Home Automation's Internet of Things (IoT), Sep. 26, 2013, Forbes (Year: 2013).*
Tunca et al., Multimodal Wireless Sensor Network-Based Ambient Assisted Living in Real Homes with Multiple Residents, May 24, 2014, Sensors 14, 9692-9719 (Year: 2014).*
Ni et al., The Elderly's Independent Living in Smart Homes: A Characterization of Activities and Sensing Infrastructure Survey to Facilitate Services Development, May 14, 2015, Sensors 15, 111312-11362 (Year: 2015).*
Patrick Moorhead, The Problem With Home Automation's Internet of Things (IoT), Forbes, Sep. 26, 2013.
Gould et al., U.S. Appl. No. 15/196,654, filed Jun. 29, 2016.
Gould et al., U.S. Appl. No. 15/196,365, filed Jun. 29, 2016.
Gould, U.S. Appl. No. 15/196,544, filed Jun. 29, 2016.
Gould et al., U.S. Appl. No. 15/196,900, filed Jun. 29, 2016.
Gould et al., U.S. Appl. No. 15/196,337, filed Jun. 29, 2016.
Gould et al., U.S. Appl. No. 15/196,720, filed Jun. 29, 2016.
Gould, U.S. Appl. No. 15/196,990, filed Jun. 29, 2016.

* cited by examiner

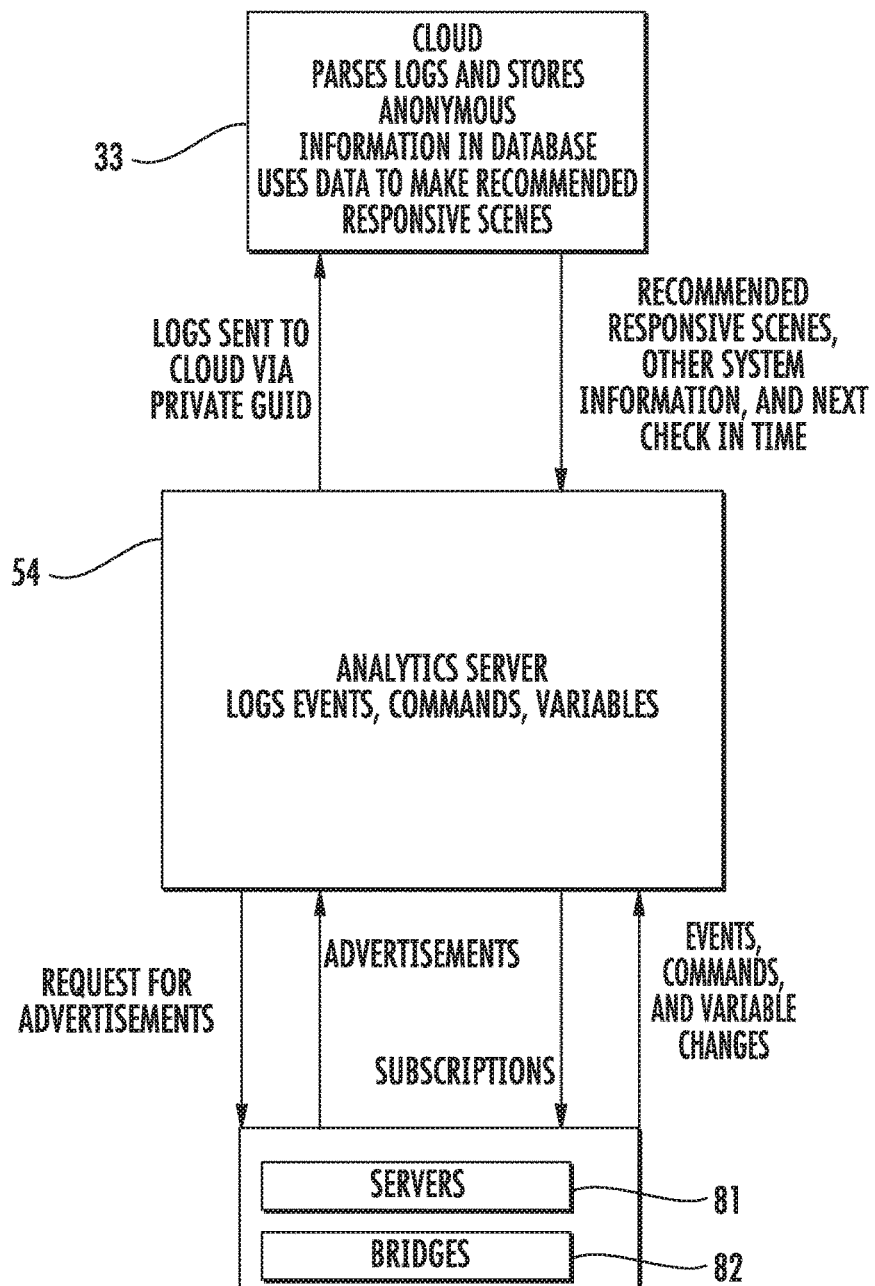

61 — CAMERA SERVER
(e.g., EXECUTED BY HOME DEVICE AND/OR K4HUB)

- LOCATES CAMERA IMAGES/VIDEO AND STREAMS THE IMAGES/VIDEO TO THE SYSTEM
- ACTS AS AN IMAGE PROXY FOR REMOTE USERS NOT ABLE TO DIRECTLY CONNECT TO THE CAMERA

*FIG. 5*

62 — CONFIGURATION SERVER
(e.g., EXECUTED BY HOME DEVICE AND/OR K4HUB)

- STORES THE PERSISTENT CONFIGURATION OF THE HOME AUTOMATION INTEGRATION SYSTEM
- USES THE DEVICE DESCRIPTIONS DURING THE DEVICE CONNECTION PROCESS TO SETUP DEVICES ON THE SYSTEM IN TANDEM WITH A DEVICE SETUP WIZARD

*FIG. 6*

63 — DEBUG SERVER
(e.g., EXECUTED BY HOME DEVICE AND/OR K4HUB)

- ENABLE BRIDGE DEBUGGING

*FIG. 7*

66 — NOTIFICATION SERVER
(e.g., EXECUTED BY HOME DEVICE AND/OR K4HUB)
- SENDS NOTIFICATION FROM THE SYSTEM TO THE REMOTE DEVICE

*FIG. 9*

64 — LOADER SERVER
(e.g., EXECUTED BY HOME DEVICE AND/OR K4HUB)
- LOADS BRIDGES AND SERVERS

*FIG. 10*

67 — STATUS SERVER
(e.g., EXECUTED BY HOME DEVICE AND/OR K4HUB)
- SERVES AS A SYSTEM WIDE STATE MACHINE STORING A LOG OF LAST KNOWN STATE WITHOUT HAVING TO POLL DEVICES IN THE SYSTEM (e.g., BY HAVING PERFORMING AS A STANDALONE STATE MACHINE TRACKING THE LAST KNOWN STATES OF THE SYSTEM)

*FIG. 11*

68 — WEB SERVER
(e.g., EXECUTED BY HOME DEVICE AND/OR K4HUB)
- EXECUTES WEB INTERFACE

*FIG. 12*

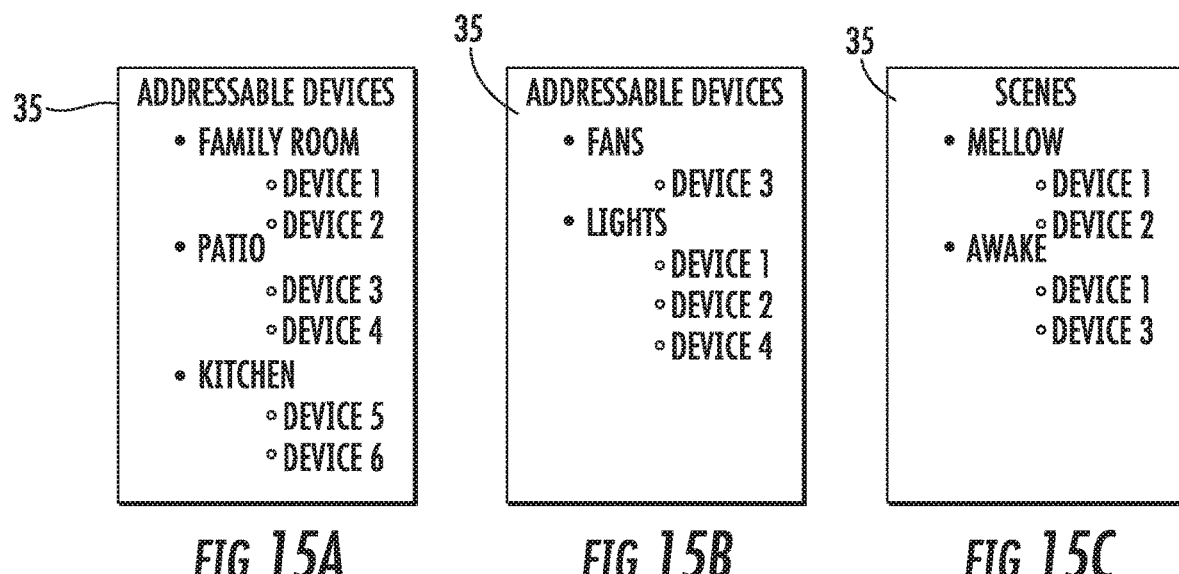

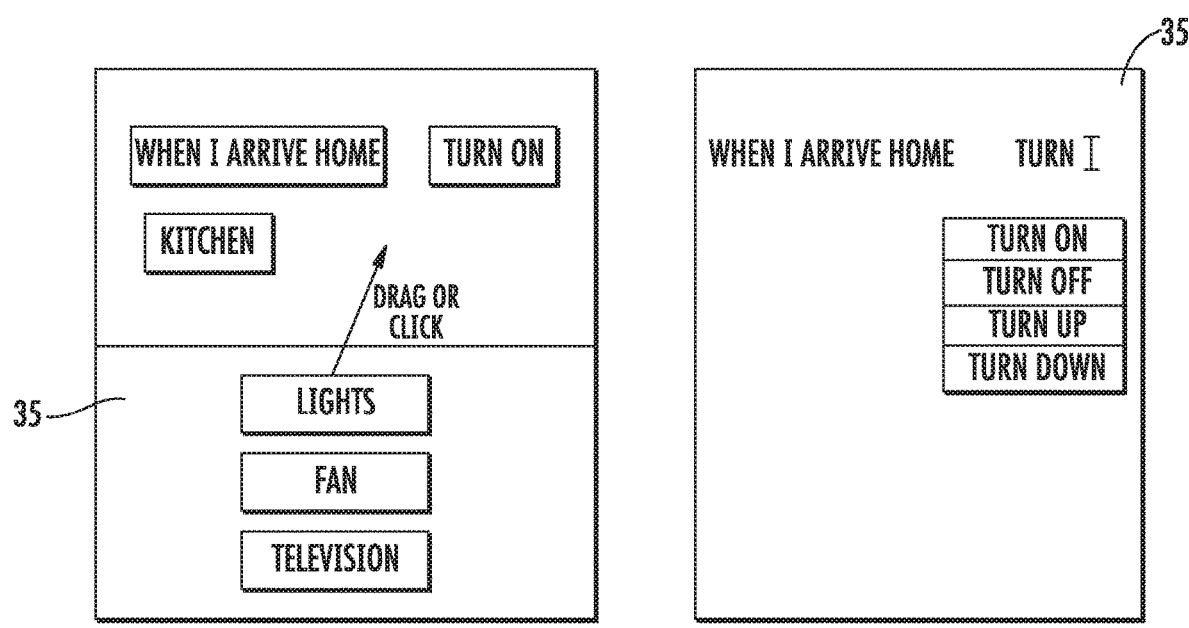

HOME AUTOMATION SYSTEM GENERATING USER HEALTH SCORE AND RELATED METHODS

RELATED APPLICATIONS

The present application claims the priority benefit of provisional application Ser. Nos. 62/186,466, 62/186,480, 62/186,487, 62/186,491, 62/186,501, 62/186,506, 62/186,473 and 62/186,469 all filed on Jun. 30, 2015, the entire contents of all of which are herein incorporated in their entirety by reference.

TECHNICAL FIELD

The present embodiments are directed to the field of electronics, and more particularly to home automation systems and related methods.

BACKGROUND

There are a number of home automation systems and approaches that seek to permit automated control of electrical devices in a house. The popularity of home automation has been increasing due to the greater availability of smartphones and tablets. As noted in "The Problem With Home Automation's Internet Of Things (IoT)", and article appearing in Forbes dated Sep. 26, 2013, home automation was typically for wealthy consumers with an expensive system to control lights, home theater, security, air conditioning, and home audio. This market has expanded with many do it yourself (DIY) products now available, and, although the products are useful, they may be difficult to aggregate. In other words, as explained in the article, difficulties could arise if a consumer bought a Nest thermostat, Kwikset door lock, Phillips Hue lighting device, Lutron light switch, Sonos audio system, and Belkin wireless plugs. The consumer would need to have multiple applications each requiring time to setup, learn, and use. Additionally, the article states that there is no easy way to make devices work together, such as if the consumer wanted to trigger one event using one device based on another event from another device.

Multiple communication protocols may also be problematic. In particular, different devices may operate using different communication protocols, for example, Wifi, Zigbee, Zwave, Insteon, Itron, RadioRA2, and others. This may create additional difficulties for home automation.

One approach to address these shortcomings is for the consumer, which may include a user and/or enterprise, to use a service and device aggregator that provides one application and a consolidated wireless adapter unit. The user would contract with such a provider for multiple years. Unfortunately, as noted in the article, the consumer may not benefit from the most advanced hardware and software.

Another approach, as noted in the Forbes article, is to provide a single application that attempts to consolidate disparate applications and consolidate wireless adaptors, for example, using each of the different communications protocols. Still further improvements to the operation and integration of devices may be desirable.

SUMMARY

A home automation (HA) system may include a plurality of addressable HA devices and a user interface device configured to permit user social networking and generate user social networking data based thereon. The HA system may also include a controller and a memory coupled thereto and configured to store measured user health data and determine user physical activity data based upon the plurality of addressable HA devices. The controller and the memory may be configured to generate a user health score based upon the user social networking data, user health data, and user physical activity data and communicate the user health score via the cloud. Accordingly, the health of a user may be tracked, for example, to predict improvement or decline in the user's health.

The controller may be configured to generate a notification when the user health score exceeds a threshold. The controller may be configured to determine the physical activity data over a period of time and generate a plurality of user health scores based upon the determined physical activity level at intervals within the period of time, for example. The controller may be configured to compare the plurality of user health scores and generate a notification based upon consecutive declining heath scores, for example.

The user interface may be configured to generate the user social networking data based upon a time of social networking. The user interface may be configured to generate the user social networking data based upon a type of social networking activity of a plurality of different social networking activities performed via the user interface device, for example. The type of social networking activity may include at least one of photo sharing, live video chat, and operation of a social networking website.

The user interface device may include a portable housing, a display carried by the portable housing, and wireless communications circuitry carried by the portable housing. The user interface may also include a user interface device controller coupled to the display and the wireless communications circuitry and configured to perform at least one wireless communications function.

Each of the plurality of addressable HA devices may include one of a room occupancy sensor, a bed sensor, a step counter, a heart rate monitor, a blood pressure monitor, a temperature sensor, and a weight scale, for example. The HA system may also include an electronic device configured to communicate with the cloud for downloading of the user health score.

A method aspect is directed to a method of communicating a user health score in an HA system that includes a plurality of addressable HA devices. The method may include permitting, via a user interface device, user social networking and generating user social networking data based thereon. The method may also include using a controller and a memory coupled thereto to store measured user health data and determine user physical activity data based upon the plurality of addressable HA devices. The controller and memory may also be used to generate a user health score based upon the user social networking data, user health data, and user physical activity data, and communicate the user health score via the cloud.

BRIEF DESCRIPTION OF THE DRAWINGS

FIG. 2a is a schematic block diagram of a message queue for use in the system of FIG. 1a.

FIG. 3 is a schematic diagram of an action server for use in the system of FIG. 1a.

FIG. 4 is a schematic diagram of operation of an analytics server for use in the system of FIG. 1a.

FIG. 5 is a schematic diagram of a camera server for use in the system of FIG. 1a.

FIG. 6 is a schematic diagram of a configuration server for use in the system of FIG. 1a.

FIG. 7 is a schematic diagram of a debug server for use in the system of FIG. 1a.

FIG. 8a is a schematic diagram of a discovery server for use in the system of FIG. 1a.

FIG. 8b is another schematic diagram of the discovery server of FIG. 8a.

FIG. 9 is a schematic diagram of a notification server for use in the system of FIG. 1a.

FIG. 10 is a schematic diagram of a loader server for use in the system of FIG. 1a.

FIG. 11 is a schematic diagram of a status server for use in the system of FIG. 1a.

FIG. 12 is a schematic diagram of a web server for use in the system of FIG. 1a.

FIG. 13a is a schematic diagram of a security server in the system of FIG. 1a.

FIG. 14a is a diagram of a user interface displaying contextual help on a remote device of the system of FIG. 1a.

FIG. 14b is a diagram of a user interface displaying contextual help on a remote device of the system of FIG. 1a.

FIG. 15a is a diagram of a user interface showing addressable devices arranged by room on a remote device of the system of FIG. 1a.

FIG. 15b is a diagram of a user interface showing addressable devices arranged by device type on a remote device of the system of FIG. 1a.

FIG. 15c is a diagram of a user interface showing addressable devices arranged by scene type on a remote device of the system of FIG. 1a.

FIG. 16 is a diagram of a user interface showing a color picker for use with an LED light addressable device of the system of FIG. 1a.

FIG. 19 is a schematic diagram of bridges in the system of FIG. 1a.

FIG. 21a is a diagram illustrating sandboxed processes in the system of FIG. 1a.

FIG. 21b is another schematic diagram illustrating sandboxed processes in the system of FIG. 1a.

FIG. 22 is a diagram illustrating a responsive scene definition in the system of FIG. 1a.

FIG. 23 is a flow diagram illustrating ingredient responsive scenes in the system of FIG. 1a.

FIG. 24 is a diagram of a user interface showing recommended purchases based upon ingredients to complete a scene in the system of FIG. 1a.

FIG. 25 is a diagram of a user interface showing the ability of a user to choose from a list of ingredient blocks for a scene in the system of FIG. 1a.

FIG. 26 is a diagram of a user interface showing suggested device operation blocks based upon user input for a scene in the system of FIG. 1a.

FIG. 27 a diagram of a user interface showing a prompt for user input to choose what device provides an ingredient for a scene in the system of FIG. 1a.

FIG. 28 is a diagram of a user interface showing different scenes for a given set of ingredients or devices in the system of FIG. 1a.

FIG. 29a is a diagram of a user interface showing a prompt for user input to choose devices to map a scene to devices specific to a home in the system of FIG. 1a.

FIG. 29b is a schematic block diagram of operation of an HA device scene controller in the HA system of FIG. 1a.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1A:
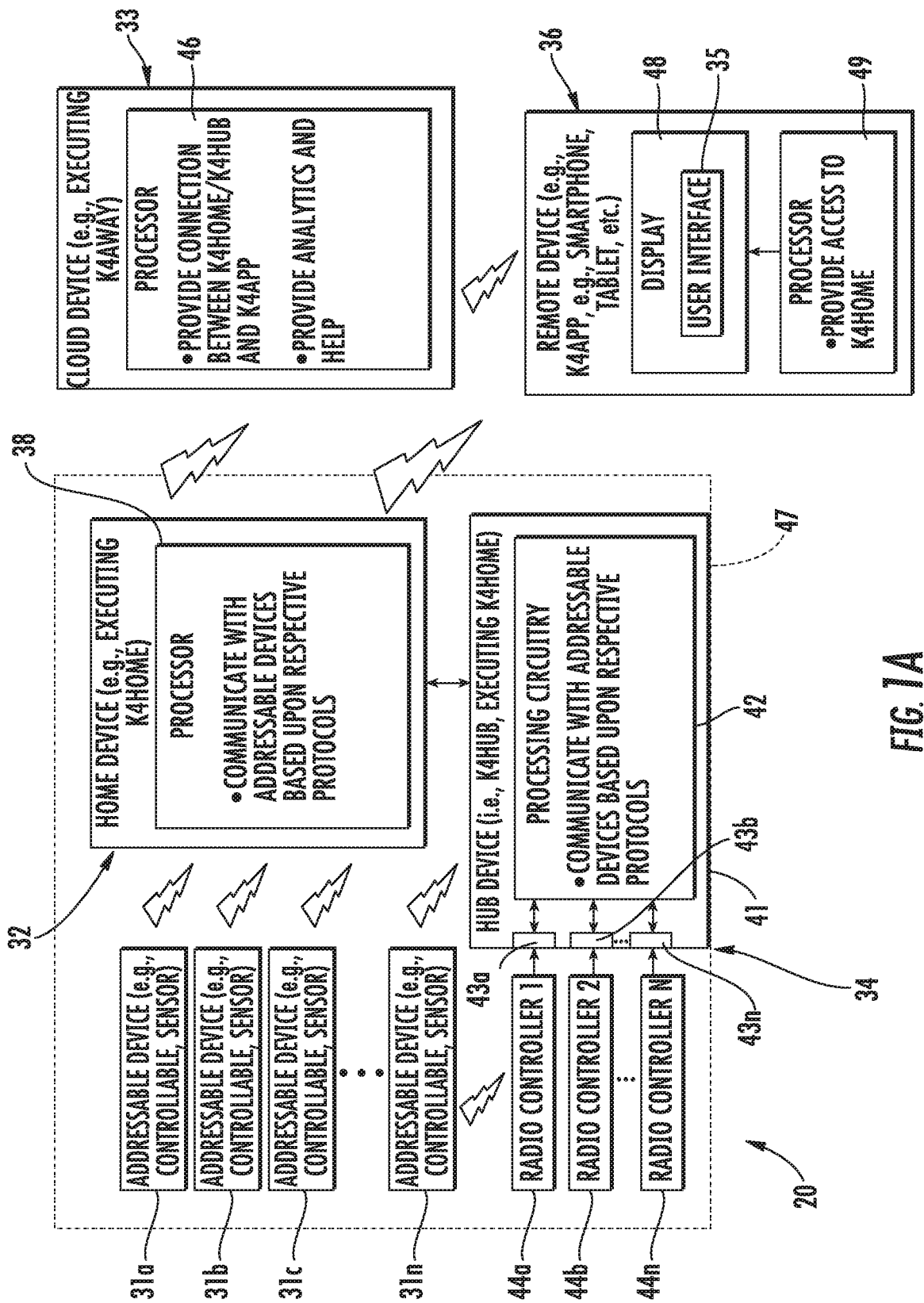
FIG. 1a is a schematic diagram of an electronic device integration system in accordance with an embodiment of the present invention.

Referring initially to FIG. 1a, an electronic device integration system is illustratively in the form of a home automation (HA) system 20, and which is referred to as the K4Connect system. The HA system 20 illustratively includes a plurality of addressable devices 31a-31n, a home device 32, a remote device 36, and cloud device 33. While an HA system 20 is described herein, it should be understood that the system is not limited to use in a home and may be used in any setting, commercial, industrial, residential, etc.

Addressable devices 31a-31n may include controllable devices and/or sensors, for example, a motion detector, thermostat, light switch, audio controller, door lock, and/or camera. Of course, the addressable devices may include additional or other devices.

While a cloud device 33 or hardware server is described, it should be understood by those skilled in the art that the processes and functions performed by the cloud device may be performed by a processor 46 or by multiple processors in different geographic locations and over different networks in what is understood by those skilled in the art as the cloud. The home device 32 may be a personal computer, tablet computer, standalone computing device, or any other computing device. The HA system 20 may also include a hub device 34 (i.e., a K4Hub). In some embodiments, the hub device 34 and the home device 32 may be within a home 47 and wirelessly connected to a home network, which may provide communication with the Internet. The functions and interconnections of these devices within the system will be described in further detail below.

The K4Home software program runs the K4Connect HA system 20 of home, office, business, and building automation for addressable devices 31a-31n that can be connected into the program. The K4Home software is available as a software only package that can be loaded onto a personal computer or other small computer devices, for example, the home device 32. The functions of the K4Home software are executed by respective processors or processing circuitry on one or more devices running the K4Home software, for example, a processor 38 of the home device 32 as will be described below.

The K4Hub 34 is a device that may also run the K4Home software and hosts the system architecture on the device. The K4Hub 34 includes a housing 41 and hub processing circuitry 42 carried by the housing. The K4Hub 34 also includes a plurality of radio ports 43a-43n, for example, universal serial bus (USB) ports carried by the housing 41 and for coupling to any of a plurality of radio controllers 44a-44n. The K4Hub 34 runs the system locally and can communicate with the addressable devices 31a-31n directly instead of routing through a cloud based process. In other words, the hub processing circuitry 42 cooperates with radio controllers 44a-44n that are plugged in to communicate with addressable devices 31a-31n based upon the respective protocols.

The radio controllers 44a-44n may each be for a given radio protocol. For example, a Z-wave radio controller may be plugged into one of the radio ports 43a-43n, which allows the K4Hub 34 to communicate with Z-wave based addressable devices. A second or third radio controller may be plugged into the radio ports 43a-43n of the K4Hub for adding the ability to communicate with controllable devices using second and third radio protocols.

The K4Hub 34 is an improvement on current technology since it reduces the latency and system failures common on current home automation devices that require a network connection. Similarly to the K4Hub 34, the K4Home software running on a personal computer, for example, the home device 32, can be augmented with additional home automation communication protocols such as ZigBee and Z-Wave by attaching ports through the K4Hub or computer's USB port.

The K4App is the location of the user interface 35 of the K4Connect HA system 20 and allows the user to access the K4Home software and control the K4Connect system 20 through or from the remote device 36, for example, a smartphone or tablet device that includes a display 48 and a processor 49 coupled to the display. The user interface 35 may be also accessed by a desktop application for a personal computer and/or by an on-screen application for a television. There may be more than one remote device 36 and each remote device may be a different type of device.

In some embodiments, the remote device 36 may connect "locally" without communicating through or with the cloud device 33. This may be particularly advantageous because communication may not rely on network connectivity and function locally independent of the Internet. Additionally, communication may be relatively faster and more reliable.

The remote server or cloud device 33, which runs software referred to as K4Away, is a cloud-based subscription system that provides the connection between the local K4Home software, for example, running on the home device 32 or K4Hub 34, and the K4App when outside of the local home network, for example running on the remote device 36. K4Away also provides the connection between the K4Home software and K4Connect system analytics and help system. The K4App may, in some embodiments, connect directly to K4Home, i.e., the home device 32 or K4Hub 34, without communicating through the cloud device 33 or indirectly without communication through the cloud device.

Figure 1B:
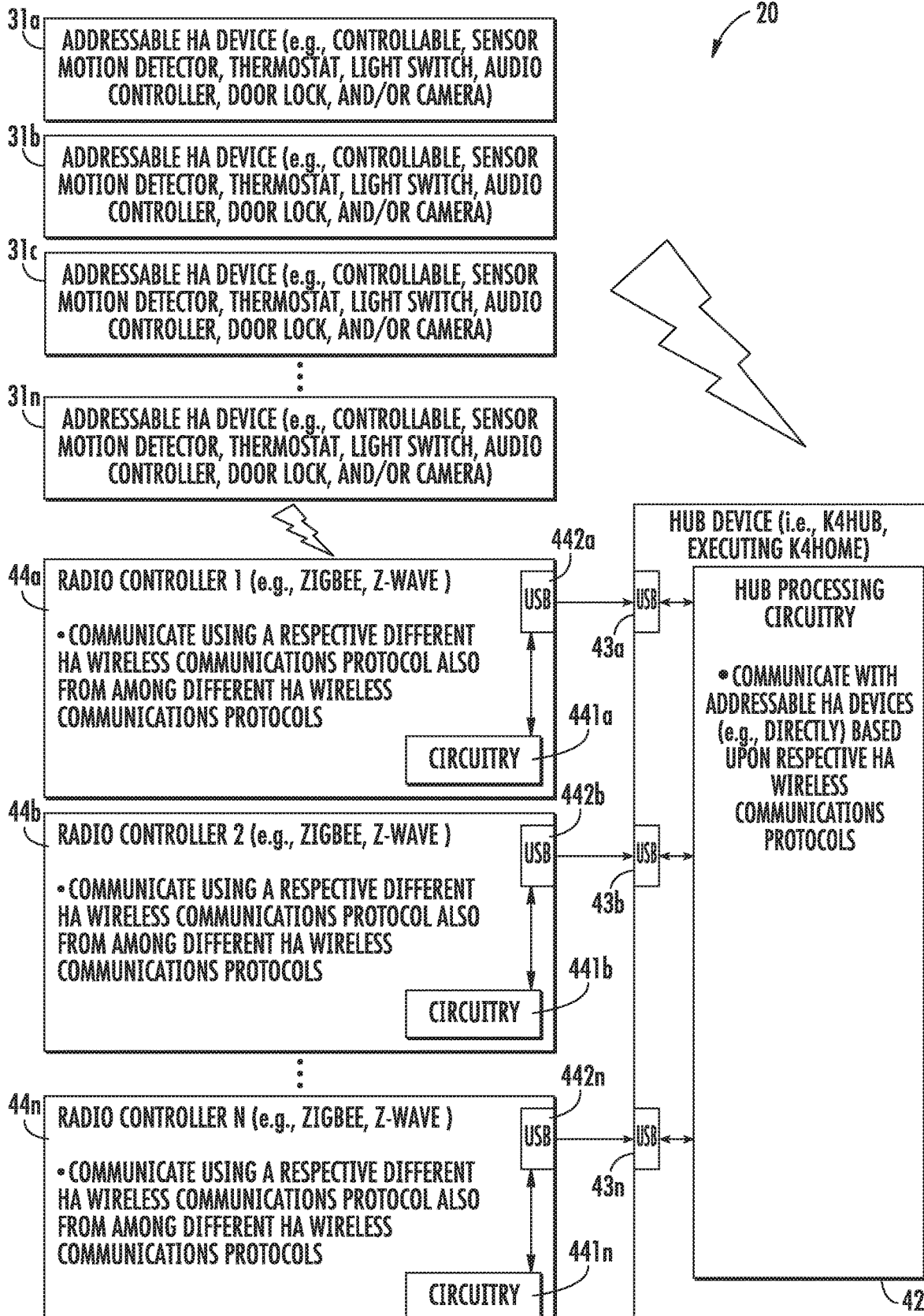
FIG. 1b is a schematic diagram of an HA system in accordance with an embodiment.

Referring now to FIG. 1b, the above-described components of the HA system 20 will be described. The HA system 20 includes addressable HA devices 31a-31n, each configured to wirelessly communicate using a respective HA wireless communications protocol from among different HA wireless communications protocols. The addressable HA devices 31a-31n may include any of motion detectors, thermostats, light switches, audio controllers, door locks, and/or cameras. Of course, the addressable HA devices 31a-31n may include other and/or additional devices.

The HA system 20 also includes HA wireless radio controllers 44a-44n, each configured to wirelessly communicate using a respective different HA wireless communications protocol also from among the different HA wireless communications protocols. Each HA wireless radio controller 44a-44n includes circuitry 441a-441n and a connector 442a-442n coupled thereto. The HA wireless radio controllers 44a-44n may be Zigbee controllers, Z-Wave controllers, and/or other types of controllers, for example.

The HA system 20 also includes an HA hub device 34 that includes a housing 41 and wireless radio port connectors 43a-43n carried by the housing. Each port connector 43a-43n is configured to couple to a respective connector 442a-442n of a corresponding HA wireless radio controller 44a-44n. The port connectors 43a-43n may be USB connectors, for example, and/or other or additional types of connectors. The HA hub device 34 also includes hub processing circuitry 42 coupled to the wireless radio port connectors 43a-43n. The hub processing circuitry 42 communicates with the addressable HA devices 31a-31n based upon the respective HA wireless communications protocols. In some embodiments, the HA wireless radio controllers 44a-44n may communicate directly with the addressable devices via the HA hub device 34, for example, instead of routing through a cloud based process, as will be appreciated by those skilled in the art.

A method aspect is directed to a method of communicating in the HA system 20. The method includes using HA wireless radio controllers 44a-44n to wirelessly communicate using a respective different HA wireless communications protocol from among the different HA wireless communications protocols. The method also includes using the HA hub device 34 to communicate with the addressable HA devices 31a-31n based upon the respective HA wireless communications protocols.

Figure 2A:
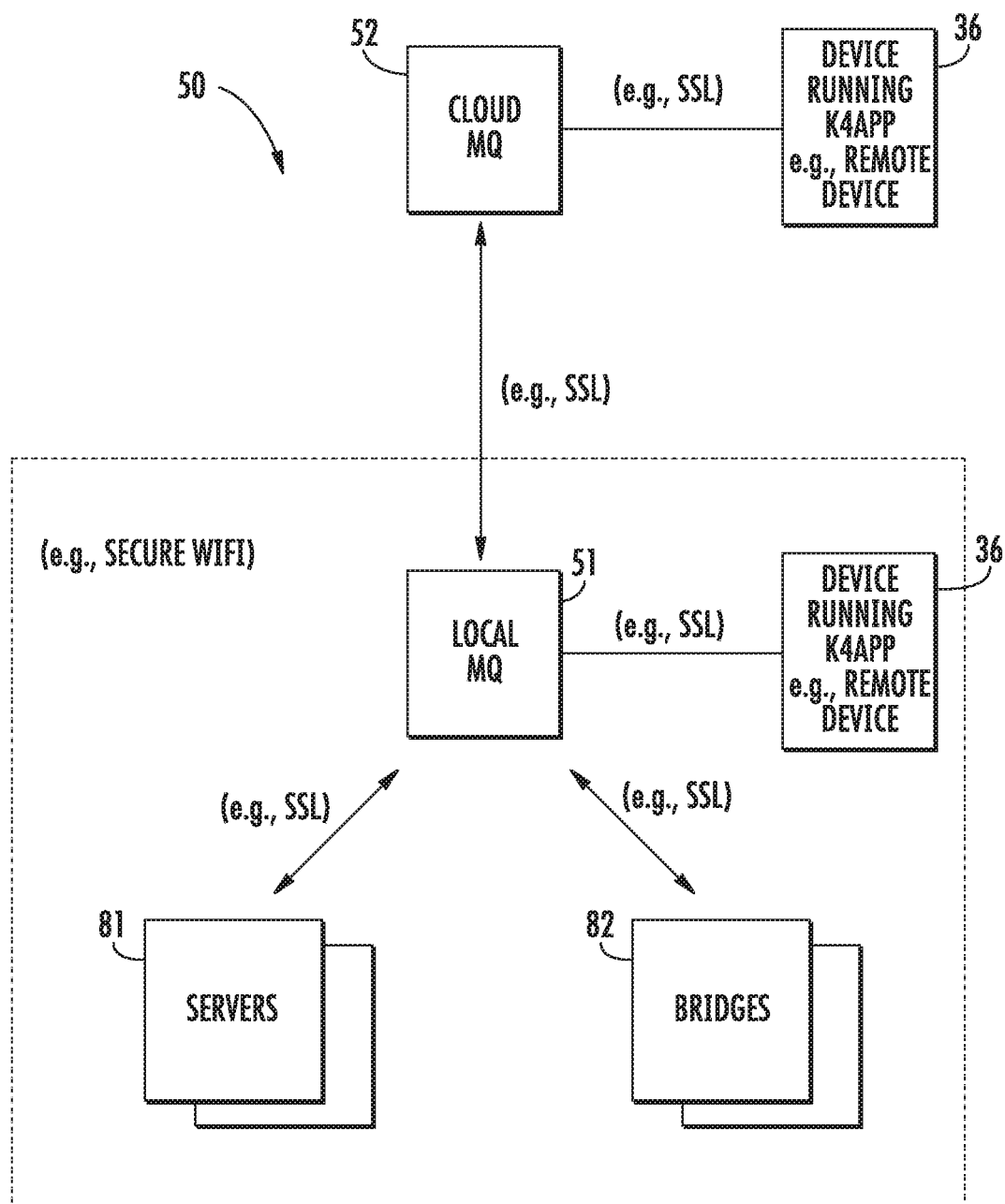

Referring now additionally to FIG. 2a, the primary functions of the HA system 20 (i.e., K4Connect) are based around an independent standalone message queue server 50 that is a combination of an independent local message queue 51 located on a device running the K4Home software and a cloud message queue 52 hosted on the cloud device 33 (i.e. K4Away), which provides connectivity to registered devices outside the local home network. Communication between the message queues 51, 52 and connected addressable devices 31a-31n, connected servers, and connected bridges use web sockets as the transport medium, for example.

Both the local and cloud message queues 51, 52 function independently but remain continuously connected so that no matter the user location, communication to and from the connected device, e.g., servers, and bridges is still available. The continuous connection is initiated from the local message queue 51 to reduce security issues that may be inherent when piercing a firewall of a local network. Having the connection originate from inside the firewalled system, for example, allows for the message queues 51, 52 to more easily connect while maintaining the security integrity of the home system. In other words, each remote device 36 connects to the cloud message queue 52 and not directly to the local message queue 51 or any of the K4Home 32 or K4Hub 34. Additionally, communication between the local message queue 51 and the cloud message queue 52, the connected addressable devices 31a-31n, servers, and bridges may be SSL encrypted including on the local network for increased security. When the K4App, for example, via the remote device 36, is connected to the cloud or remote server 33, the continuous connection allows for the user's connection to the cloud server to serve as a direct connection to the local message queue 51.

The local message queue 51 receives and distributes messages to and from the cloud message queue 52 and to and from the local servers 81 and device bridges 82. This distribution technique for the messages allows for independence for each component of the program and leaves the logic or prescribed action to the individual servers or bridges. This independence of the components of the program may also reduce the probability of system crashing errors. This also allows for continuous rolling out of new bridges and compatibility of new devices without updating the complete software package, for example.

As will be appreciated by those skilled in the art, a typical prior art automation integration system exchanges messages either all within the home network or all on the Internet by penetrating through a firewall. The embodiments described herein advantageously provide a hybrid messaging approach that includes the increased speed of "in-home" message processing (processing via the Internet adds delay) and has the increased security of the Internet (does not penetrate a firewall to expose the home network).

Figure 2B:
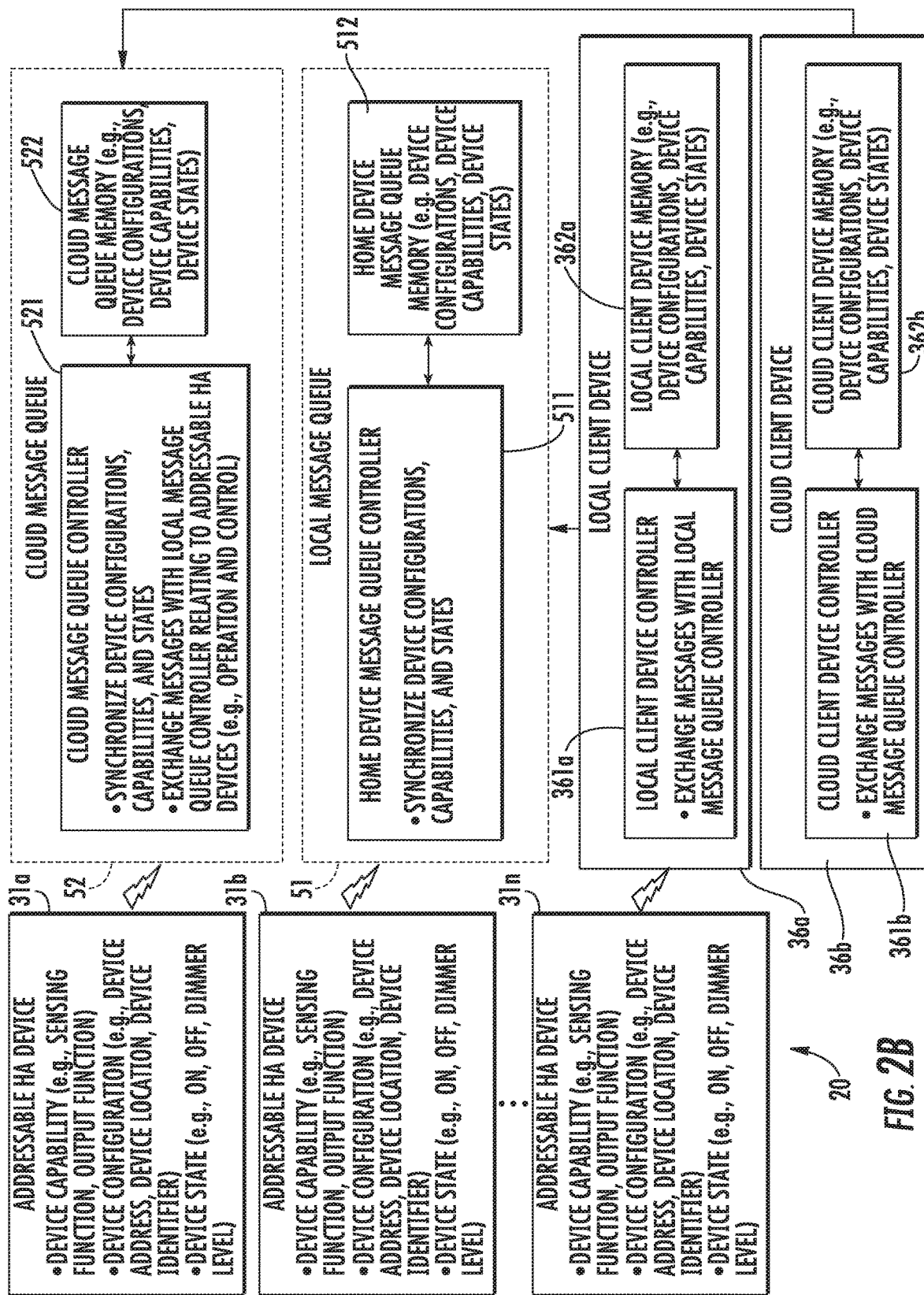
FIG. 2b is a schematic block diagram of an HA system including message queues in accordance with an embodiment.

Referring now to FIG. 2b, another aspect of the HA system 20 with respect to the local and cloud message queues 51, 52 will now be described. The HA system 20 includes addressable HA devices 31a-31n each having associated therewith a respective device capability, device configuration, and device state.

Each device configuration may include at least one of a device address, a device location, and a device identifier, for example. Exemplary device configurations may include an IP address of the device, the location of the device within a house, and channel location (e.g., left, right) in an audio configuration. Of course, the device configuration may include other and/or additional elements.

Each device capability may include at least one of a sensing function, and an output function. For example, with respect to a light switch, the device capability may include the capability to be "on", "off", and be at different "dimmer levels."

Each device state may include a current state from among a plurality of possible states. For example, with respect to a light switch, the current state may be "on", "off", and "dimmed to a given level."

The HA system 20 includes a cloud message queue controller 521 and a cloud message queue memory 522 coupled thereto in the cloud for storing the device configurations, device capabilities, and device states for the plurality of addressable HA devices 31a-31n. The cloud message queue controller 521 and the cloud message queue memory 522 may be part of the cloud message queue 52, for example.

The HA system 20 also includes a home device message queue controller 511 and a home device message queue memory 512 coupled thereto for storing the device configurations, device capabilities, and device states for the plurality of addressable HA devices 31a-31n. The home device message queue controller 511 and the home device message queue memory 512 may be part of the local message queue 51, for example.

The cloud message queue controller 521 and the home device message queue controller 511 synchronize device configurations, device capabilities, and device states for the addressable HA devices 31a-31n. The cloud message queue controller 521 exchanges messages with the local message queue controller 511 relating to the addressable HA devices, for example, for communication with the addressable devices 31a-31n and for synchronization. For example, such messages may include messages related to the operation and control of the addressable HA devices 31a-31n.

A local client device 36a or remote device (e.g., running K4App) includes a local client device controller 361a and local client device memory 362a coupled thereto for storing the device configurations, device capabilities, and device states for the addressable HA devices 31a-31n upon synchronization with the local message queue controller 511. The local client device controller 361a exchanges messages with the local message queue controller 511 relating to the addressable HA devices 31a-31n, for example, sensing, response, and control operations.

A cloud client device 36b or remote device (e.g., running K4App) includes a cloud client device controller 361b and cloud client device memory 362b coupled thereto for storing the device configurations, device capabilities, and device states for the addressable HA devices 31a-31n upon synchronization with the cloud message queue controller 521. The cloud client device controller 361b exchanges messages with the cloud message queue controller 521 relating to the addressable HA devices 31a-31n, for example, sensing, response, and control operations.

As will be appreciated by those skilled in the art, by synchronizing the device configurations, device capabilities, and device states for the addressable HA devices 31a-31n, or messages, communication with a cloud or local client device 36a, 36b may be quicker as processing of the messages, responses, status queries, instructions, etc., for example, can be processed at the cloud or local client device or at the nearest of the cloud or message queue (i.e., the request or communication generally may not have to travel to one or the other of the local or cloud message queues 51, 52).

A method aspect is directed to a method of communicating with a plurality of addressable HA devices 31a-31n each having associated therewith a respective device capability, device configuration, and device state. The method includes using a cloud message queue controller 521 and a cloud message queue memory 522 coupled thereto in the cloud for storing the device configurations, device capabilities, and device states for the plurality of addressable HA devices. The method also includes using a home device message queue controller 511 and a home device message queue memory 512 coupled thereto for storing the device configurations, device capabilities, and device states for the plurality of addressable HA devices. The cloud message queue controller 521 and the home device message queue controller 511 synchronize device configurations, device capabilities, and device states for the plurality of addressable HA devices 31a-31n.

Referring now additionally to FIGS. 3-13, the K4Home program, for example executed using the home device 32 or K4Hub 34, provides for independent servers or functional modules for each of the functions of the HA system 20. The servers 81 are separated from the bridges 82 running on the HA system 20 for security and may allow independent running of the system as a whole. The servers 81 on the home automation integration system 20 include an action server 69, analytics server 54, camera server 61, configuration server 62, debug server 63, discovery server 55, loader server 64, message server, notification server 66, status server 67, update server, web server 68, and security server 56. More servers can be added to the software if new functions are needed. While the term server has been used herein, it should be understood that a server may be one or more standalone software processes that are executed on one or more processors on any device, for example, as described above. The functionality of each server 81 is performed by a processor, controller, and/or related circuitry, particularly on the device which it is executed, for example, the home device processor 38 or the hub device processing circuitry 42, as will be appreciated by those skilled in the art.

The action server is continuously running on the HA system 20, and more particularly, the home device 32, and executes the responsive scenes of the K4Home system or components within the home (FIG. 3). The analytics server 54 logs user and system actions to the cloud storage system or server 33 and receives suggestions of possible responsive scenes the user could implement or actions the user could take to improve their K4Home HA system 20 (FIG. 4).

In the initial K4Home system setup, the analytics server 54 requests advertisements from the servers 81 and bridges 82 on the system. The servers 81 and bridges 82 on the K4Home system 20 return advertisements, which allows for the analytics server 54 to subscribe to the individual servers and bridges. Once subscribed, the servers and bridges 82 send individual events, commands, and variable changes to the analytics server 54, which keeps a log of the data sent.

At intervals, which may be periodic or regular, the analytics server 54 reports the data collected to the cloud system or cloud device 33 via a private globally unique identifier (GUID). The cloud-based analytics or device 33 processes and reviews the anonymized data, storing the data in a cloud database. This data is then used to review the functions of the K4Home HA system 20 which may reveal any problems that may exist in the software. This HA system 20 can also use the data gathered from the security server to assess any security threats and develop mitigation plans. The cloud-based analysis or cloud device 33 also reviews the K4Home system and recommends devices and responsive scenes to the private GUIDs. Once the information in the cloud has been analyzed and gathered by the cloud device 33 it is pushed back to the local analytics server 54 with the next time to "check-in" to the cloud.

The camera server 61 (FIG. 5) locates camera images/video and streams the images/video to the system. The camera server also acts as an image proxy for remote users not able to directly connect to the camera, for example.

The configuration server 62 (FIG. 6) stores the persistent configuration of the home automation integration system 20. The configuration server 62 also uses the device descriptions during the device connection process to setup addressable devices 31a-31n on the HA system 20 in tandem with a device setup wizard. The debug server 63 enables bridge debugging (FIG. 7).

The discovery server 55 (FIG. 8a) finds addressable devices to connect to the K4Connect system 20. The discovery server 55 uses signatures of devices, for example, addressable devices 31a-31n in its search to discover devices that are not natively discoverable for connection to the system. With respect to typical prior art home automation integration systems, certain addressable devices do not automatically broadcast their availability and thus have to be manually connected by the user. Manual entry often involves advanced technical knowledge or having to follow detailed complicated instructions to add the device to their home automation systems, for example, manually entering an IP address, device ID, and/or other identifying information. The discovery server 55 reduces these complications.

Example code executed on the discovery server 55 with respect to a network device and a USB device, respectively, are below:

```
<signature cls="com.k4connect.someNetworkDevice"
description="Example Network Device">
    <mdns>
        <services>
            <service>
                <name>DeviceName.*</name>
                <type>http</type>
                <protocol>tcp</protocol>
            </service>
        </services>
    </mdns>
    <upnp>
        <deviceType>urn:Manufacturer:device:sensor:1</deviceType>
    </upnp>
    <macs>
        <mac>ff:ff:ff</mac>
    </macs>
</signature>
<signature cls="com.k4connect.someUsbDevice"
description="Example USB Device">
    <udev>
        <devices>
            <device>
                <attributes>
                    <attribute name="ID_VENDOR_ID" pattern="10c4"/>
                    <attribute name="ID_MODEL_ID" pattern="ea60"/>
                    <attribute name="DEVNAME" pattern="\/dev\/ttyUSB\d+"/>
                </attributes>
            </device>
        </devices>
    </udev>
</signature>
```

The discovery server 55 is typically always running processes that monitor the system home automation integration 20 either passively waiting for a signal from a new controllable device or scanning the system for signatures of the addressable devices 31a-31n. The discovery server 55 runs UPNP and MDNS processes that use a text match process from the signatures of the addressable devices 31a-31n to identify the controllable device. The discovery server 55 also runs multicast processes and connects to these unconnected addressable devices 83, for example, by a challenge response.

The advantageous elements of the discovery server 55 are the ARP scan and the udev scan. The ARP scan runs a port match for loaded controllable device signatures and runs a challenge-response process to identify the addressable devices 31a-31n. For example, discovery server 55 may query a port with data and get an identifying response based upon the query. The ARP scan also identifies the device by MAC address matching. The other advantageous element is the UDEV scan which uses a USB match for devices connected to the hardware running K4Home and running a TTY Match, which identifies the device with a challenge response process. As will be appreciated by those skilled in the art, any number of elements or network characteristics that define a controllable device signature may be used.

Once the discovery server 55 has discovered a new addressable device (i.e., new to the system 20), it sends notifications over the message queue 51 to the configuration server 62 and notification server 66 (FIG. 8a), which then notify the user of the newly discovered addressable device and begins a wizard set-up process. When a new addressable device becomes available (e.g., new to market and not just the system) for which there is not an identifiable signature, a new signature filter may be added to the discovery server 55.

In some embodiments, advertising from the addressable devices 31a-31n may be used to limit an addressable device. For example, a controllable speaker device may appear to the home automation integration system 20 as a generic device based upon advertising. However, a query based upon a subset of addresses or signature elements may be used, which may increase the speed of controllable device discovery. For example, signature elements may be used to limit or restrict a device type, and discovery may continue based upon the subset.

Figure 8A:
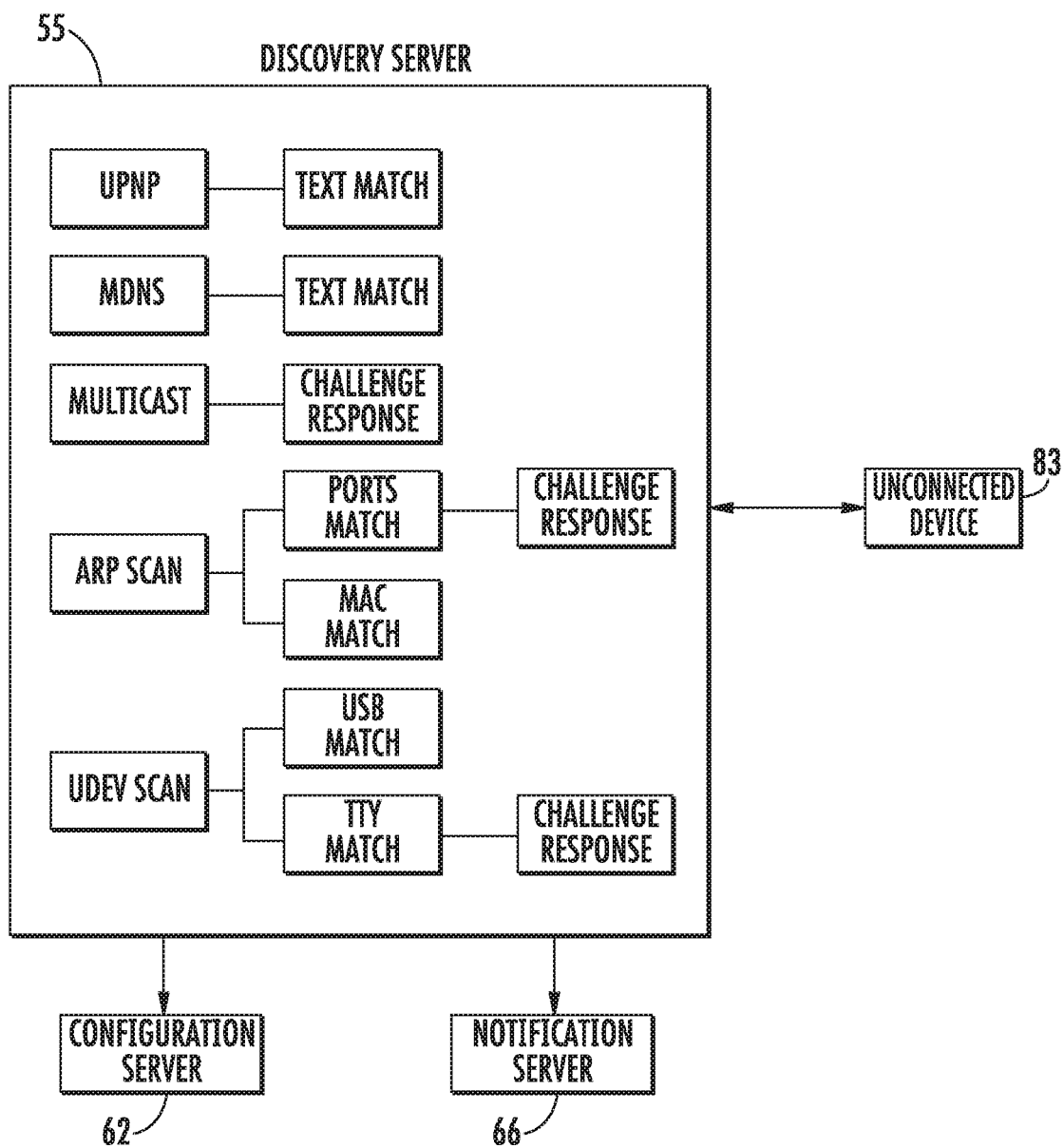
Figure 8B:
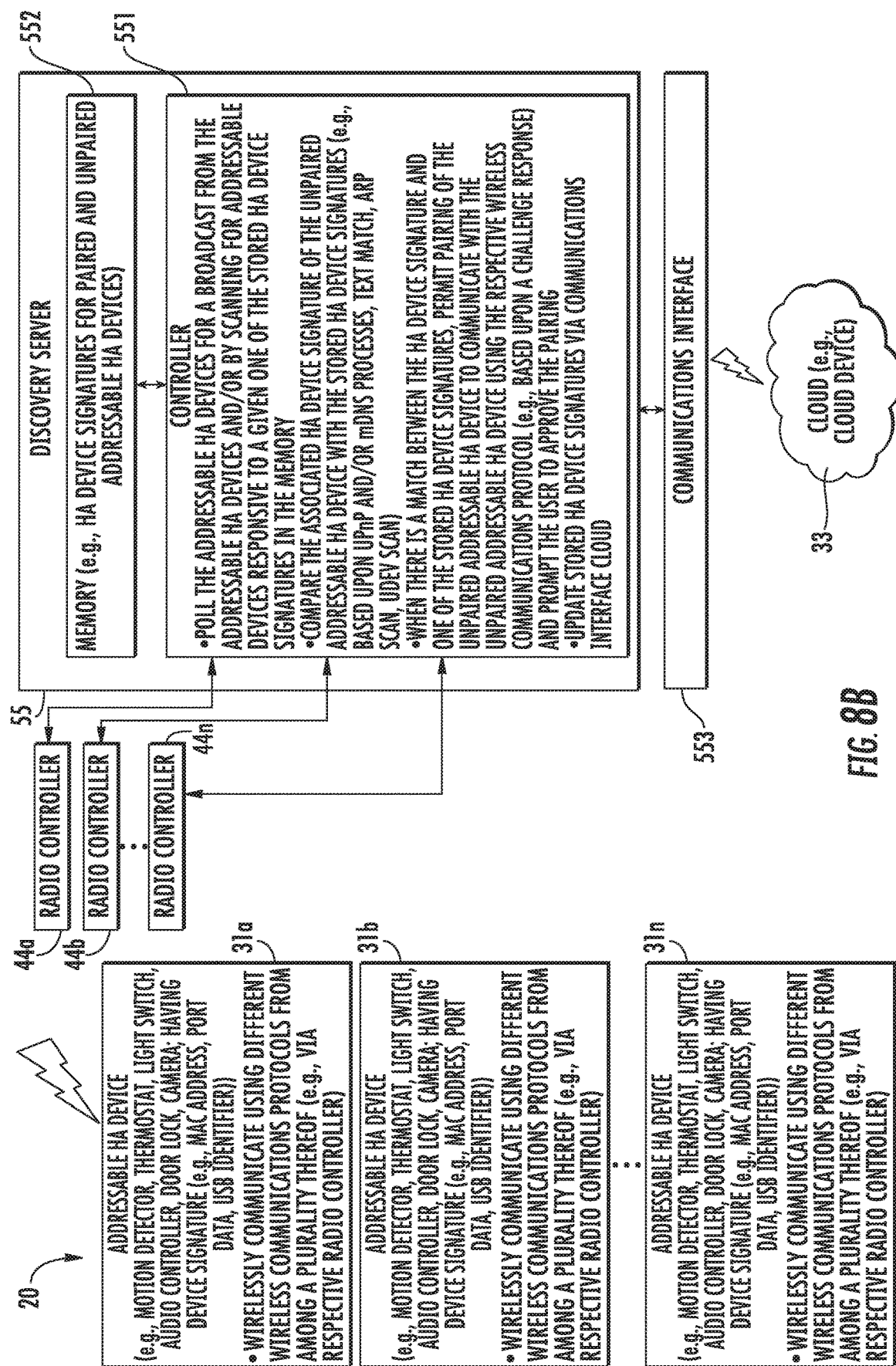

Referring now additionally to FIG. 8b, the discovery server 55 will be described with respect to the HA system 20. The addressable HA devices 31a-31n each have a respective HA device signature associated therewith and each is configured to wirelessly communicate using respective different wireless communications protocols from among different wireless communications protocols. The addressable HA devices 31a-31n may include any of motion detectors, thermostats, light switches, audio controllers, door locks, and/or cameras. Of course, the addressable HA devices 31a-31n may include other and/or additional devices.

The discovery server 55 may be in the form of a controller 551 and a memory 552 coupled thereto. The memory 552 stores HA device signatures for paired and unpaired ones of the addressable HA devices 31a-31n. The HA device signatures may include, for example, MAC addresses, port data, and/or universal serial bus (USB) identifiers.

The controller 551 polls the addressable HA devices 31a-31n and determines an unpaired addressable HA device from among the plurality thereof based upon the polling. The controller 551 may poll the addressable HA devices 31a-31n by polling for a broadcast from the addressable HA devices and/or by scanning for addressable devices responsive to a given one of stored HA device signatures stored in the memory 552.

The controller 551 also compares the associated HA device signature of the unpaired addressable HA device with the stored HA device signatures. The controller 551 may compare the associated HA device signature of the unpaired addressable HA device with the stored HA device signatures based upon at least one of a universal plug and play (UPnP) process and a multicast domain name system (mDNS) process. Any of the UPnP and mDNS processes may be executed based upon a text match process, for example.

In some embodiments, the addressable HA devices 31a-31n may each have port data associated therewith, in which case the controller 551 may poll the addressable HA devices based upon an address resolution protocol (ARP) scan, and compare the associated HA device signature of the unpaired addressable HA device with the stored HA device signatures based upon port data from the ARP scan.

Alternatively or additionally, the controller 551 may poll the addressable HA devices 31a-31n based upon a udev scan, in which case the controller compares the associated HA device signature of the unpaired addressable HA device with the stored HA device signatures based upon the udev scan.

The controller 551, when there is a match between the HA device signature of the unpaired addressable HA device and one of the stored HA device signatures, permits pairing of the unpaired addressable HA device to communicate with the unpaired addressable HA device using the respective wireless communications protocol. The controller 551 may prompt a user to approve pairing of the unpaired addressable HA device. The pairing of the unpaired addressable HA device may be based upon a challenge response from an electronic device associated with a user, for example, the remote device 36.

A communications interface 553 provides communication between the controller 551 and the cloud, for example, the cloud device 33. The controller 551 communicates with the cloud device 33 via the communications interface 553 to update the stored HA device signatures in the memory 552.

The HA system 20 also includes radio controllers 44a-44n coupled to the controller 551. Each of the addressable devices 31a-31n is configured to wirelessly communicate with the controller 551 via respective radio controllers 44a-44n.

A method aspect is directed to a method of permitting pairing of unpaired addressable HA devices 31a-31n in the HA system 20. The method includes using the 551 controller and the memory 552 coupled thereto storing a plurality of HA device signatures for paired and unpaired ones of plurality of addressable HA devices to poll the plurality of addressable HA devices and determine an unpaired addressable HA device from among the plurality thereof based upon the polling. The controller 551 and the memory 552 are also used to compare the associated HA device signature of the unpaired addressable HA device 31a-31n with the stored HA device signatures, and when there is a match between the HA device signature of the unpaired addressable HA device and one of the stored HA device signatures, permit pairing of the unpaired addressable HA device to communicate with the unpaired addressable HA device using the respective wireless communications protocol.

The loader server 64 loads bridges 82 and servers 81 (FIG. 10). The message server runs or operates the message queue 51. The notification server 66 sends notifications from the system 20 to the user interface 35, for example, at the remote device 36 (FIG. 9).

The status server 67 serves as a system wide state machine storing a log of last known state without having to poll devices in the system (FIG. 11). This is accomplished by having the status server 67 perform as a standalone state machine tracking the last known states of the system. As will be appreciated by those skilled in the art, the status server 67 is advantageously an improvement relative to the current common practice where the system stores the state information in the driver stack, for example. The web server 68 runs the user interface content (FIG. 12). In some embodiments, the user interface content may be stored locally.

Figure 13A:
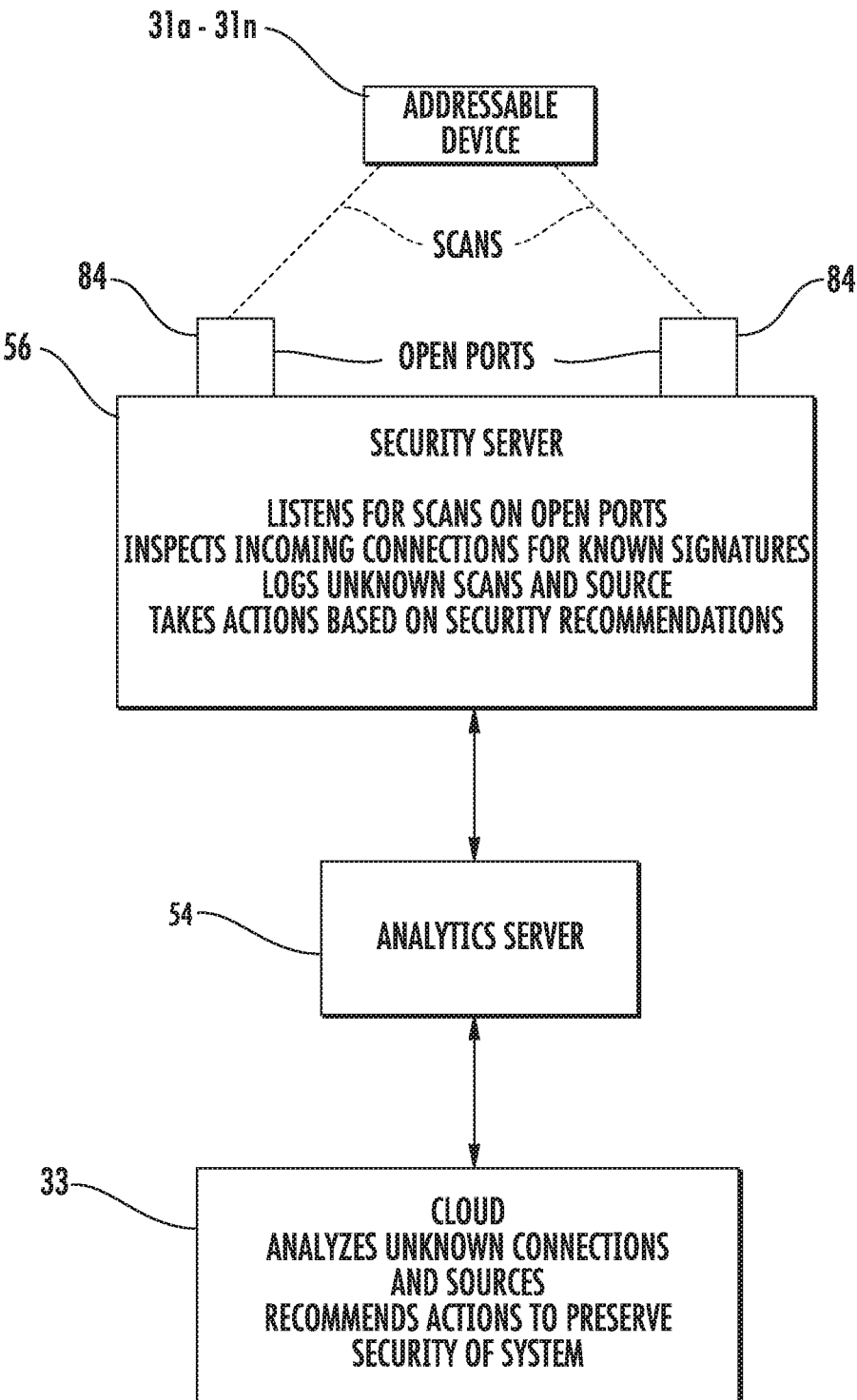

The security server 56 executes security processes of the home automation integration system 20 (FIG. 13a). The security server 56 listens on open communication ports 84 not being used by the home automation integration system 20. This allows the security server 56 to log when a device, for example, an addressable device 31a-31n or remote device 36, scans or connects to the port. The security server 56 may then ignore any device that is known to scan or connect and is not a threat to the system and log when it receives an unknown or unexpected scan. For example, an open port may be scanned by or connected to a connected user's remote iPhone, but since this is an expected action from an iPhone, the security server 56 does not automatically consider this a threat to the home automation integration system 20. If a connected home automation or addressable device 31a-31n, for example, a refrigerator, does the same scan of or connects to the open ports, the security server 56 logs the action, and then reports the logs to the analytics server 54. The security server 56 is aware of what can be considered normal behavior for an addressable device 31a-31n by way of a signature file included for all known controllable devices. In other words, because the types of devices, both remote and controllable, coupled to the home automation integration system 20 on network are known, traffic among the devices can be monitored to maintain security. If traffic or communications associated with a particular device is determined to be erratic, the security server 56 may identify the device as being hijacked and/or malware and flagged for reporting to the analytics server 54. The analytics server 54 uploads the data to the cloud device 33 for security analysis.

An example security server signature that describes what may be considered normal behavior of a network device is below:

```
<signature cls="com.k4connect.someNetworkDevice"
description="Example Network Device">
  <behavior>
    <http>
      <url>http://api.someurl.com/*</url>
      <frequency>300</frequency>
    </http>
    <socket>
      <destination>*</destination>
      <port>80</port>
      <quantity>3</quantity>
    </socket>
  </behavior>
</signature>
```

The cloud server or cloud device 33 may perform an analysis to assess or classify patterns and recommend actions for the security server 56. Some examples of actions for the security server 56 to take include notifying the user of abnormal actions of a device, disconnecting a compromised device from the K4Connect system 20, or ignoring if the action is not malicious. The K4Connect system 20 in some instances may recognize a vulnerability or attack in a manufacturer's smart device and can provide the information about the vulnerability to the manufacturer. Of course, the cloud device 33 may recommend other and/or additional actions for the security server based upon the analysis.

Figure 13B:
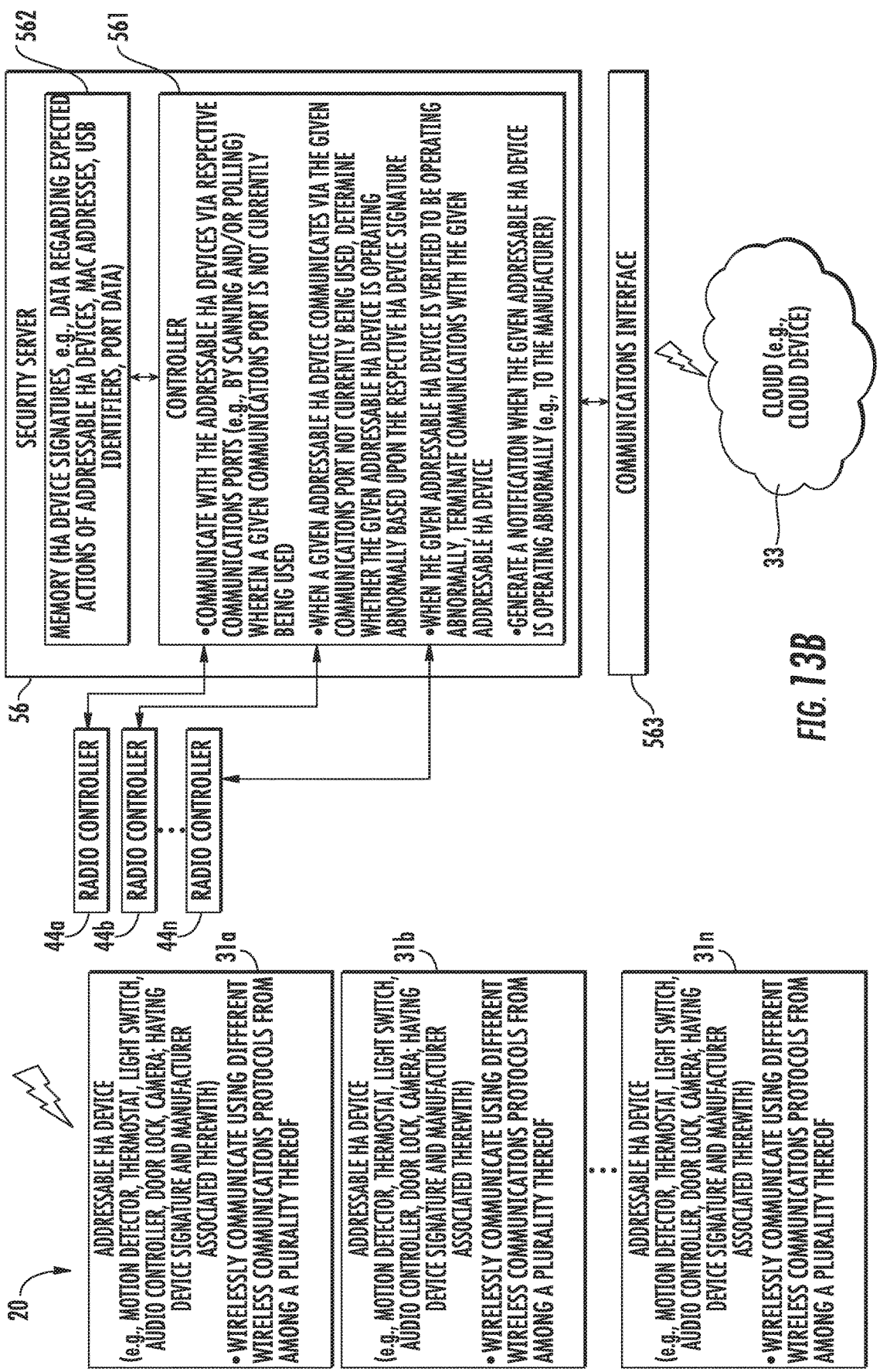
FIG. 13b is another schematic diagram of a security server in accordance with an embodiment.

Referring now to FIG. 13b, the security server 56 with respect to the HA system 20 will now be described. The HA system 20 includes addressable HA devices 31a-31n each having a respective HA device signature associated therewith, which may be stored in a memory 562. The HA device signatures may include data regarding expected actions of the addressable HA devices 31a-31n. The HA device signatures may also include MAC addresses, port data, and universal serial bus (USB) identifiers, for example. Of course, the HA device signatures may include any combination of and/or or additional identifiers that may be used as a basis to characterize operating behavior of the addressable HA devices 31a-31n.

The addressable HA devices 31a-31n may include any of motion detectors, thermostats, light switches, audio controllers, door locks, and/or cameras. Of course, the addressable HA devices 31a-31n may include other and/or additional devices. The addressable devices 31a-31n wirelessly communicate using respective different wireless communications protocols from among different wireless communications protocols.

The HA system 20 includes an HA security controller 561 coupled to the memory 562 and that communicates with the addressable HA devices 31a-31n via respective communications ports, for example by scanning or polling the communications ports. A given communications port is not currently being used or is open. When a given addressable HA device 31a-31n communicates via the given communications port not currently being used, the HA security controller 561 determines whether the given addressable HA device is operating abnormally based upon the respective HA device signature and communicates to the cloud 33 for verification of whether the given addressable HA device is operating abnormally. When the given addressable HA device 31a-31n is verified to be operating abnormally, the HA security controller 561 terminates communications with the given addressable HA device.

The HA security controller 561 also generates a notification when the given addressable HA device 31a-31n is verified to be operating abnormally. In some embodiments, the addressable HA devices 31a-31n each has a manufacturer associated therewith, and the HA security controller 561 may communicate the notification to a respective manufacturer associated with given addressable HA device verified to be operating abnormally. Of course, the HA security controller 561 may communicate the notification to another device and/or entity, as will be appreciated by those skilled in the art.

The HA system 20 may also include a communications interface 563 that provides communication between the HA security controller 561 and the cloud 33. The HA security controller 561 communicates with the cloud 33 via the communications interface 563, for example, to update the stored HA device signatures in the memory 562.

The HA system 20 also includes radio controllers 44a-44n coupled to HA security controller 561. Each of the addressable devices 31a-31n may be configured to wirelessly communicate with the HA security controller 561 via respective radio controllers 44a-44n.

A method aspect is directed to a method of communicating in the HA system 20. The method includes using the HA security controller 561 to communicate with the addressable HA devices 31a-31n via respective ones of the communications ports, with a given communications port not currently being used. The method also includes using the HA security controller 561 to, when a given one of the addressable HA devices 31a-31n communicates via the given communications port not currently being used, determine whether the given addressable HA device is operating abnormally based upon the respective HA device signature, communicate to the cloud 33 for verification of whether the given addressable HA device is operating abnormally, and terminate communications with the given addressable HA device and generate a notification when the given addressable HA device is verified to be operating abnormally.

Another aspect is directed to setup wizards of the K4Home software. A setup wizard may provide an increasingly simple and relatively uniform setup process for each device connected to the K4Connect system 20, and particularly, connected to K4Home. The setup wizard may limit the actionable items on each screen step of the wizard to maintain simplicity. For example, the setup wizard may allow one question and one data input received from that question before moving to the next step in the wizard.

Each setup wizard is based upon prebuilt templates that allow software developers to collect the data for the setting up of a device without having to build new user interface components. Each setup wizard may be customizable for developers and bridge builders, for example. Customization may be achieved by allowing each setup wizard to have a unique style sheet while keeping base styles consistent. Beyond the base styles, the user interface in each setup wizard may be changeable, but it is desirable that these changes be within specific parameters. If no suitable template is available for the developer, for example, user interface components may be created. Custom templates would still use K4Connect components when available and may not contradict the relatively simple and uniform setup process provided by the K4Home software.

Figure 14A:
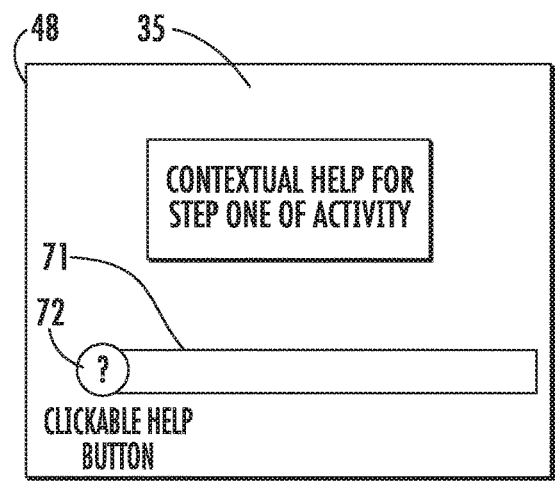
Figure 14B:
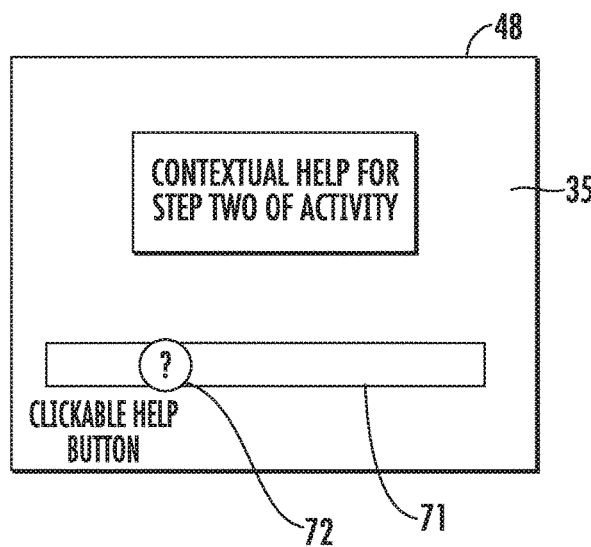

Referring additionally to FIGS. 14a and 14b, each setup wizard may also provide contextual help by supplying a progress bar 71, for example, on the display 48 of the remote device 36 or as part of the user interface 35, for example, that includes a help button 72 on the progress bar. The help button 72 links to help that corresponds to the user's current step in the setup wizard. In other words, the user will be presented with different instructions on the display 48 depending on where the user is in the setup process. This may be particularly advantageous in that it aids users in steps in the setup that are frequently problematic and may make the user experience more adaptive and easier than current home automation setups.

Referring now to FIGS. 15a-15c, the user interface 35 may provide several different ways to control the K4Connect system 20 or to control addressable devices 31a-31n on the K4Connect system. For example, the K4Connect system 20 may be controlled by room (FIG. 15a), by scene (FIG. 15b), and by device types (FIG. 15c). Of course, the K4Connect system 20 may be controlled in other fashions or using other techniques.

The user interface 35, which may be presented via the display 48 of a remote device 36, for example, a touch screen display of a mobile phone, allows the user to view addressable devices 31a-31n by device category or by the location (FIG. 15a) of the addressable device. The user can also switch directly from the addressable device selection from the location to the addressable device category view. The user interface 35 also advantageously tracks the history of the devices used by tracking the last contacted device. This may allow the user to directly access recently used addressable devices 31a-31n more quickly instead of searching back through prior pages of the user interface. The user interface 35 may also provide increased usability by allowing the entire screen of the remote device 36, for example, a touch-screen remote device to be used to adjust the addressable device 31a-31n instead of locating a single point on the touch-screen display for adjustment. In some embodiments, addressable devices 31a-31n may be controlled via the user interface 35 by way of voice recognition, for example. Other types of control may also and/or additionally be used, for example, biometrics, or gesture (e.g., arm, hand, eye) recognition.

Figure 16:
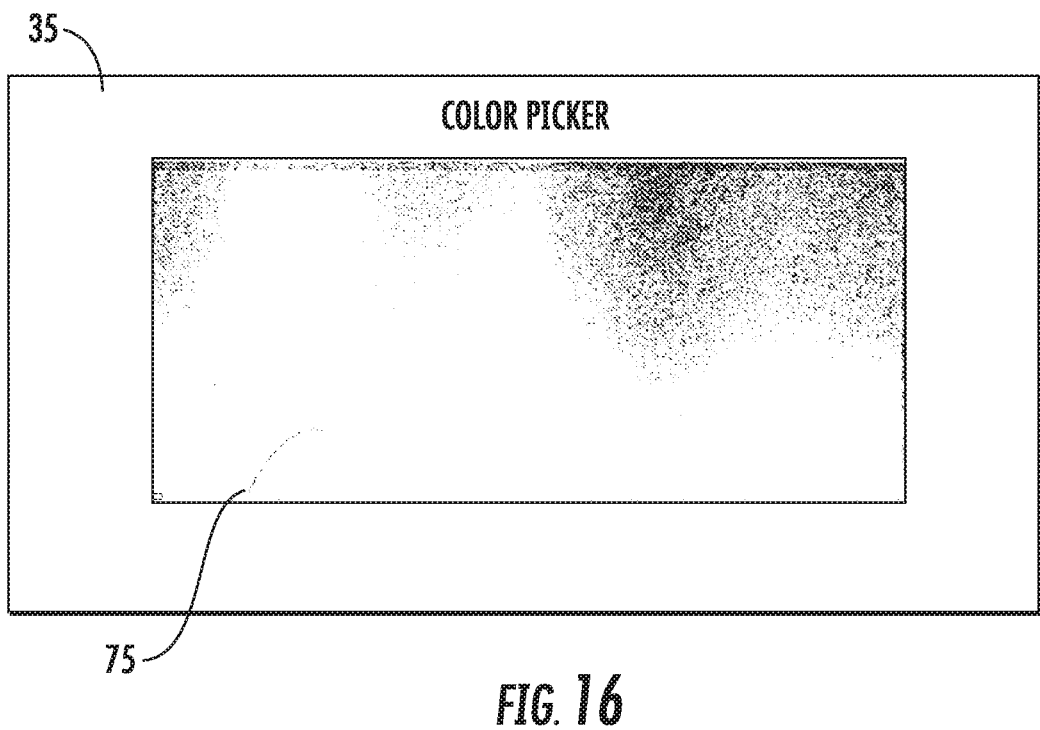

Referring now to FIG. 16, when one or more of the addressable devices 31a-31n are in the form of a light emitting diode (LED) bulb, the user interface 35 includes an LED color picker 75 function. The LED color picker 75 provides a more accurate method to set colors in controllable multi-color LED light bulbs 31a. Currently, the user selects a color from a palette and the bulb will adjust to closest color possible. This may result in a variation between what the user selects from the display 48 and the actual output from the multi-color LED light bulb 31a.

The LED color picker 75 by way of the processor 49 of the remote device 36, detects the colors the multi-color LED light bulb 31a is capable of producing and presents those color options to the user. This is done, for example, by determining the CIE delta of the multi-color LED light bulb 31a. The CIE delta may be determined by the manufacturer, the data for which may be stored in the remote device 36 or received from the cloud device 33.

Figure 17:
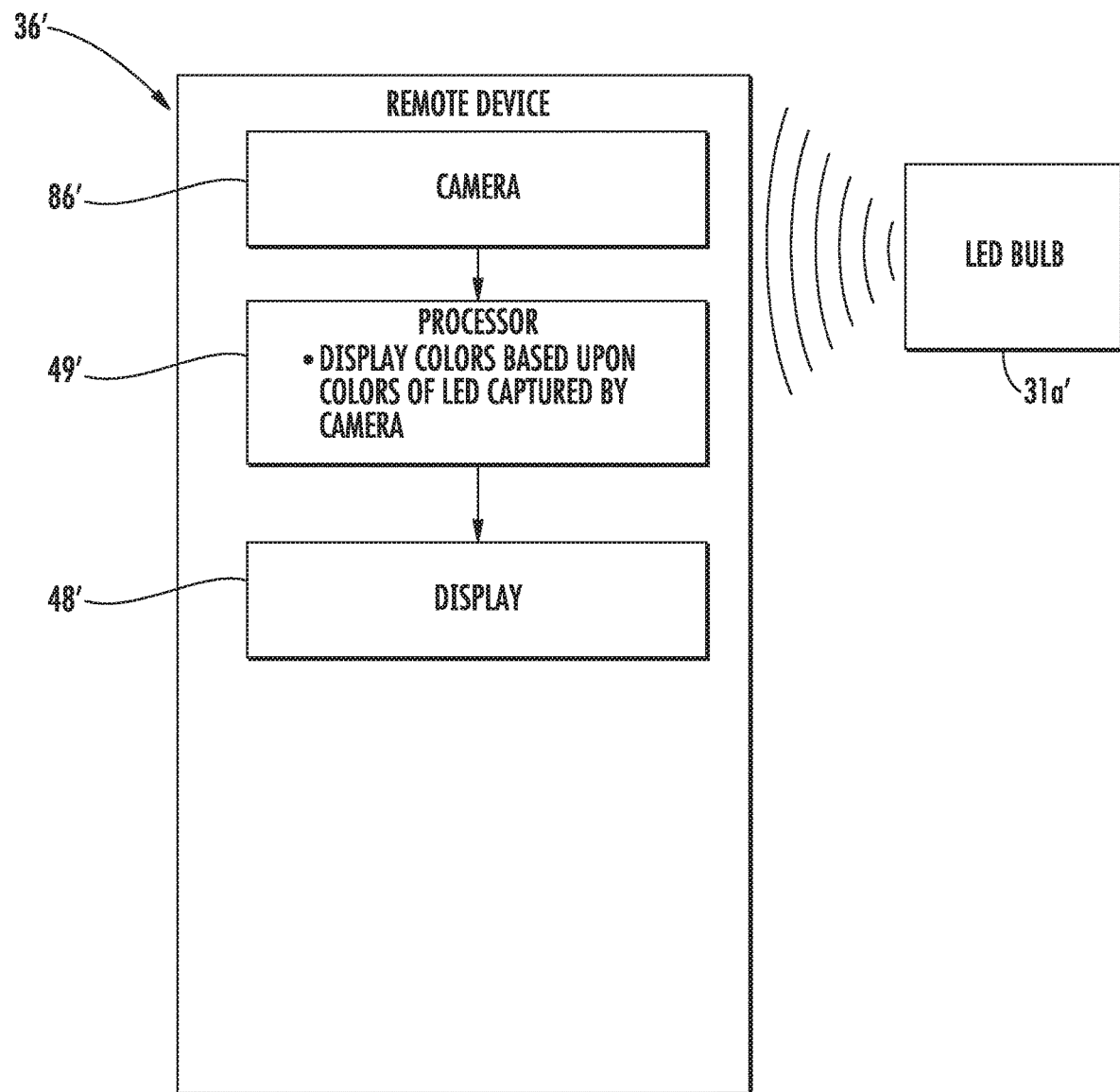
FIG. 17 is a schematic block diagram of a remote device and an LED light bulb addressable device in accordance with an embodiment of the present invention.

Referring to FIG. 17, in another embodiment, when the remote device 36' includes a camera 86', the processor 49' of the remote device may cooperate with the camera to capture the colors actually illuminated by the multi-color LED light bulb 31a'. The processor 49' of the remote device 36' then displays on the display 48' the available colors of the multi-color LED light bulb 31a' based upon the stored CIE delta information or the captured images. Colors are calculated in the CIE triangle versus finding the color at the end of the delta. Additionally, in some embodiments, the remote device signature, as discussed above, in the case of a multi-color LED light bulb may include the CIE delta of the bulb based upon the model number, for example. The user then chooses the exact color from the options on the display 48' and the multi-color LED light bulb 31a' changes to selected color. This matches the user expectation to the light bulb output in contrast to the current method which selects a color based upon an approximation.

As will be appreciated by those skilled in the art, the capabilities of the multi-color LED light bulb 31a are typically much less than what a typical CIE diagram shows. The embodiment described herein advantageously determines the color displaying capabilities of the multi-color LED light bulb 31a and allows selection of those actual colors rather than making an approximation.

Figure 18:
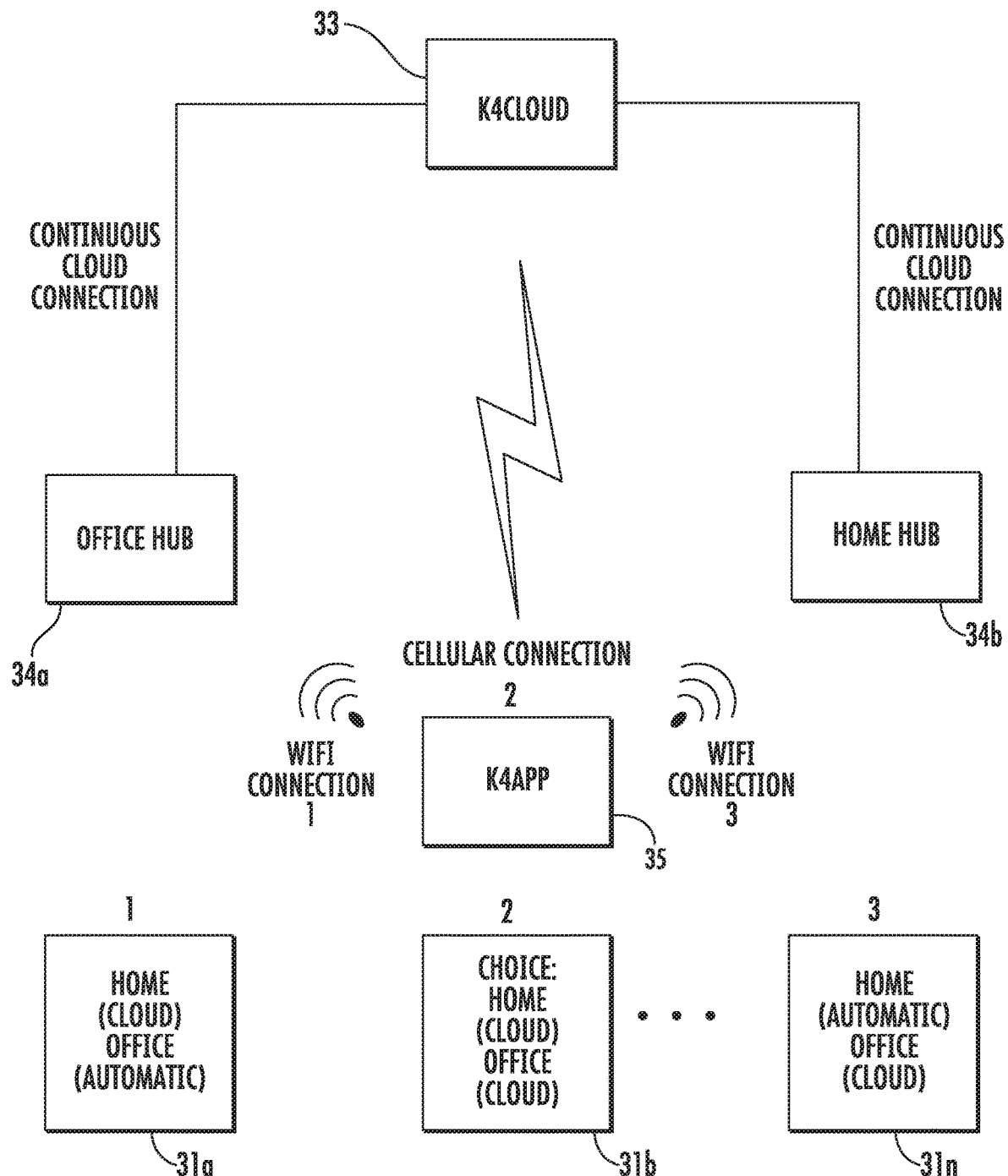
FIG. 18 is a schematic diagram of an interface between multiple hub devices in accordance with an embodiment of the present invention.

Referring now additionally to FIG. 18, the user interface 35 also provides an interface for interacting with multiple K4Hubs hubs or hub devices, for example a home hub 34b and an office hub 34a. Currently in the home automation market, end users either cannot set up multiple hubs in their homes or the hubs are combined in a cloud system preventing the user from being able to make an obvious distinction between the systems. The K4Connect system 20 advantageously permits the user the option of controlling multiple hubs from the user interface 35 by connecting, for example, automatically, to the local hub and connecting to any other hubs through the cloud.

When connected to a local network, for example, via Wifi, the user interface 35 of a remote device 36 may automatically connect (i.e., without user intervention) to the hub device 34a, 34b on the same local network. When using a cellular connection or Wifi network that is not connected to a hub device 34a, 34b, the user interface 35 allows the user to pick which of the multiple systems they would like to view. For example, in a first scenario, a connection to a hub device 34a located in the user's office. The K4App or user interface 35 controls the addressable devices 31a-31n from the office hub 34a, but the user has the option to switch the user interface to control other connected hubs. In a second scenario, when the user is connected only to a cellular network such as an LTE network, the user interface 35 provides an option for the user to choose between the connected hubs if there is more than one, so the user can pick between home hub 34b or the office hub 34a. In a third scenario, the user is connected to the home hub 34b and the user interface 35 automatically controls the addressable devices 31a-31n at home, but the user can switch to controlling the office hub 34a on the user interface.

When a new addressable device 31a-31n is detected by the home device 32 or the hub device 34 (i.e. a device running K4Home), for example, new software for supporting the newly detected addressable device may be downloaded. For example, an "app store" for controllable devices may provide support or drivers for the newly detected controllable device. The "app store" may be hosted by the cloud server 33 or third party provider, for example. With respect to the app store being available on the cloud server, the cloud server may store in memory addressable device drivers. When a new addressable device 31a-31n is detected by the home device 32 or hub device 34, the home or hub device may "pull down" the corresponding driver or software and not an entire software package.

Figure 19:
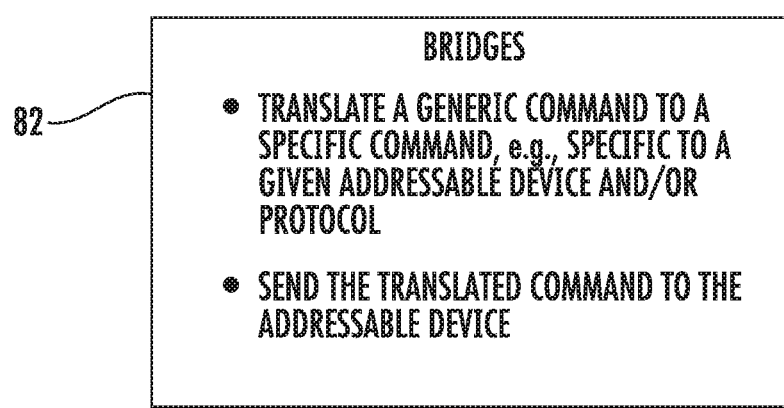

Referring now additionally to FIG. 19, further details of the bridges 82 will now be described. The K4Connect bridges 82 provide a translation layer for the message queue or message queue server 50 to communicate with the addressable devices 31a-31n connected to the K4Connect system 20. When a user or a predefined scene executes a command on the K4Connect system 20, the message queue 50 sends a generic form of the message through the Node.js APIs to the associated bridge 82. The generic form of the message may be sent through different APIs or by different techniques as will be appreciated by those skilled in the art. The bridge 82 then translates the generic command to the specific command for the addressable device 31a-31n and sends the translated command to the addressable device.

The independence of the bridges 82 advantageously allows developers to write bridges for nearly any controllable device independently of the whole K4Connect system 20. After a bridge 82, which may generally be stored separately from the message queue 50, is coded, for example, it may be downloaded and integrated into the message queue 50 without having to update the entire K4Connect software program.

More particularly, when a new addressable device 31a-31n is detected by the home device 32 or hub device 34, for example, new software for supporting the newly detected controllable device may be downloaded, i.e. a bridge. For example, an "app store" for controllable devices may provide support or the bridge for the newly detected controllable device. The "app store" may be hosted by the cloud server 33 or third party provider, for example. With respect to the app store being available on the cloud device 33, the cloud device may store in memory addressable device bridges. When a new addressable device 31a-31n is detected by the home device 32 or hub device 34, the home or hub device may "pull down" the corresponding bridge or software and not an entire software package.

The independence of each bridge also allows for better usage of bandwidth and storage space on the home K4Connect system 20. By not downloading an entire software update package every time a bridge is updated, the user and K4Connect preserve Internet bandwidth and data. Also, the ability to only download the bridges 82 that are desired by each user allows the user to preserve memory space on the device running K4Home, e.g. the home device 32 and/or K4Hub 34. This preserved memory space allows the K4Connect system 20 to provide a relatively large number of bridges for new home automation devices with less concern of bloated software or limited storage space on user devices, for example.

Figure 20:
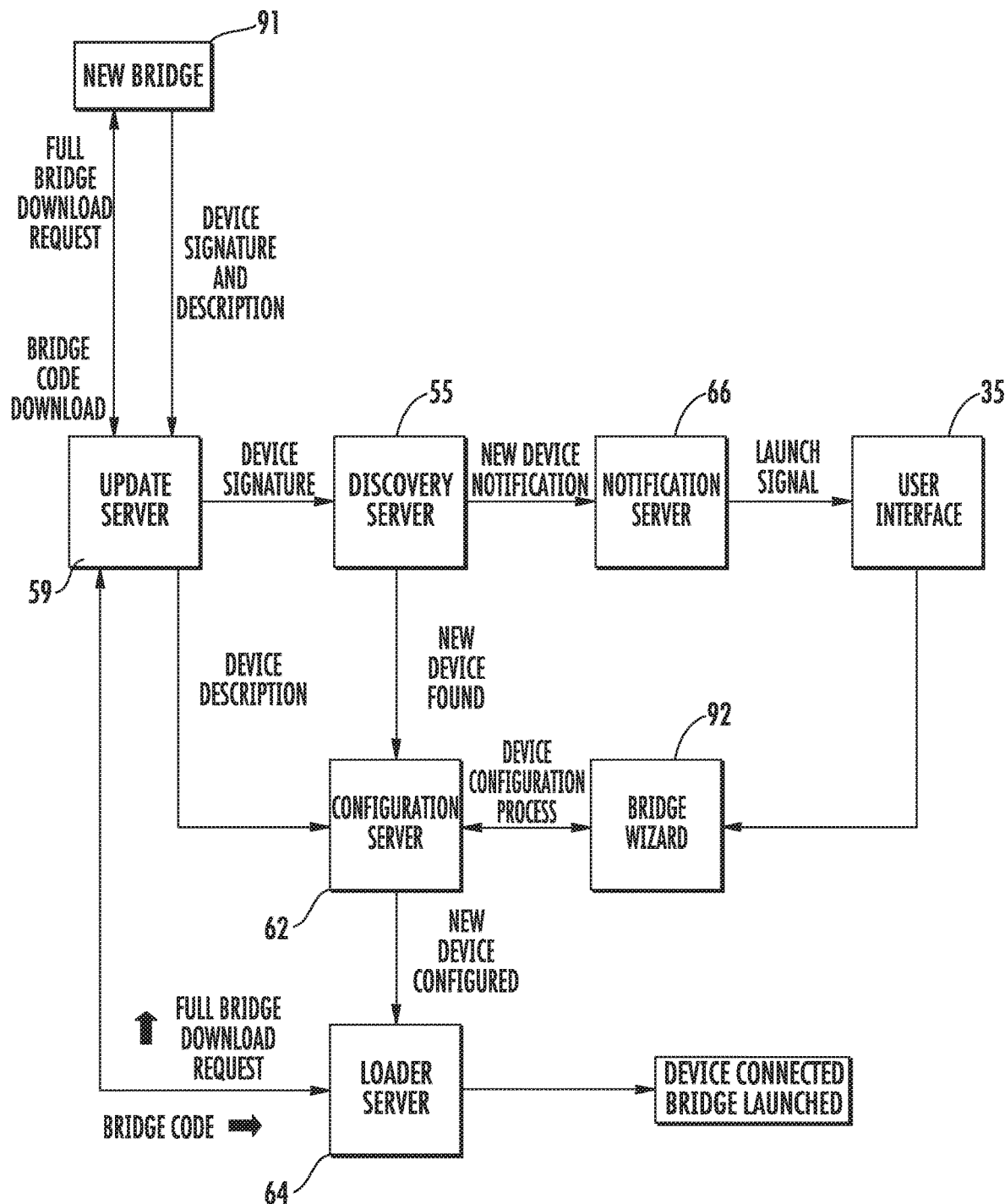
FIG. 20 is a schematic diagram of operation of system of FIG. 1a when a new bridge is added.

Referring now particularly to FIG. 20, when a new bridge 91 is created and loaded to the K4Connect system 20, the update servers 59 on each K4Connect system connect to the cloud device 33 or K4Away and are notified when the system performs an update. As will be appreciated by those skilled in the art, the update server 59 may perform an update by communicating with the cloud server and determining based upon communication therewith whether an update exists (e.g., based on date, update ID, etc.). The device signature of the new bridge and the device description are sent to the update server 59. The file or files associated with the device signature and description are generally much smaller than the complete bridge file, which is downloaded if the new controllable device is ultimately connected to the K4Connect system 20. The update server 59 sends the device signature to the discovery server 55 and the device description to the configuration server 62. The device signature allows the discovery server 55 to scan available ports and recognize if a new addressable device 31a-31n that can be connected by the new bridge 91 is in the home. The device description includes the wizard process, for example, as described above, to set up the new controllable device. When the discovery server 55 finds a new controllable device that can be connected by a new bridge 91, the discovery server 55 sends a message to the configuration server 62 notifying the configuration server of the new addressable device. The discovery server 55 also sends a new addressable device notification to the notification server 66, which launches the user interface 35 on the display 48 of the remote device 36 to inform the user of the new addressable device. The bridge wizard 92 is also launched. The bridge wizard 92 gathers the information for the device description and requested from the configuration server 62.

Once the information has been gathered and user provides a response, for example via the bridge wizard 92, the configuration server 62 notifies the loader server 64 of the new configured addressable device. The loader server 64 requests the full bridge download from the update server 59, and the update server requests the full bridge from the cloud device 33 or K4Away. The update server 59 sends the full bridge download to the loader server 64, which stores the file and launches the new bridge. The newly connected controllable device is thus connected to the K4Connect system 20.

Figure 21A:
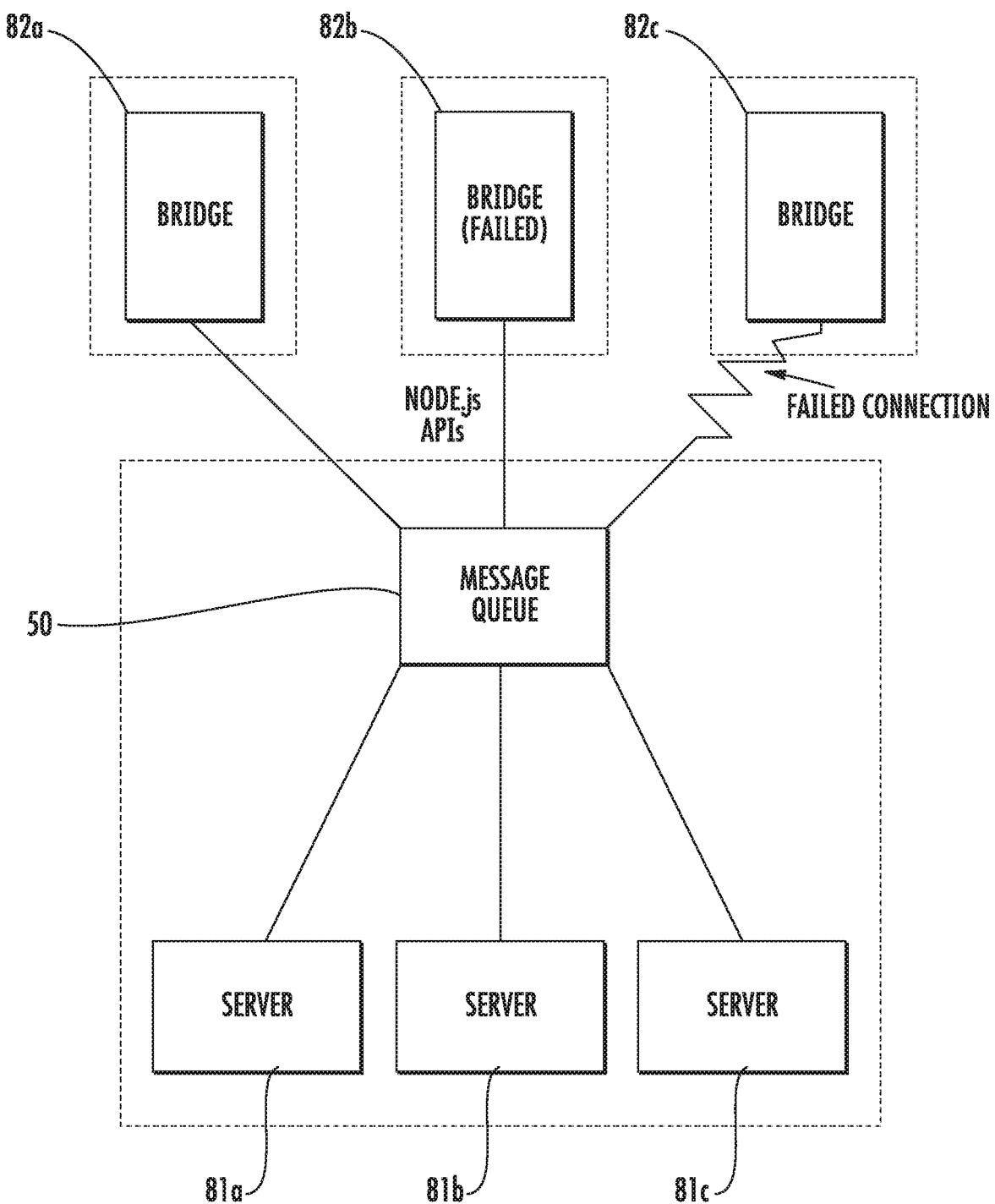

Referring now additionally to FIG. 21a, the bridges 82a-82c of the K4Connect system 20 are also what may be referred to by those skilled in the art as "sandboxed" so that the system may be less subject to interruption should a given bridge fail fails. If one of the bridges 82a-82c fails or if the connection to the message queue 50 fails, the remaining system components continue to function. The bridges 82a-

82c execute the communication between themselves and the message queue 50 so that if there is a failure in communication, the bridge will generally restart the communication. If a bridge 82a-82c has an error, for example, the loader server 64 reloads the bridge 82a-82c. These sandboxed processes limit or reduce restarting of the entire software program running on the home device 32 or hub device 34 if an error occurs in a bridge 82a-82c. However, one effect on the K4Connect system 20 may be the inability of controlling the specific addressable devices 31a-31n associated with the failed bridge 82a-82c, which may be quickly remedied when the loader server 64 reloads the bridge. The functionality of the message queue 50, other servers, and other bridges are generally unaffected. As noted above, bridges may be installed on demand, for example, as needed, for communicating with addressable HA devices.

Figure 21B:
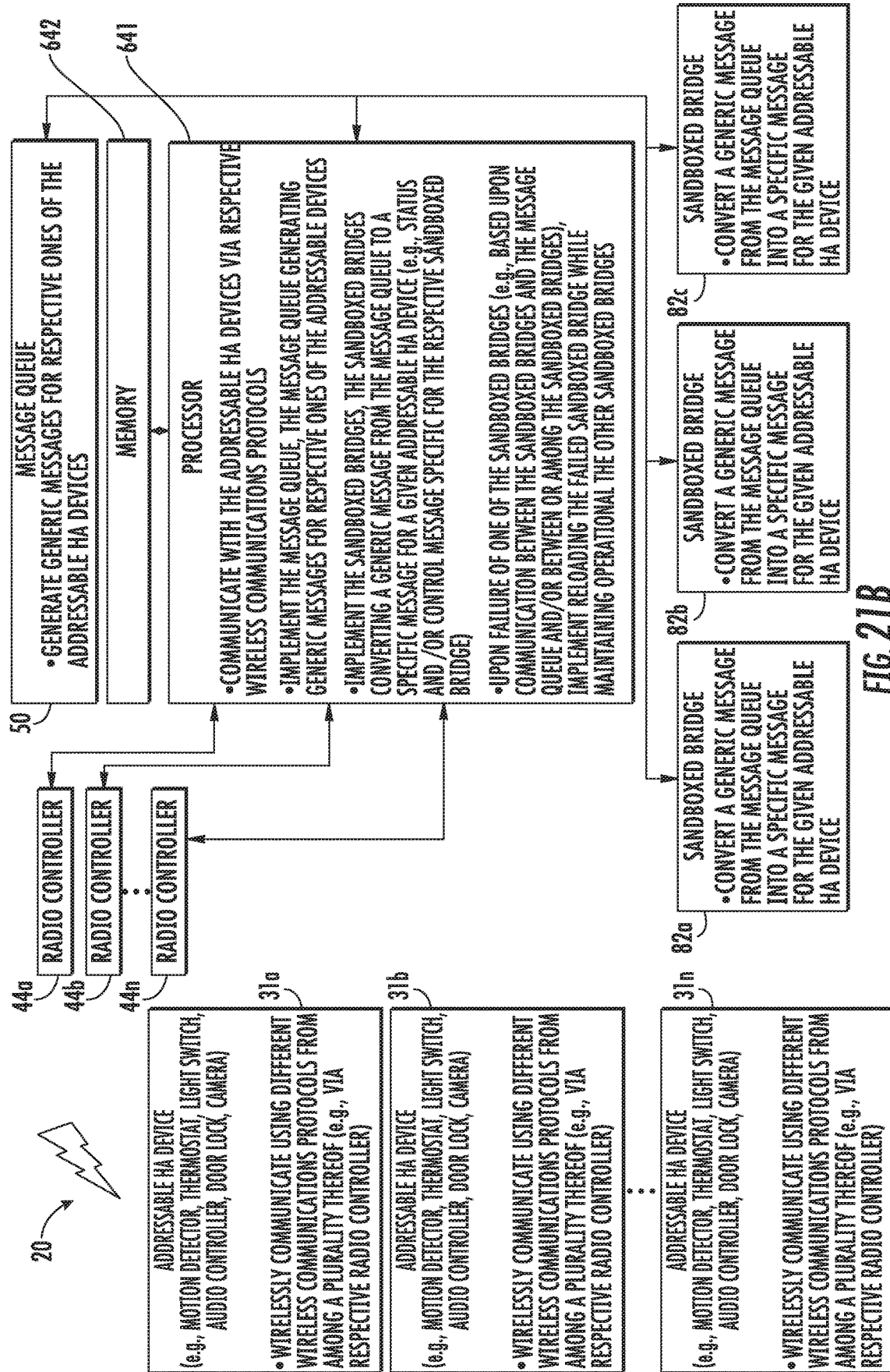

Referring now to FIG. 21b, the "sandboxed" bridges 82a-82c will now be described with respect to the HA system 20. The HA system 20 includes addressable HA devices 31a-31n. The addressable HA devices 31a-31n may include any of motion detectors, thermostats, light switches, audio controllers, door locks, and/or cameras. Of course, the addressable HA devices 31a-31n may include other and/or additional devices. The addressable devices 31a-31n wirelessly communicate using respective different wireless communications protocols from among different wireless communications protocols.

A processor 641 and a memory 642 associated with the processor may cooperate to perform the functions described above with respect to the sandboxed bridges 82a-82c. More particularly, the processor 641 and the memory 642 are configured to implement the message queue 50. That is, the message queue 50 generates generic messages for respective ones of the addressable HA devices 31a-31n. The processor 641 and the memory 642 also implement sandboxed bridges 82a-82c. Each sandboxed bridge 82a-82c converts a generic message from the message queue 50 into a specific message for a given one of the addressable HA devices 31a-31n. The specific message may be a specific control and/or status message that is specific for the respective sandboxed bridge 82a-82c.

Upon failure of one of the sandboxed bridges 82a-82c, the processor 641 and memory 642 implement reloading the failed sandboxed bridge 82a-82c while maintaining operational the other sandboxed bridges. The processor 641 may determine the failed one sandboxed bridge 82a-82c based upon communication between the sandboxed bridges and the message queue 50 and/or communication between or among the sandboxed bridges 82a-82c, for example.

The HA system 20 also includes radio controllers 44a-44n coupled to the processor 641. Each of the addressable devices 31a-31n may be configured to wirelessly communicate with the processor 641 via respective radio controllers 44a-44n.

A method aspect is directed to a method of maintaining operational a plurality of sandboxed bridges 82a-82c in the HA system 20. The method includes using the processor 641 and the memory 642 associated therewith to generate, via the message queue 50, a plurality of generic messages for respective ones of the plurality of addressable HA devices 31a-31n and convert a generic message from the message queue into a specific message for a given one of the addressable HA devices using the plurality of sandboxed bridges 82a-82c. The method also includes using the processor 641 and memory 642 to, upon a failure of one of the plurality of sandboxed bridges 82a-82c, reload the failed sandboxed bridge while maintaining operational the other sandboxed bridges.

Figure 22:
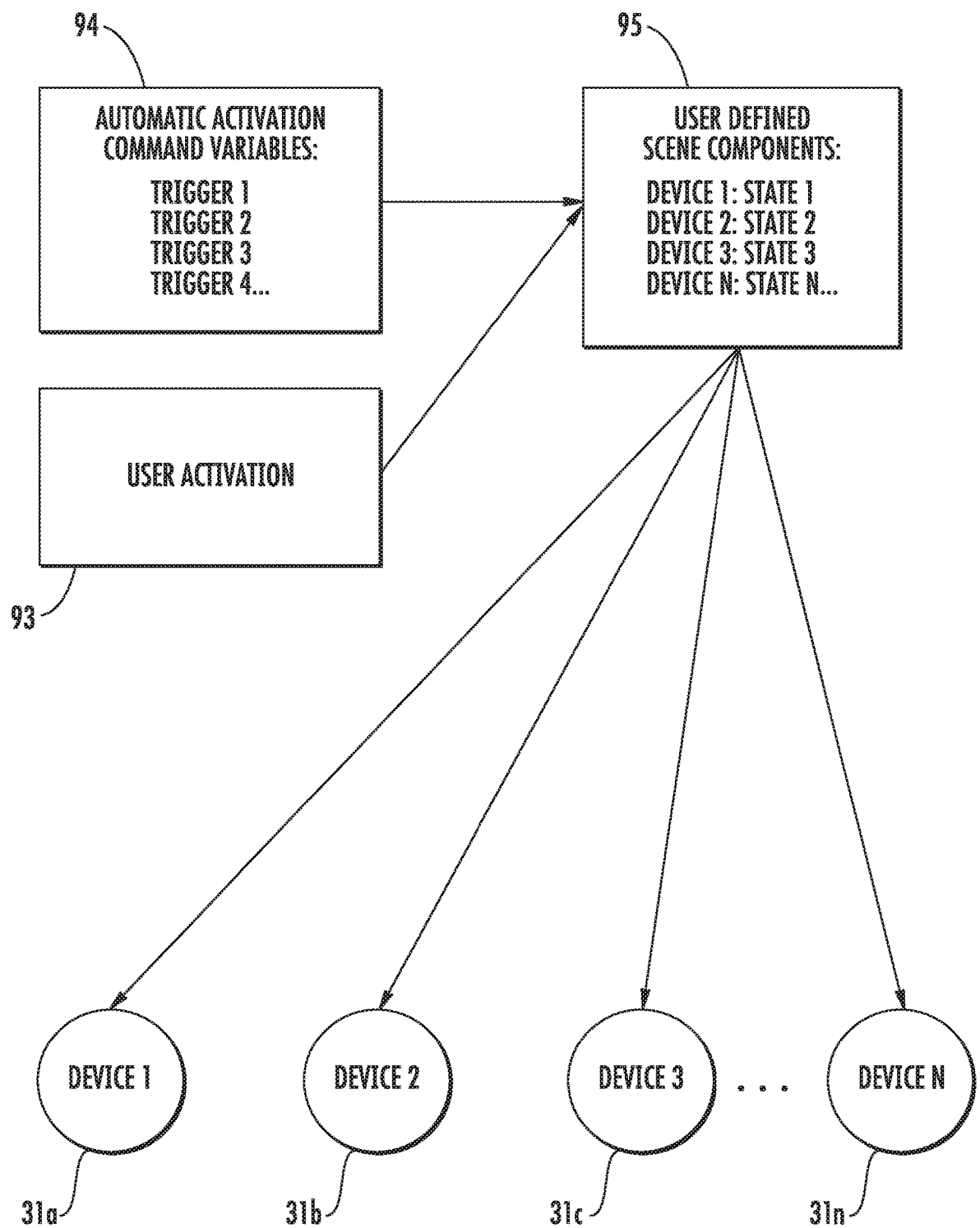
Figure 23:
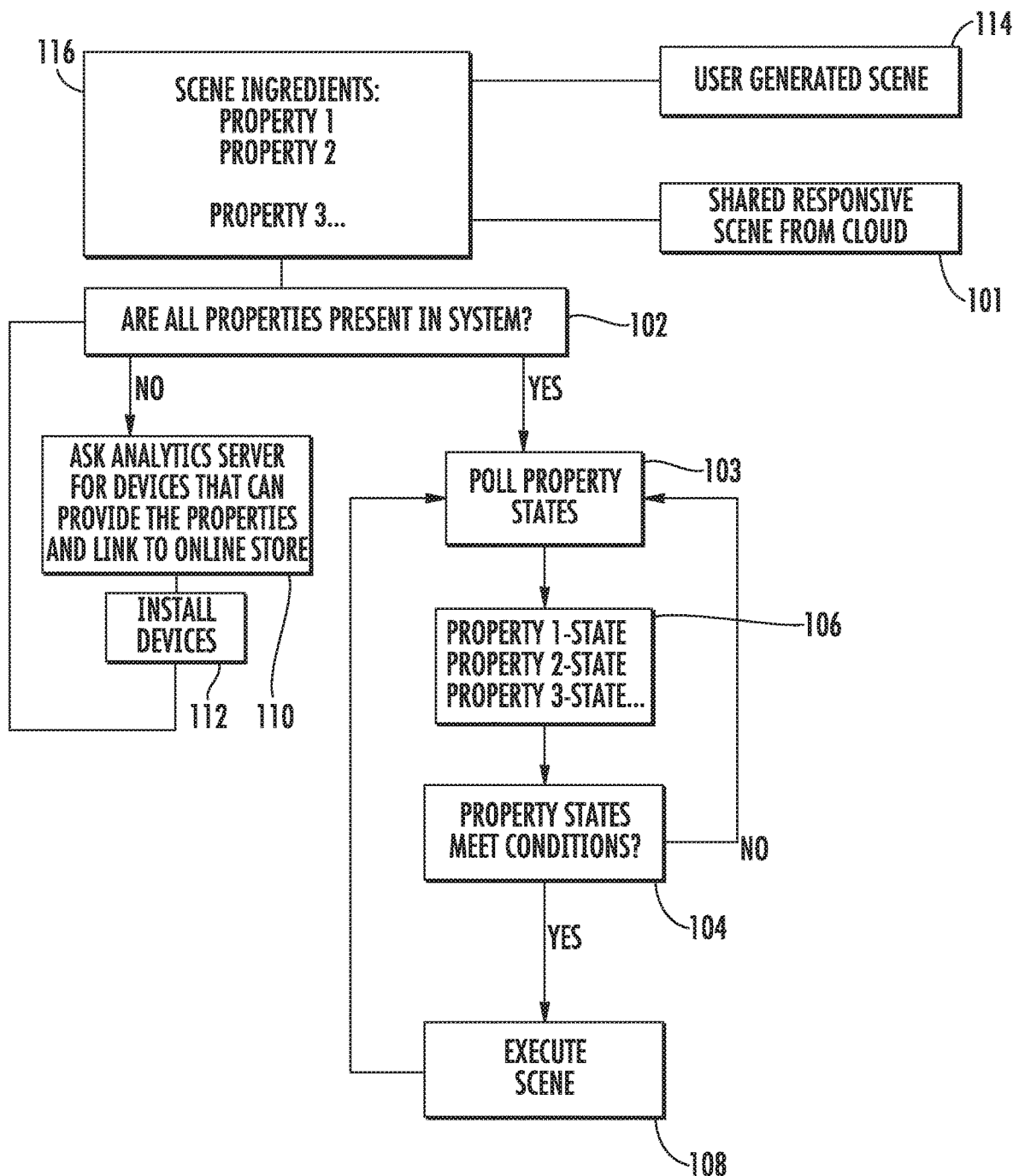

Referring now additionally to FIG. 22, the K4Home software, which may be executed on the home device 32 or the hub device 34, also features responsive scenes that function as a list of elements 95 of the K4Connect system 20 that then may induce actions in the addressable devices 31a-31n connected to the system 20. The responsive scenes can also return plain language notifications to the user, for example, at the user interface 35, based on the status of the system 20.

The standard responsive scenes can be set-up by the user by using a scene wizard. The scene wizard includes a list of addressable devices 31a-31n and command event variables or triggers 94. The user, for example via the user interface 35 of the K4App, selects the triggers for the scene, the addressable devices 31a-31n affected, and the actions or states the addressable devices will take to respond to the scene.

The standard responsive scene may be initiated by a list of triggers detected by the program or by the user activating the scene 93 in the user interface 35. An example of a command variable or trigger list is as follows: Trigger 1 is a time period, Trigger 2 is a mobile controlling device being connected to the network, Trigger 3 is a set day, and Trigger 4 is a connected motion detector sensing motion.

The scene has specified user defined components or which set of addressable devices 31a-31n will be contacted for the scene and what state those addressable devices should take. For example, controllable device 1 31a is a television (TV), addressable device 2 31b is a set of lights in the TV room, addressable device 3 31c is a room thermostat in the TV room, and addressable device n 31n controls operation of a coffee maker. The system 20 generates a command that is sent to the addressable device. The addressable devices 31a-31n respond based upon the command.

For example, Trigger 1 is activated from 7-9 pm, Trigger 2 is activated when a given user's smartphone or remote device 36 is connected to the local network, Trigger 3 is activated on weekdays, and Trigger 4 is activated by a living room motion detector detecting motion. Based upon the triggers, the user defined components turn the TV on to a given channel, dim the lights in the TV room, adjust the thermostat to 72 degrees, and begin brewing the evening decaf coffee.

The standard responsive scenes may also be shared between users using the cloud device 33 or K4Away, and a marketplace that lists available scenes. The K4Connect system 20 may also suggest possible other and/or additional addressable devices 31a-31n to connect to add functionality and more responsive scenes to individual users of K4Home.

Once a user has completed the responsive scene wizard or has added a shared responsive scene, the remote device 36 via the user interface 35 may display a modeled animation of the scene which shows what the scene looks like upon activation. The user may also access an animation of the scene that will function throughout the entire day and their triggers.

Referring now to FIGS. 23-29a, another aspect of K4Home is what may be referred to as an ingredient responsive scene based on property based ingredients, which allows the use of different addressable devices that can produce the same properties in the recipes. Instead of a scene being tied to a specific addressable device 31a-31n for a given function, for example, the scenes are based upon a specific property. This advantageously allows for responsive scenes to be implemented using the same elements that the responsive scene needs, but does not use identical devices.

For example, if a given user wants to know when another user is home, they may set up a responsive scene that identifies the addressable devices 31a-31n that may be used to indicate whether or not someone is home. For the given user, the addressable device 31a-31n or ingredient in the responsive scene may be a deactivated alarm system, which when tripped gives the desired properties to trigger the responsive scene. The responsive scene then has the K4Connect system 20 send the given user a notification, for example, a plain language notification, that the other user is home. This scene can then be shared with yet a third user who not does not have an alarm system but does have motion detectors 101, which fall in the same list of devices that can give the desired properties to complete the recipe. In other words, the scene is associated with a desired outcome irrespective of specific addressable devices 31a-31n. In instances where a recipe is almost completed or can be augmented by adding more controllable devices, the K4Connect system 20 informs the user, for example, via the user interface 35 on the remote device 36, of the possible recipe based responsive scene and links them to an online market where the user can download, either free or for purchase, the addressable device 31a-31n.

Another example of a responsive scene based on the ingredients list is if the system 20 indicates that a recipe has not been met, it can then send a plain language notification that the recipe has not been met. For example, if a person has not arrived at home by a certain time, the recipe includes the ingredients of presence (by way of motion detectors, cameras, and a connected smartphone (i.e., remote device 36)) and time. The lack of presence at a specific time triggers the scene and alerts the user. Of course, others, for example, a monitoring center and/or other designees, may be alerted.

Figure 24:
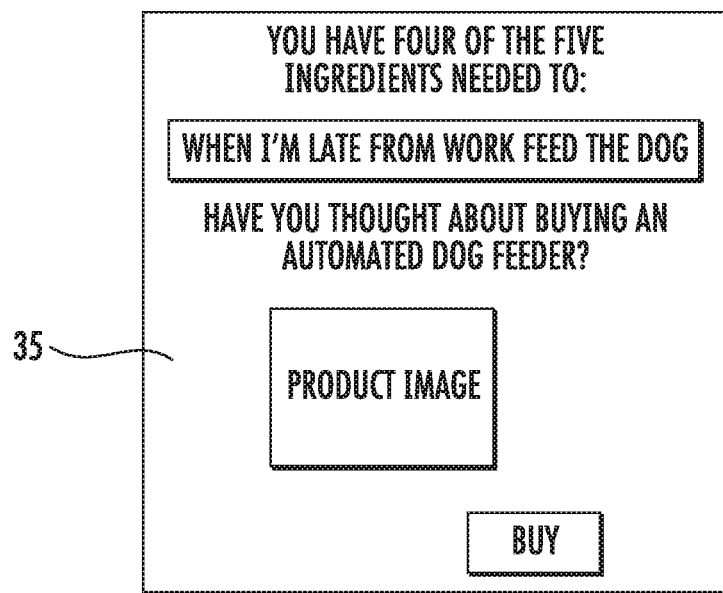
Figure 27:
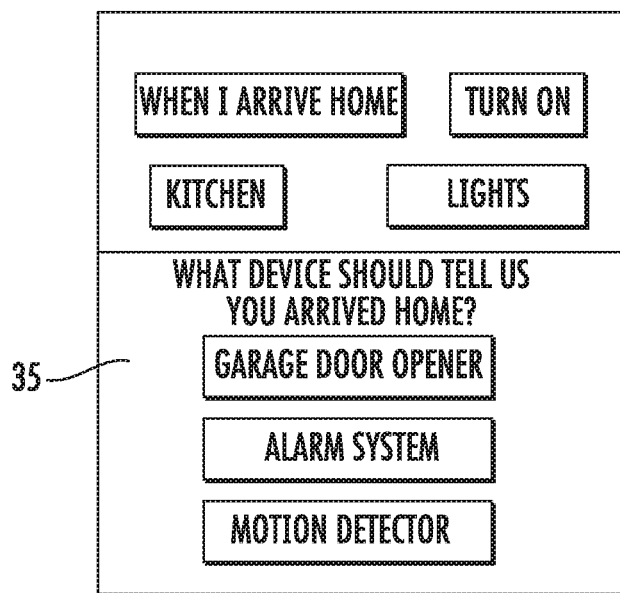
Figure 28:
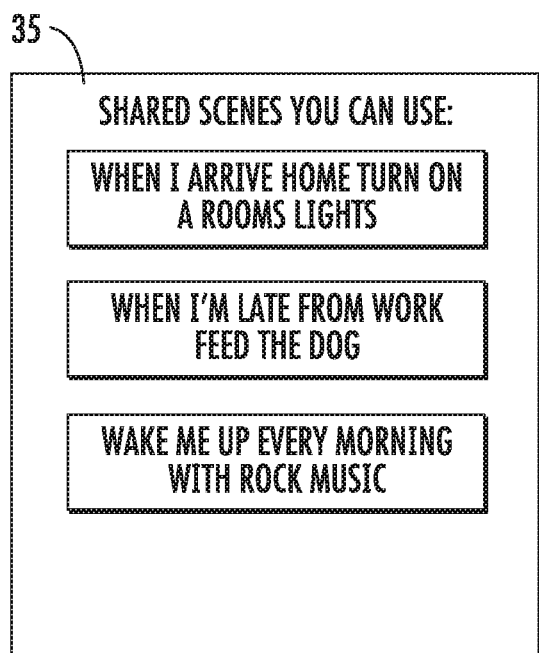

A user may set up an ingredient responsive scene (Block 114) or download a shared responsive scene (Block 101) from the cloud device 33. K4Home then determines whether all the ingredients (Block 116) are present in the K4Connect system 20 (Block 102). If addressable devices 31a-31n that can provide ingredients properties are connected the K4Connect system 20, the system determines the state (Block 106) of the addressable devices by polling the addressable devices (Block 103). If all of the ingredients of the scene are met (Block 104), then the K4Connect system 20 executes the scene (Block 108). If the ingredients of the K4Connect system 20 do not meet the conditions (Block 104), then the system may either poll the property states again (Block 103) or wait a specified amount of time set by K4Home or the responsive scene. If any of the ingredients/properties are not available in the K4Connect system 20 because an addressable device 31a-31n that can provide the ingredient is not connected, then K4Home sends a message to the analytics server 54 requesting suggested controllable devices from the cloud device 33 (Block 110) and may also cooperate to present the user, for example, on the user interface 35, an opportunity to purchase the suggested controllable devices (FIG. 24). The new addressable devices may be installed at Block 112.

In another example, a user may download a responsive scene that utilizes a camera to record motion events during a specific time period. For example, a given user wishes to record when his dog climbs onto the living room couch while the given user is at work from 8 am-5 pm. The given user then constructs the scene with three ingredients: ability to record video (provided by a camera connected to K4Home), motion (provided by the same camera's built in motion detector), and a time period. The given user then shares this on the responsive scene market place on the K4Away or cloud device 33. Another user downloads the scene and intends to use the scene for home security at night, for example. The other user has a camera, but not the ability to sense motion. K4Home suggests the other user install independent motion sensors to be able to use the scene and provides a link to the K4Store or the cloud device 33 from which the orders of any of a number of brands and styles of motion detectors may be purchased. The other user then installs the motion sensors, which now enables the responsive scene to be enacted since all ingredients are met. The other user then records any motion in his living room from 10 pm-6 am using the same base responsive scene while using different devices to provide the ingredients.

For example, a user may generate a responsive scene to provide the idea of "home." The responsive scene may be generated with respect to the user so that, "when I am home, I want light in the living room." The K4Connect system 20 indicates or displays, for example, via a menu, that "there are x devices you can use to determine whether I am home, and here are the devices that provide light." In other words, the scene is constructed first and then the addressable devices 31a-31n that can make the scene are provided.

Figure 29A:
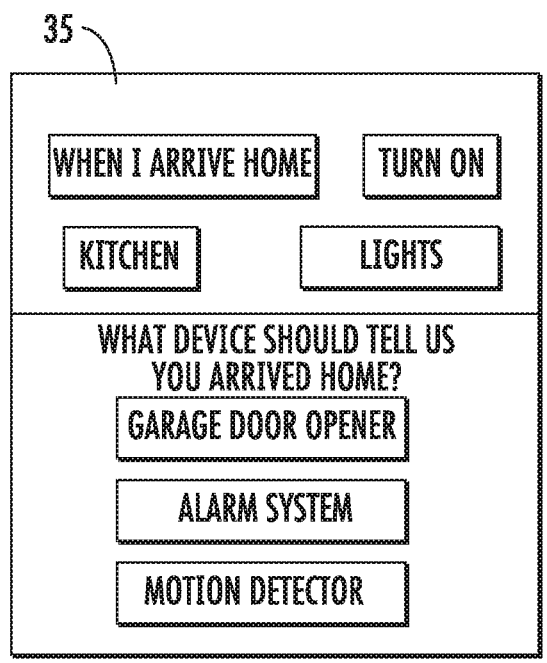
Figure 29B:
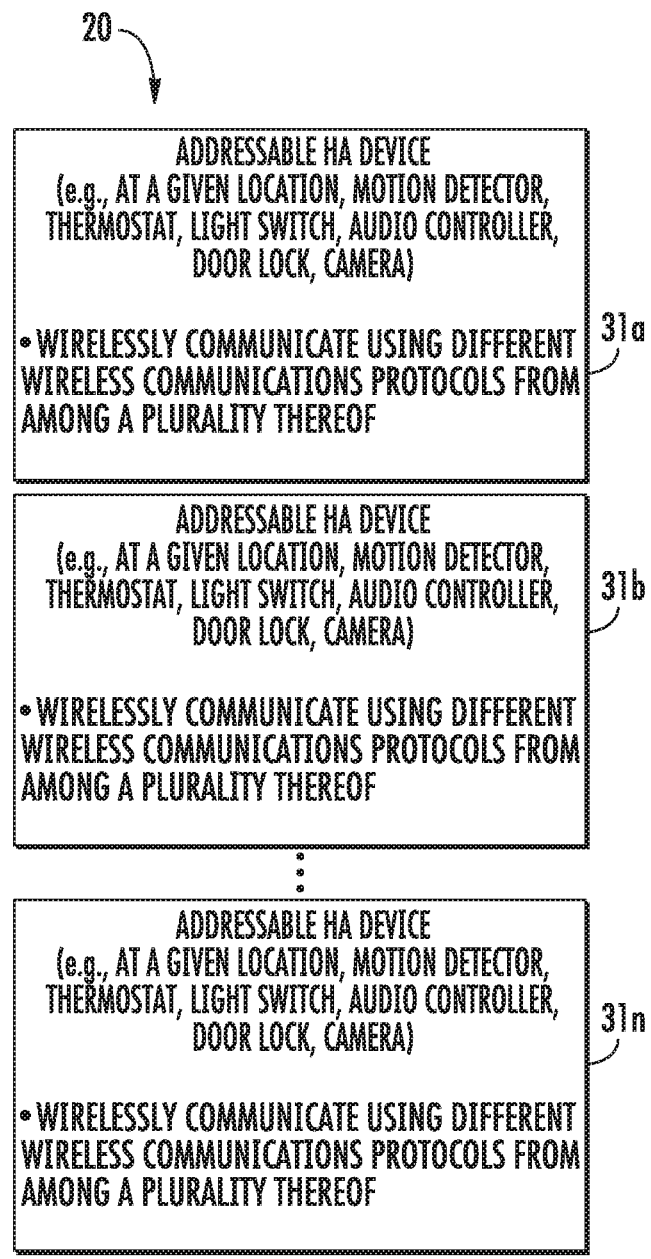
Figure 29B:
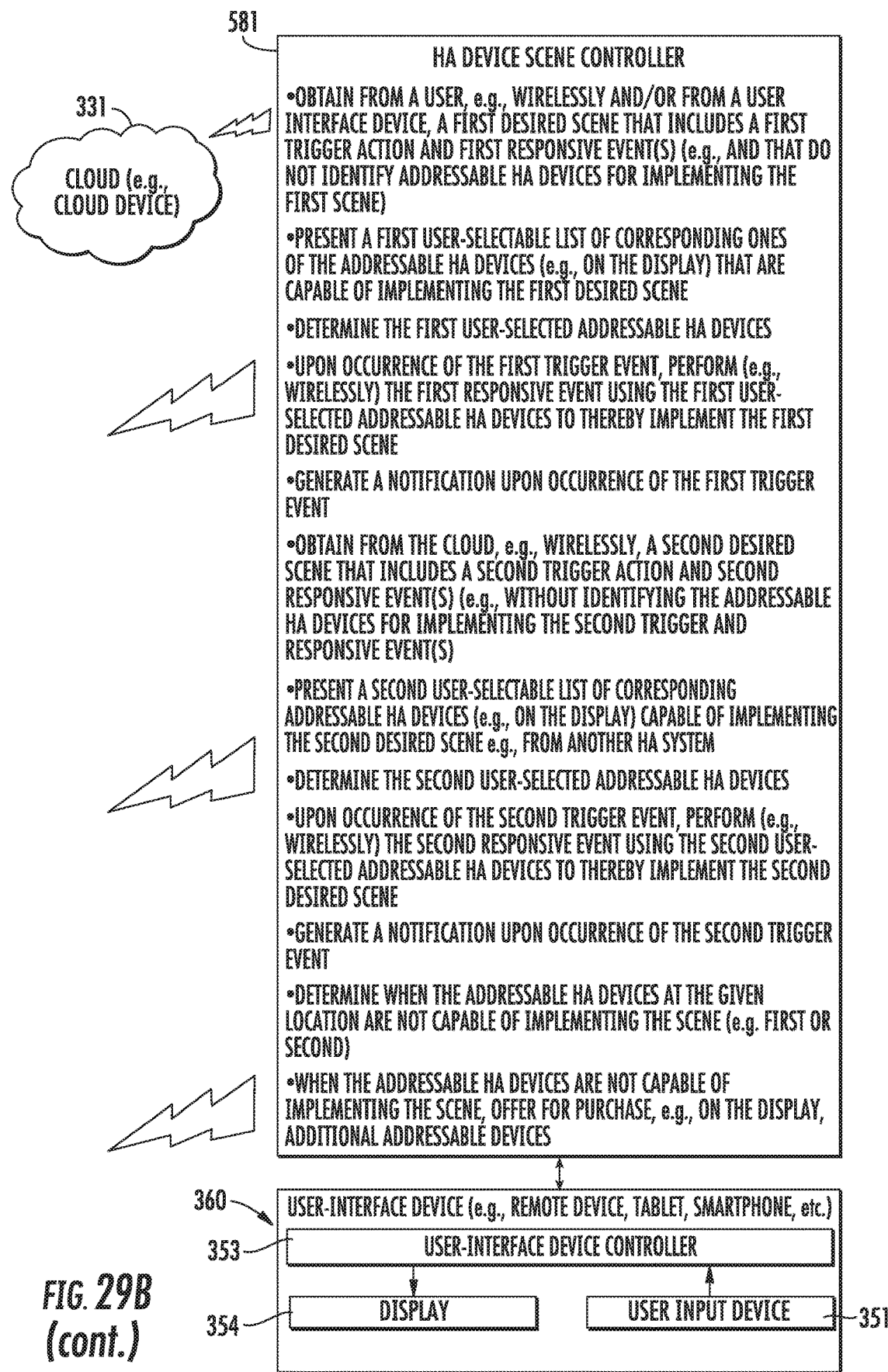

Referring now to FIG. 29b, ingredient responsive scenes as they relate to the HA system 20 will now be described. The HA system 20 includes addressable HA devices 31a-31n at a given location. The addressable HA devices 31a-31n include any of motion detectors, thermostats, light switches, audio controllers, door locks, and/or cameras. Of course, the addressable HA devices 31a-31n may include additional and/or other devices.

The HA system 20 also includes an HA device scene controller 581 that obtains from a user, for example, wirelessly, a first desired scene that includes a first trigger action and first responsive event. For example, the first trigger may be "when I arrive home" and the first responsive event may be "turn on the living room lights". Indeed, the first trigger action and the first responsive event do not identify which of the addressable HA devices 31a-31n are responsible for implementing the first trigger action and the first responsive events. The HA device scene controller 581 may obtain the first trigger action and the first responsive event from a user-interface device 360, for example, and more particularly, a user-input device 351 coupled to a user-interface controller 353 to permit user input. The user interface device 360 may be a remote device, for example, a tablet computer, a smartphone, etc. There may be more than one first trigger action and any number of first responsive events.

The HA device scene controller 581 also presents a first user-selectable list of corresponding ones of the addressable HA devices 31a-31n, for example, on a display 354 of the user-interface device 360 coupled to the user-interface controller 353, that are capable of implementing the first desired scene. In other words, the HA device scene controller 581 presents addressable HA devices 31a-31n that correspond to or will execute the first trigger action and the first responsive event.

The HA device scene controller 581 also determines the first user-selected ones of the addressable HA devices 31a-31n, and upon occurrence of the first trigger event, performs the first responsive event using the first user-selected addressable HA devices to thereby implement the first desired scene. The first desired scene may be executed wirelessly, for example, the HA device scene controller 581 may communicate wirelessly with the addressable HA devices 31a-31n to implement the first desired scene. In some embodiments, the HA device scene controller 581 may generate a notification upon occurrence of the trigger event.

The HA device scene controller 581 also obtains from the cloud 331, for example, wirelessly, a second desired scene that includes a second trigger action and second responsive event. The second trigger action and second responsive event are obtained without identifying the addressable HA devices 31a-31n responsible for implementing the second trigger action and second responsive event.

The HA device scene controller 581 may present a second user-selectable list of corresponding addressable HA devices 31a-31n, for example, on the display 354, capable of implementing the second desired scene. In other words, the second scene is obtained as a shared scene, for example from another person's HA system. The HA device scene controller 581 also determines the second user-selected addressable HA devices 31a-31n, and, similar to that described above, for example, wirelessly, upon occurrence of the second trigger event, performs the second responsive event using the second user-selected addressable HA devices to thereby implement the second desired scene.

The HA device scene controller 581 also may determine when the addressable HA devices 31a-31n at the given location are not capable of implementing the scene. When this is the case, the HA device scene controller 581 presents a purchase offer, for example on the display 354 for an additional addressable HA device. The user may purchase the additional addressable HA device by clicking on a hyperlink, for example.

A method aspect is directed to a method of implementing first and second desired scenes in an HA system 20. The method includes using an HA device scene controller 581 to obtain from a user the first desired scene that includes a first trigger action and a first responsive event and to present a first user-selectable list of corresponding addressable HA devices 31a-31n capable of implementing the first desired scene. The HA device scene controller 581 is also used to determine the first user-selected addressable HA devices 31a-31n, and upon occurrence of the first trigger event, perform the first responsive event using the first user-selected addressable HA devices to thereby implement the first desired scene.

The HA device scene controller 581 is also used to obtain from the cloud 331 the second desired scene that includes a second trigger action and a second responsive event and to present a second user-selectable list of corresponding addressable HA devices 31a-31n capable of implementing the second desired scene. The device scene controller 581 is also used to determine the second user-selected ones of the addressable HA devices, and upon occurrence of the at least one second trigger event, perform the second responsive event using the second user-selected addressable HA devices 31a-31n to thereby implement the second desired scene. In some embodiments, the HA device scene controller 581 is used to determine when the addressable HA devices 31a-31n at the given location are not capable of implementing the scene, and to present a purchase offer for an additional addressable HA device.

Development kits as they relate to the K4Connect system 20 will now be described. The K4Connect system 20 provides both software and hardware development kits. The software development kit builds a complete device stack for developers to interact with and handles all communication with the message queue. A built-in bridge editor allows developers to create and edit bridges from a web browser, for example, and a description editor creates device description XML files.

The hardware development kit allows developers to connect controllable devices directly to the message queue without an intermediary bridge. For example, as developers add communication protocols to their controllable devices, the K4Connect system 20, particularly the communication components thereof, may be integrated into their hardware to bypass a bridge on the system and communicate directly with the message queue.

Further details of the cloud device 33 or K4Away will now be described. In addition to the functions of K4Away already described, K4Away hosts an external API, which provides an interface for devices that cannot connect to Internet based services on their own. When connected to the K4Connect system 20 and K4Away, previously un-networked devices may become accessible to outside services such as, for example, IFTTT, Evernote, and Facebook, through its connection with K4Away.

With respect to security, the security model of the K4Connect system 20 is based upon providing a relatively high level of security for the system. Each phone or remote device 36 is authenticated on two levels. The first level is a device specific allowance added by the system administrator. The second level is the user login on the remote device 36. This two-layer system reduces occurrences of a login of unauthorized devices even if there is a valid user login.

The K4Connect system 20 also provides security through its privacy method in its analytics data collection. The data is stored on two separate servers. One server holds a token representing the anonymous user while the other server holds the usage and analytic data. The connection between the two servers occurs when authorized by the user for technical help. When the user is sent responsive scene or device recommendations, the suggestions are typically only sent to the token representing the user. The user remains anonymous at all times. In other words, a portion of the information about a user may be selectively available for providing technical support, similar to a "need-to-know" basis.

The K4Connect system 20 also uses a security method that grants the user complete rights and ownership to the data collected. The K4Connect system 20 collects and analyzes data from the user and stores it on the separate secure servers. After a threshold time period, for example, one year, the data is permanently deleted. This method includes a user override granting the user the ability to permanently delete their data at anytime.

The K4Hub 34 can also be used as a Wifi router connected to a home router so that all the devices connected to the K4Connect system 20 are routed through the private Wifi network of the K4Hub 34. This advantageously allows for a separation between devices, such as personal computers, connected to the K4Connect system. This separation may reduce the chances of attacks on personal computers from affecting the network among devices of the K4Connect system 20.

Figure 30A:
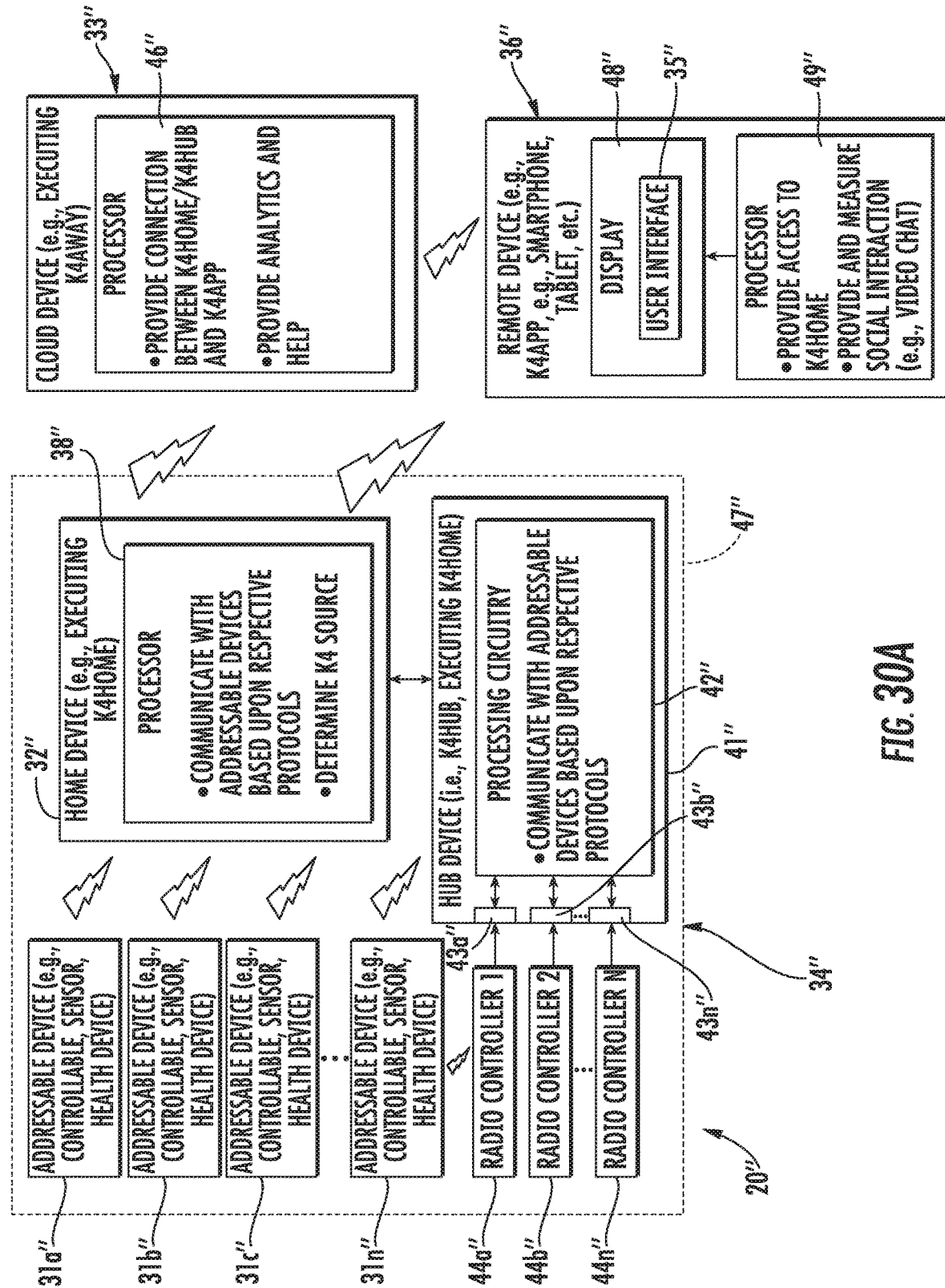
FIG. 30a is a block diagram of an electronic device integration system in accordance with another embodiment of the present invention.

Referring now to FIG. 30a, another aspect is directed to health related devices for use on the K4Connect system 20". The use of health related devices in conjunction with the K4Connect system 20" may be termed K4Life. However, it should be noted that other and/or additional devices, whether health related or not, may be part of the K4Life system. Similar to the K4Connect system described above, the K4Life system 20" includes addressable devices 31a"-31n", some of which may be in the form of health devices that measure human health related data, such as, for example, steps walked, blood pressure, weight, and other metrics. In other words, the K4Life system 20" performs the functions of the K4Connect system described above, and includes further health related functions as will be described in further detail below. For example, health devices may include one or more bed sensors, motion detectors, fitness tracking devices, blood pressure cuffs/monitors, weight scales, and temperature probes, for example. Of course, other and/or additional health devices or sensors, for example from the K4Home system, may be used.

In addition, the K4App provides social interaction, for example, photo sharing and live video chat. More particularly, when a live video chat is started, the K4Life system 20" may report the start time and duration of the live video chat to a central server, for example, the cloud device 33" or local server device.

The K4Life system 20", for example, the analytics server 54", computes a score indicating the overall health of the user, which may be referred as K4Score. The K4Score is determined by combining directly measured health data, activity level measured from the use of addressable devices or health devices 31a"-31n", and social engagement measured by the use of the K4App. The K4Score may include or be based upon other and/or additional information. The historical trend of this score may be used to predict improvement or decline in a user's health, for example. Of course, this data may be used for other purposes, for example, communicated to other users such as health care professionals, monitoring stations, etc. For example, a person who is sedentary, has irregular sleep patterns, and little social interaction may be identified as a having potential health issues. One example scenario where the K4Life system 20" and K4Score may be relatively advantageous is the use of the system by an elderly parent whose children wish to check on the parent's wellbeing or if a user simply wants to keep apprised of their own wellbeing.

In some embodiments, the health or activity data may be viewed by family members or in a group living setting, such as an assisted living facility or by an onsite or remote supervisor. The health data may also be displayed, for example, via the user interface 35" of the remote device 36", to show the health score of an individual user, or an aggregate of a community of users.

Figure 30B:
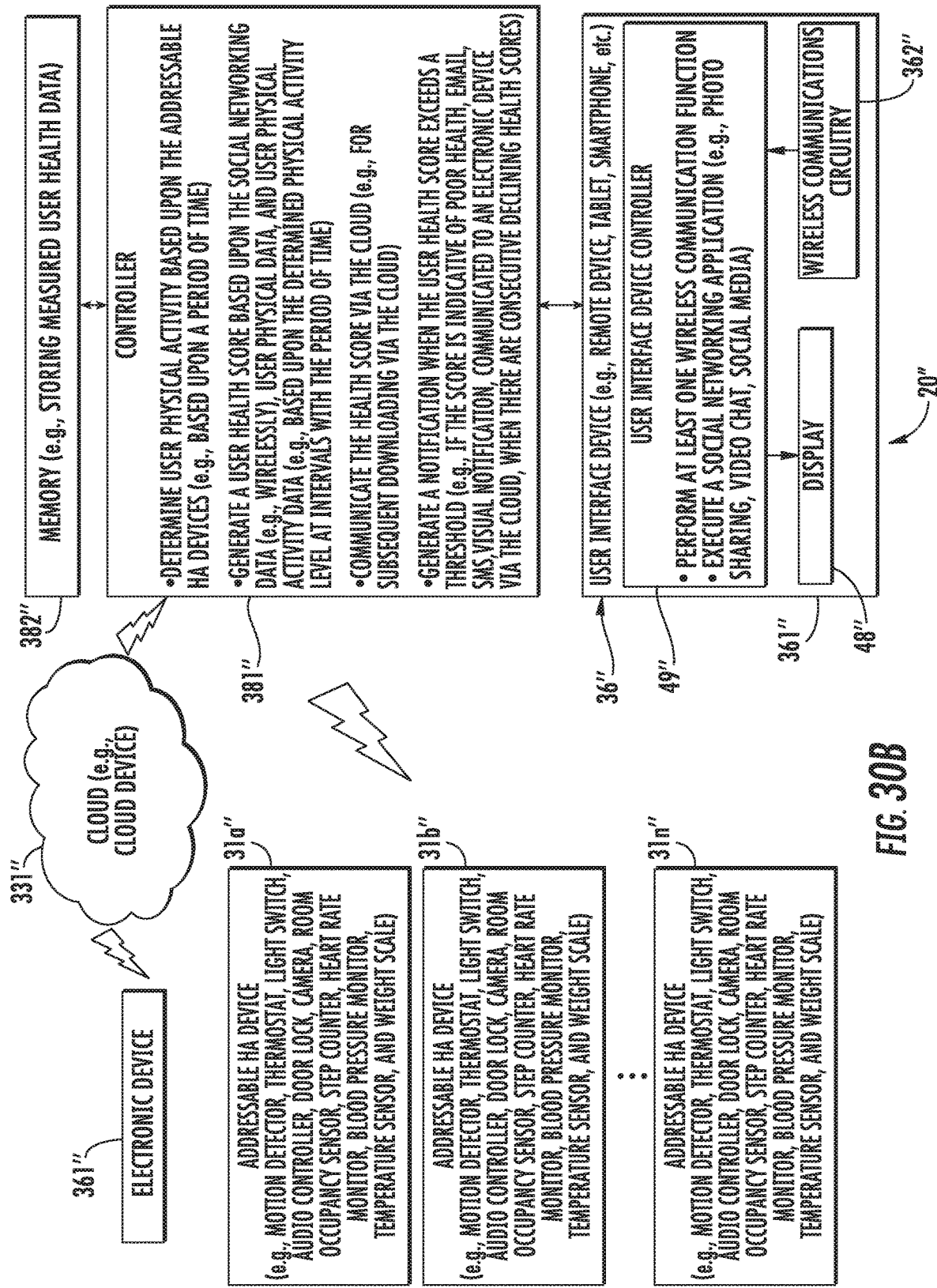
FIG. 30b is a schematic diagram of an HA system for generating a user health score in accordance with an embodiment.

Referring now to FIG. 30b, the health related aspects of the K4Connect or HA system 20" will now be described. The HA system 20" includes addressable HA devices 31a"-31n". The addressable HA devices 31a"-31n" may include any of motion detectors, thermostats, light switches, audio controllers, door locks, cameras, and/or health-related sensors (e.g. room occupancy sensors, bed sensors, step counters, heart rate monitors, blood pressure monitors, temperature sensors, and weight scales). Of course, the addressable HA devices 31a"-31n" may include other and/or additional devices. The addressable devices 31a"-31n" wirelessly communicate using respective different wireless communications protocols from among of different wireless communications protocols.

The HA system 20" also includes a user interface device 36" that permits user social networking and generates user social networking data based thereon, for example, data related to which social networking applications and an amount of time spent using each social networking application. The user interface device 36" includes a portable housing 361", a display 48" carried by portable housing, wireless communications circuitry 362" carried by the portable housing, and a user interface device controller 49" coupled to the display and wireless communications circuitry for performing at least one wireless communications function. For example, the user interface device 36" may be a smartphone or tablet, and may execute any number of social networking applications, for example, photo sharing, live video chat, and social media applications.

The HA system 20" also includes a controller 381" and a memory 382" coupled thereto that stores measured user health data and determines user physical activity data based upon the addressable HA devices 31a"-31n". The physical activity may be determined based upon a period of time period.

The controller 381" also generates a user health score based upon the user social networking data, user health data, and user physical activity data, and communicates the user health score via the cloud 331". The controller 381" may also generate user health scores based upon the determined physical activity level at intervals within the period of time, for example.

The controller 381" may, for example, generate a notification when the user health score exceeds a threshold. More particularly, if a user health score is indicative of poor health, a notification, such as, for example, an email, SMS message, visual notification on a display, etc. may be generated and communicated to an electronic device 361" via the cloud 331". In some embodiments, the controller 381" may generate a notification if there are consecutive declining user health scores over the time period. Once the user health score is communicated to the cloud 331", it may be downloaded, for example, by the electronic device 361" for storing, viewing, analysis, and/or other data processing as will be appreciated by those skilled in the art.

A method aspect is directed to a method of communicating a user health score in the HA system 20". The method includes permitting, via a user interface device 36", user social networking and generating user social networking data based thereon. The method also includes using the controller 361" and the memory 362" coupled thereto to store measured user health data, determine user physical activity data based upon the plurality of addressable HA devices, generate a user health score based upon the user social networking data, user health data, and user physical activity data, and communicate the user health score via the cloud.

Figure 31:
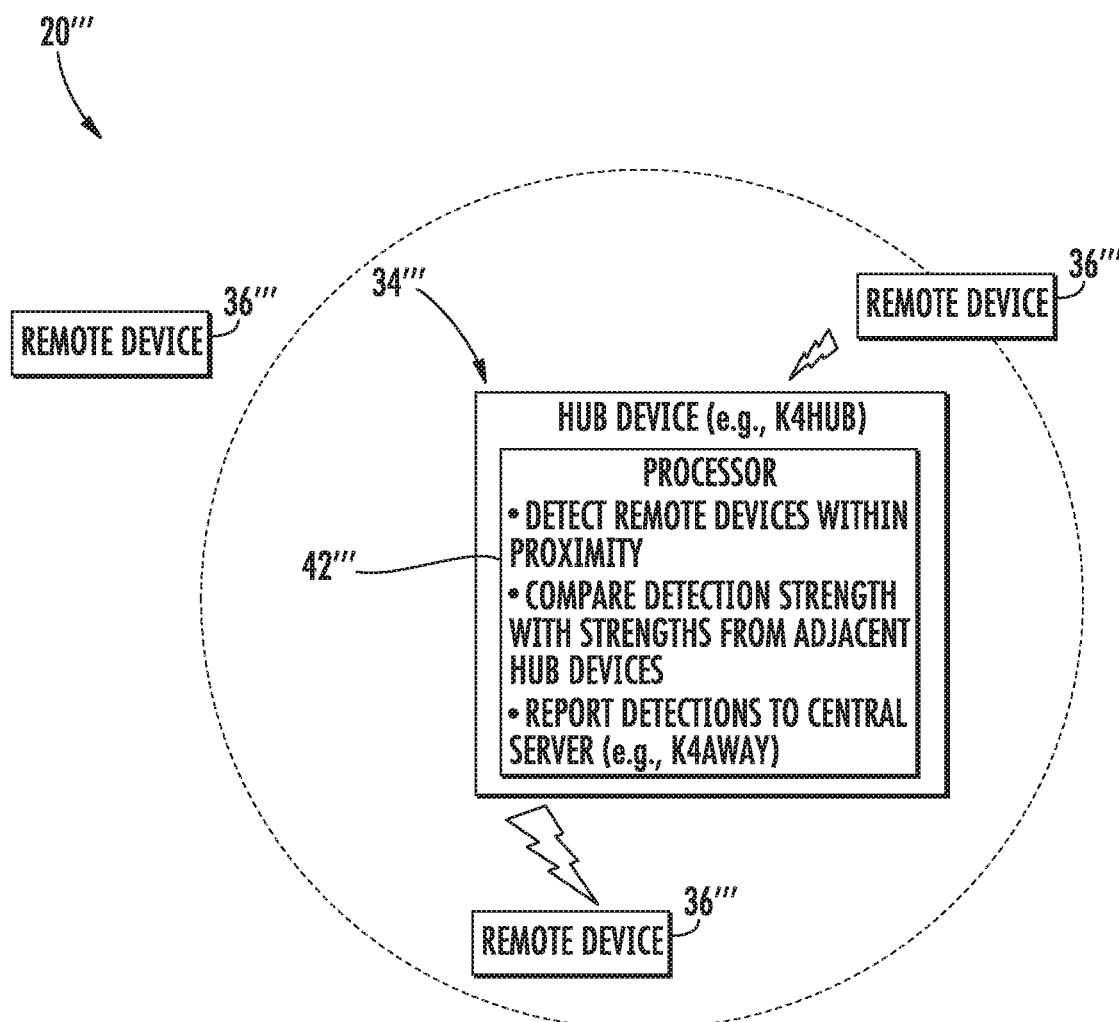
FIG. 31 is a diagram of a hub device for detecting proximity to a remote device in accordance with an embodiment of the present invention.

Referring now to FIG. 31, the K4Connect system 20''' may also be used for location determination. The K4Connect system 20''' may detect mobile devices (i.e., remote devices 36''') that are within a specified range of the K4Hub 34'''. These detections can be reported to a central server, for example, the cloud device or K4Away where they are used to estimate a person or device's location within a home or facility, for example. As more than one K4Hub 34''' can detect a mobile or remote device 36''' at a time, the K4Connect system 20''' reduces duplicate data by comparing the detection strength of overlapping data and determining which K4Hub was closest to the detected person or device. Of course, K4Connect system 20''' described in this embodiment may be particularly useful for use with the K4Life system described above.

Figure 32:
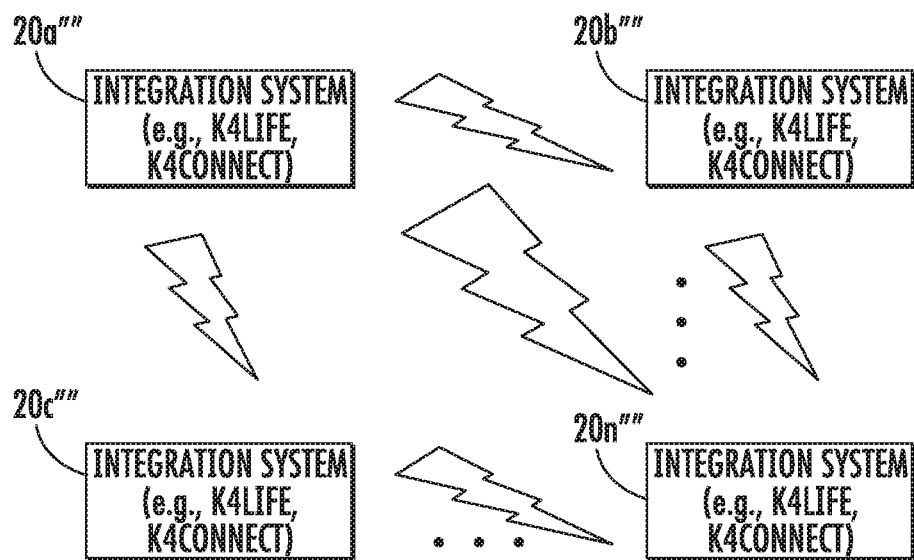
FIG. 32 is a schematic diagram of multiple electronic device integration systems in accordance with an embodiment of the present invention.

Referring now to FIG. 32, in another embodiment, multiple K4Life (or K4Connect) systems 20a''''-20n'''' may be used collectively in a system that may be referred to as K4Community. The K4Community system advantageously allows the aggregate data from the multiple K4Life or K4Connect systems 20a'''-20n'''', for example, at the cloud device or K4Away, to be analyzed for comparison within the community. Data from other controllers and/or devices may also be aggregated. Of course, any or each system 20a''''-20n'''' may process or aggregate the data, for example, entirely or in a shared or load balanced arrangement. Additionally, users in the K4Community 20a""-20n"" may be able to communicate with each other, and in some embodiments, see how others are performing relative to a given user's performance. As will be appreciated by those skilled in the art, because health related data is being collected and potentially exchanged, the health related data is maintained anonymous, and may be encrypted, until the user or owner of the health data agrees to share or actually shares it.

In some embodiments, the K4Life or K4Community system may not be limited to health related devices and health related data. For example, the principles of the systems described above may be applied to utility management, for example, apartment utility load control management. In such an embodiment, the sensors or controllable devices may be used to monitor energy and water usage, for example, and build a profile based thereon. Particular tenants that use more utilities relative to other tenants may be identified. Common areas may also be monitored and scored. A score may also be assigned to each tenant.

Figure 33:
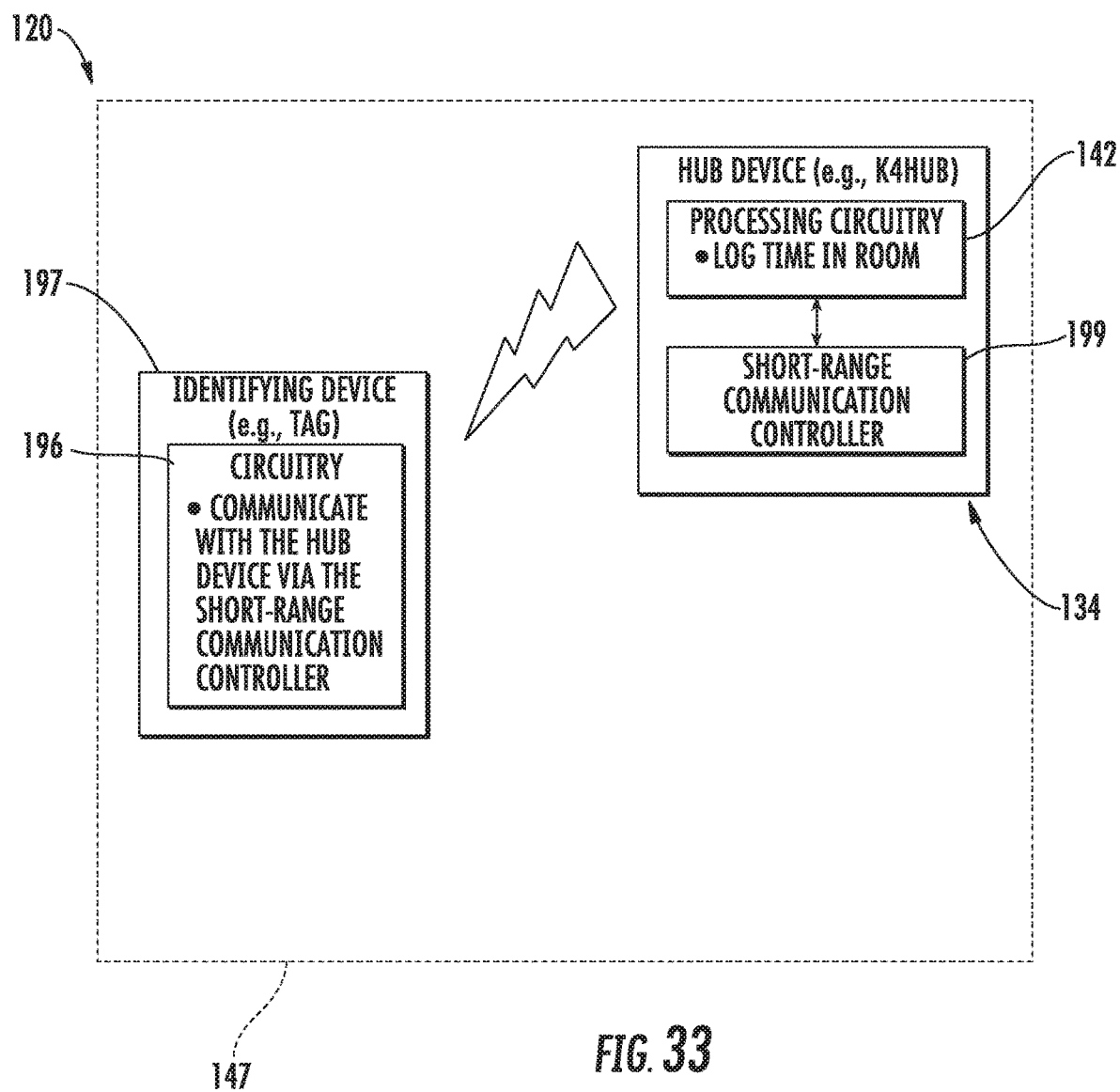
FIG. 33 is a schematic diagram of an electronic device integration system including a short-range communication protocol ID device in accordance with an embodiment of the present invention.

Referring to FIG. 33, in another embodiment the K4Life system 120 may be used in a health care setting to determine how much time a health care professional is giving a patient or user. In one particular example, the system 120 may be used in a nursing home to monitor how much time a nurse is spending with the user/patient, and when and if the nurse was in the room 147 with the patient. The system 120 and particularly, the hub device 134, includes a short-range communication protocol controller 199, such as, for example, Bluetooth, coupled to the processing circuitry 142. Of course, the hub device 134 may be used interchangeably in this or other embodiments with the home device. Each nurse would also wear an identifying device or tag 197 that includes circuitry 196 configured to communicate with the system via the short-range communication protocol. When the nurse is in the room with the user or patient and is within communication range, the system and tag communicate and the time and duration of communication is logged. This information can be used in a K4Community environment, as will be appreciated by those skilled in the art.

Figure 34:
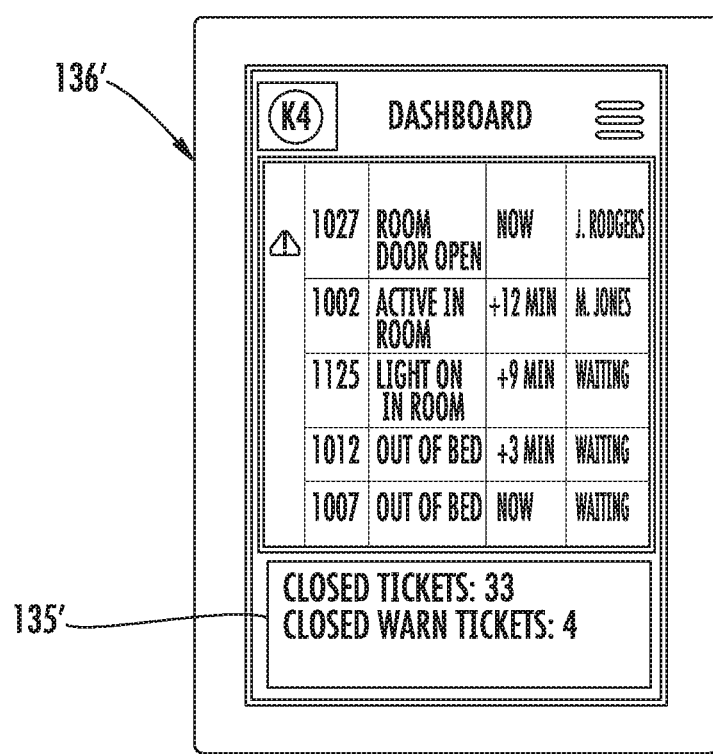
FIG. 34 is a diagram of a user interface illustrating event generation on a remote device for multiple electronic device integration systems in accordance with an embodiment of the present invention.

Referring now to FIG. 34, in another embodiment, for example, in a K4Community system such as a healthcare facility, events or tickets that are based upon addressable devices may be generated. Those events may be logged and/or assigned to staff and displayed on a user interface 135' of a remote device 136'. When the staff arrives at the room, for example, of the person associated with the event generation, that staff person's time of arrival may be logged, for example, as described above.

While several embodiments have been described as including software that is executed by a processor or processing circuitry of an electronic device, it should be understood by those skilled in the art, that software may include firmware, machine code, or a configuration of the processors or processing circuitry. Moreover, while several embodiments have been described, it will be appreciated that the functions described in any given embodiment may be used with other and/or additional functions, for example, as described in different embodiments. Still further, while the term "home" has been used to describe certain devices and/or locations (e.g. with respect to home automation), it will be appreciated by those skilled in the art, that the system and its components may be used in other locations, such as apartments, health centers, etc. Thus the term "home" is not specifically limited to a user's home. Moreover, while a processor and/or controller have been described herein, it will be appreciated that a processor and/or controller may include circuitry for execution respective functions and may also include a memory. A memory may also be coupled to the processor and/or controller, for example.

Method aspects include making a home automation integration system as described in any of the embodiments described herein, including K4Connect, K4Life, and K4Community, for example. Other method aspects include operation of the system or the various components thereof as well as performing any of the functions detailed above, for example, integration, communication, display, etc.

Another aspect is directed to a non-transitory computer readable medium that stores instructions for executing any of the functions of the systems and methods described herein. For example, the functionality of the K4App, K4Home, and K4Away may be embodied as computer executable instructions stored on a non-transitory computer readable medium. Of course other functions described herein may be embodied on a non-transitory computer readable medium.

Figure 35:
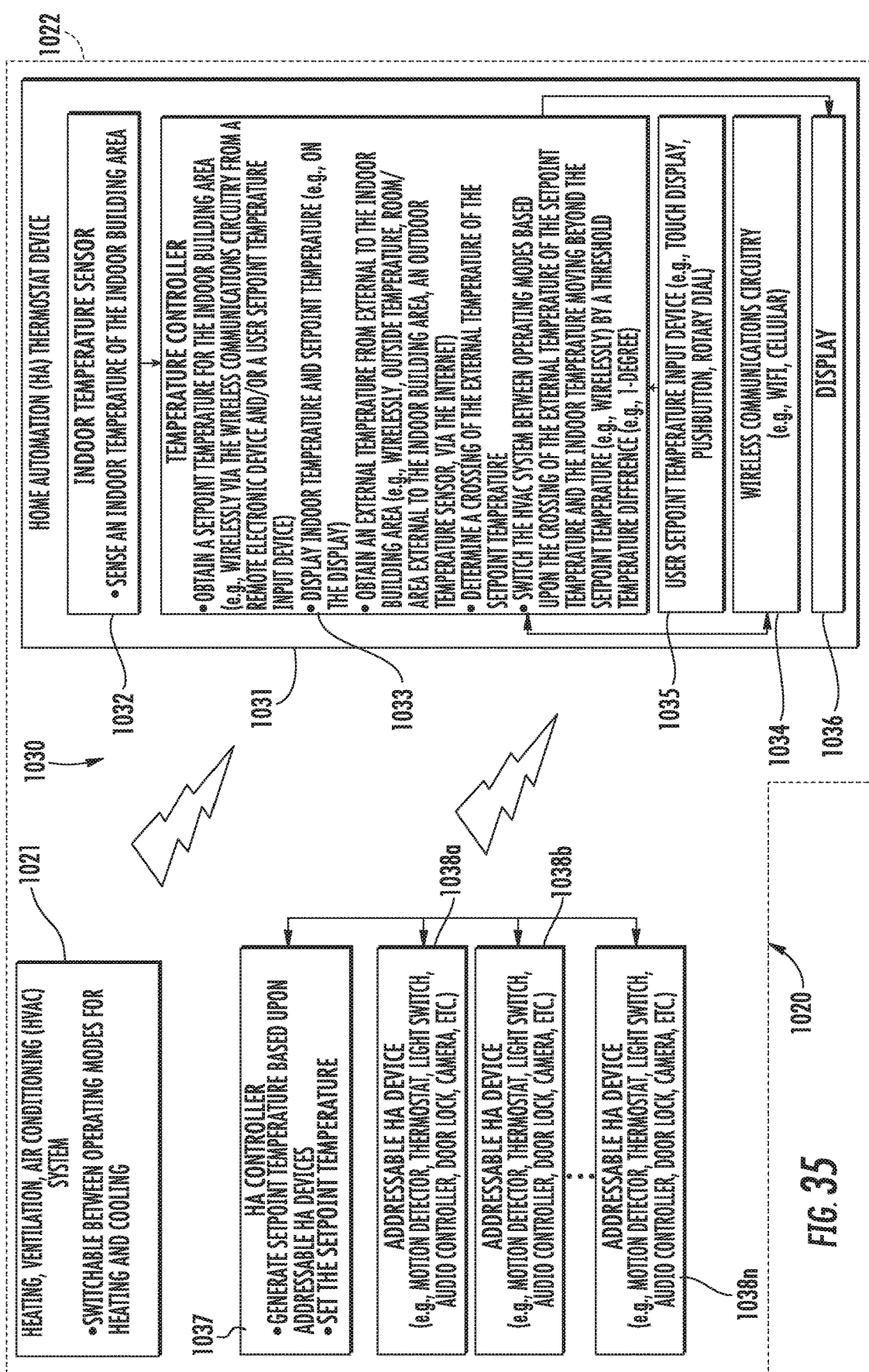
FIG. 35 is a schematic diagram of a climate control system in accordance with an embodiment.

Referring now to FIG. 35, another embodiment is directed to a climate control system 1020 that includes a heating, ventilation, and air conditioning (HVAC) system 1021 for an indoor building area 1022. The HVAC system 1021 is switchable between operating modes for heating and cooling. The climate control system 1020 includes a home automation (HA) thermostat device 1030 in the indoor building area 1022. The HA thermostat device 1030 includes a housing 1031 and an indoor temperature sensor 1032 carried by housing. The indoor temperature sensor 1032 senses an indoor temperature of the indoor building area 1022.

A temperature controller 1033 is carried by the housing 1031. The HA thermostat device 1030 also includes wireless communications circuitry 1034 coupled to the temperature controller 1033. The wireless communications circuitry 1034 may be configured to communicate via Wifi, cellular, or other protocol, for example.

The temperature controller 1033 obtains a setpoint temperature for the indoor building area 1022. The setpoint temperature may be obtained wirelessly, for example, via the wireless communications circuitry 1034. The setpoint temperature may be obtained from an input device, a remote electronic device, and/or other device, as will be appreciated by those skilled in the art.

The HA thermostat device 1030 also includes a user setpoint temperature input device 1035 and a display 1036, both carried by the housing 1031 and coupled to the temperature controller 1033. The user setpoint temperature input device 1035 may be in the form of a touch display, pushbutton, rotatable dial, or other input device, as will be appreciated by those skilled in the art. The user setpoint temperature input device 1035 may be used to set the setpoint temperature. The temperature controller 1033 may cooperate with the display 1036 to display the indoor temperature and the setpoint temperature.

The setpoint temperature may also be generated or set based upon an HA controller 1037, for example, as described above, and coupled to the HA thermostat device 1030 and configured to generate the setpoint temperature. As described above, the HA controller 1037 may be coupled to addressable HA devices 1038a-1038n, for example, motion detectors, lighting, etc. The HA controller 1037 generates the setpoint temperature based upon one of the addressable HA devices 1038a-1038n. For example, based upon motion detected from a motion detector, the HA controller 1037 may communicate with the HA thermostat device 1030 to set the setpoint temperature (i.e., set the setpoint temperature cooler when someone is home). Of course, the setpoint temperature can be set based upon other types of addressable HA devices 1038a-1038n.

The temperature controller 1033 also obtains an external temperature from external to the indoor building area 1022. The external temperature may be obtained wirelessly, for example, via the Internet. The external temperature may be an outside temperature or may be an inside temperature of a room or area that may be considered external to the indoor building area 1022, for example. In some embodiments, more than one temperature sensor (indoor and/or outdoor) may be used to obtain the external temperature.

The temperature controller 1033 determines a crossing of the external temperature of the setpoint temperature, and switches the HVAC system 1021 between operating modes based upon the crossing of the external temperature of the setpoint temperature and the indoor temperature moving beyond the setpoint temperature by a threshold temperature difference, for example, one degree. Other threshold temperature differences may be used.

Figure 36:
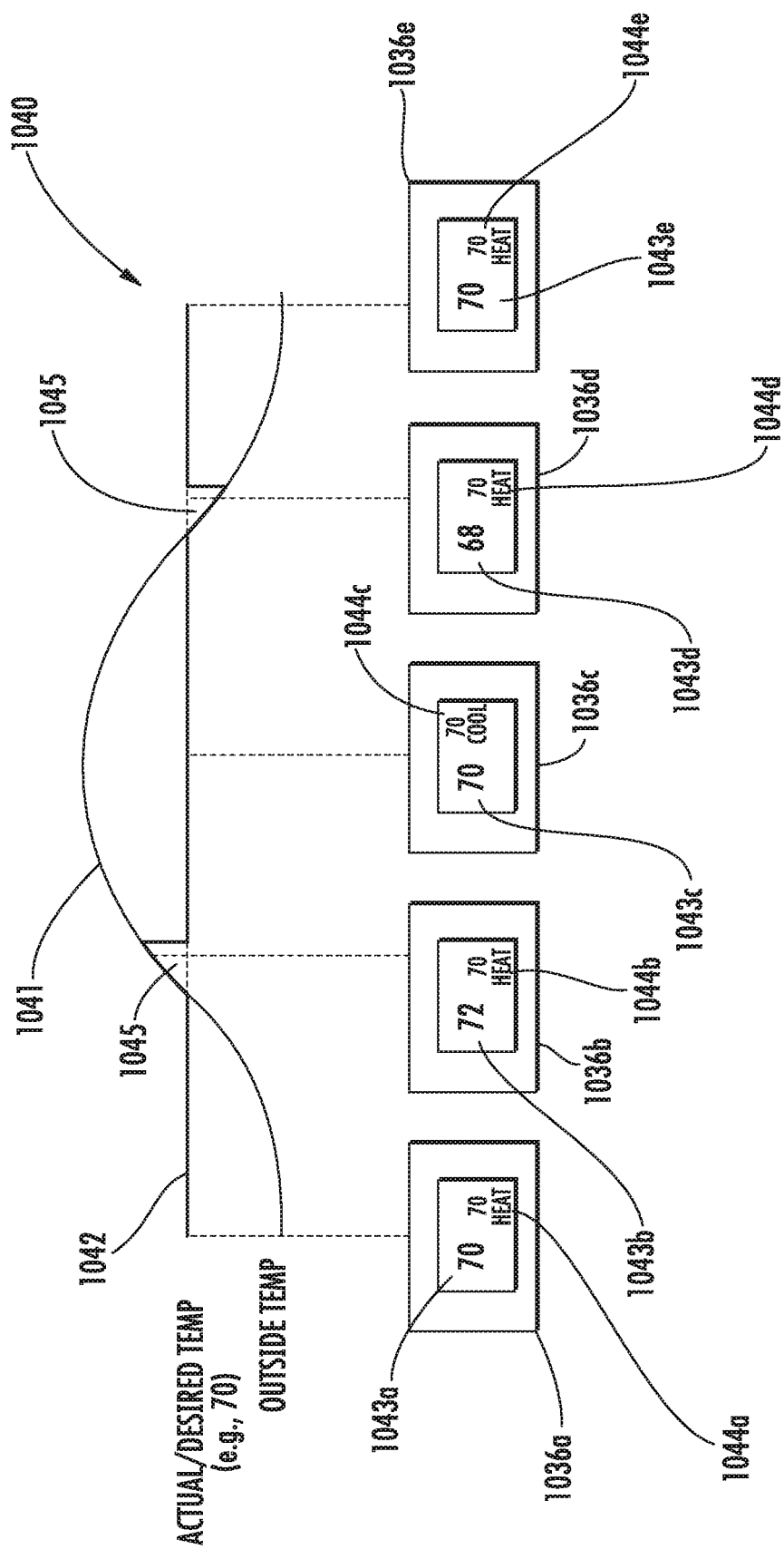
FIG. 36 is a graph illustrating operation of the climate control system of FIG. 35.

Referring now additionally FIG. 36, operation of the climate control system 1020 is illustrated by way of the graph 1040 and corresponding displays 1036a-1036e that show corresponding indoor temperatures 1043a-1043e and setpoint temperatures 1044a-1044e at different points in time identified on the graph. In the graph 1040, the outside temperature is shown by the line 1041, while the actual or indoor temperature is shown by the line 1042. Illustratively, the indoor temperature or room temperature deviates from desired temperature or setpoint temperature momentarily while the external temperature passes through the deadbands 1045.

A method aspect is directed to a method of operating the climate control system 1020. The method includes sensing the indoor temperature of the indoor building area 1022 via the indoor temperature sensor 1032. The method also includes using the HA thermostat device 1030 in the indoor building area 1022 to obtain a setpoint temperature for the indoor building area, obtain an external temperature from external to the indoor building area, determine a crossing of the external temperature of the setpoint temperature, and switch the HVAC system 1021 between operating modes based upon the crossing of the external temperature of the setpoint temperature and an indoor temperature of the indoor building area 1022 moving beyond the setpoint temperature by a threshold temperature difference.

Referring now to FIGS. 37a-37e, in another embodiment of an HA system 2020, it may be desirable to remotely access the addressable HA devices 2031a-2031n. Remote access of the addressable HA devices 2031a-2031n, also known as IOT devices, may be particularly helpful for troubleshooting an issue with a given addressable HA device and/or updating software or a configuration, for example.

The addressable HA devices 2031a-2031n are typically behind one or more a network address translation (NAT) routers and/or firewalls, and are thus not generally internet accessible, as will be appreciated by those skilled in the art. Accordingly, to access the addressable HA devices 2031a-2031n, on-demand secure shell (SSH) tunneling may be used.

On-demand SSH tunneling allows a given one of the addressable HA devices 2031a-2031n to communicate with, for example, through periodic connections, a known host to retrieve tunneling instructions. The tunneling instructions may thus permit remote access to a given addressable HA device with reduced overhead through the SSH protocol, for example. Of course, other protocols, for example, secure protocols, may be used.

Figure 37A:
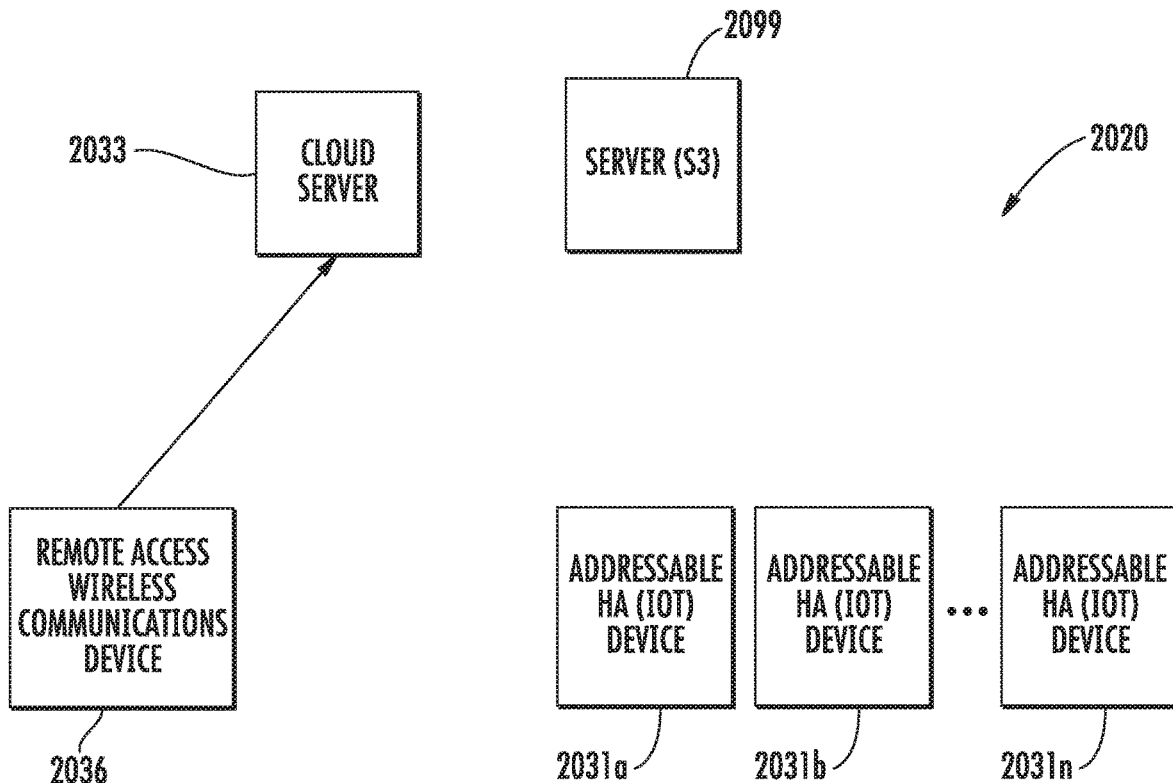
FIGS. 37a-37e are schematic block diagrams of an HA system illustrating communications between an addressable HA device and a remote access wireless communications device in accordance with an embodiment.

To establish a remote connection to an addressable HA or IOT device 2031a-2031n a request is issued for a given addressable HA device to open a tunnel. This may be performed using on-demand SSH tunneling by way of a remote user, for example, via remote access wireless communications device 2036, creating a file in a web-visible (e.g. publically accessible) location that is specific to the given addressable HA device (FIG. 37a). The web-visible location may be on a server 2099 or other web-visible location, for example. In an example embodiment, the file may be an Amazon simple storage service (S3) file that is a hash of the given addressable HA device's unique identification and the last unique cloud session identification. The S3 file may include other and/or additional information about the addressable HA device 2031a-2031n.

Figure 37B:
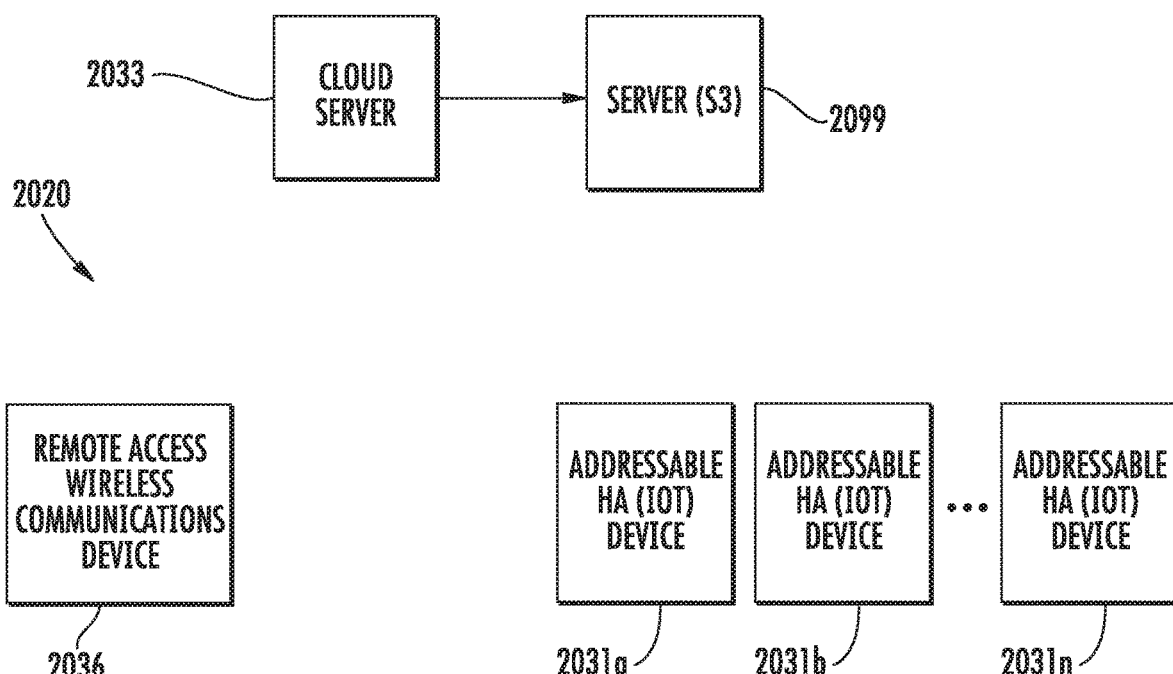

A cloud server 2033 may make available the device specific instructions for the given HA device 2031a-2031n in a known location, for example, on the server 2099 (FIG. 37b). In some embodiments, the device specific instructions may be collocated on the cloud server 2033.

Figure 37C:
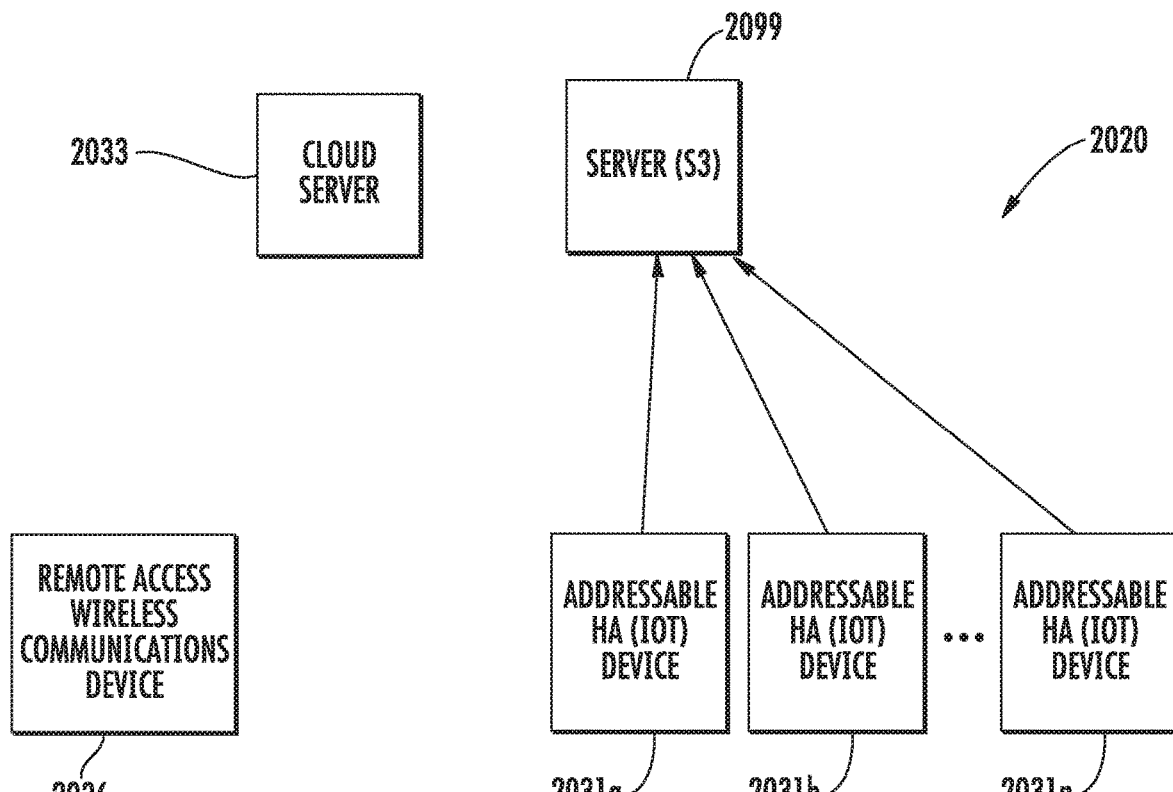

Addressable HA devices 2031a-2031n communicate with, for example, by periodically polling, this location. For example, the location may be polled every few minutes. Of course, the addressable HA devices 2031a-2031n may communicate with or poll the location at longer, shorter, and/or different intervals. Based upon the polling, for example, the addressable HA device 2031a-2031n finds the tunneling instructions stored and made available for the given addressable HA device (FIG. 37c). In one example, the instructions may be a json file that includes a cloud-visible host/port/ username/password. Of course, the instructions may be embodied in a different type of file and/or other data elements may be stored in the instruction file.

Figure 37D:
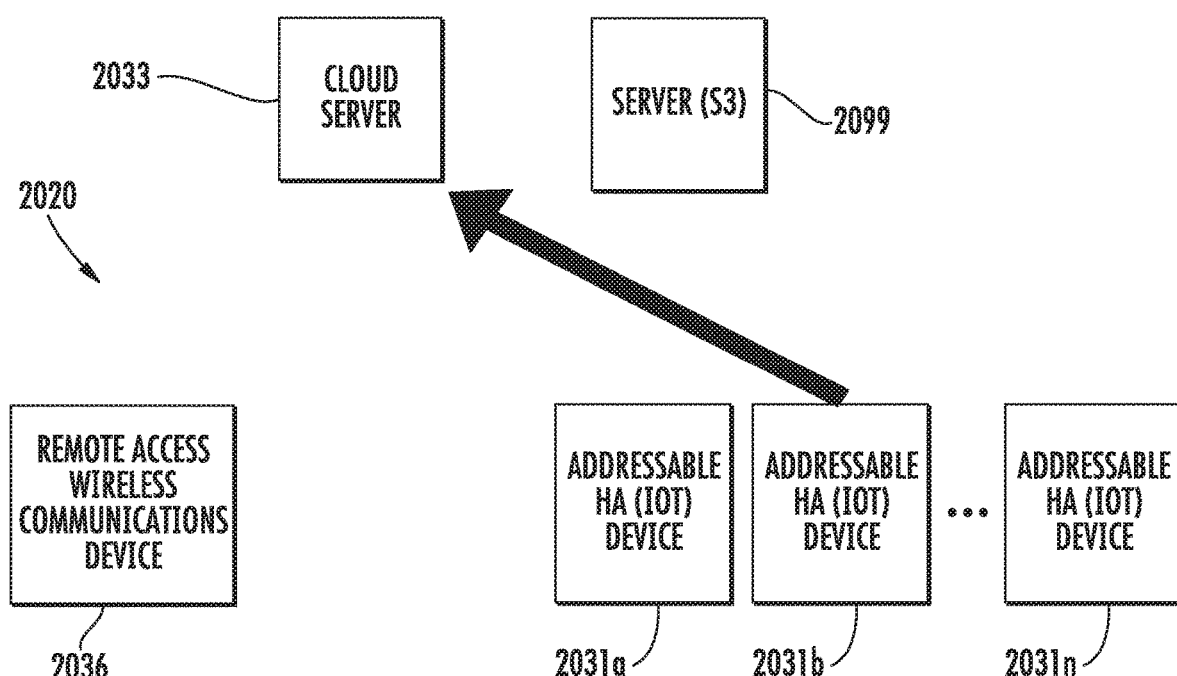
Figure 37E:
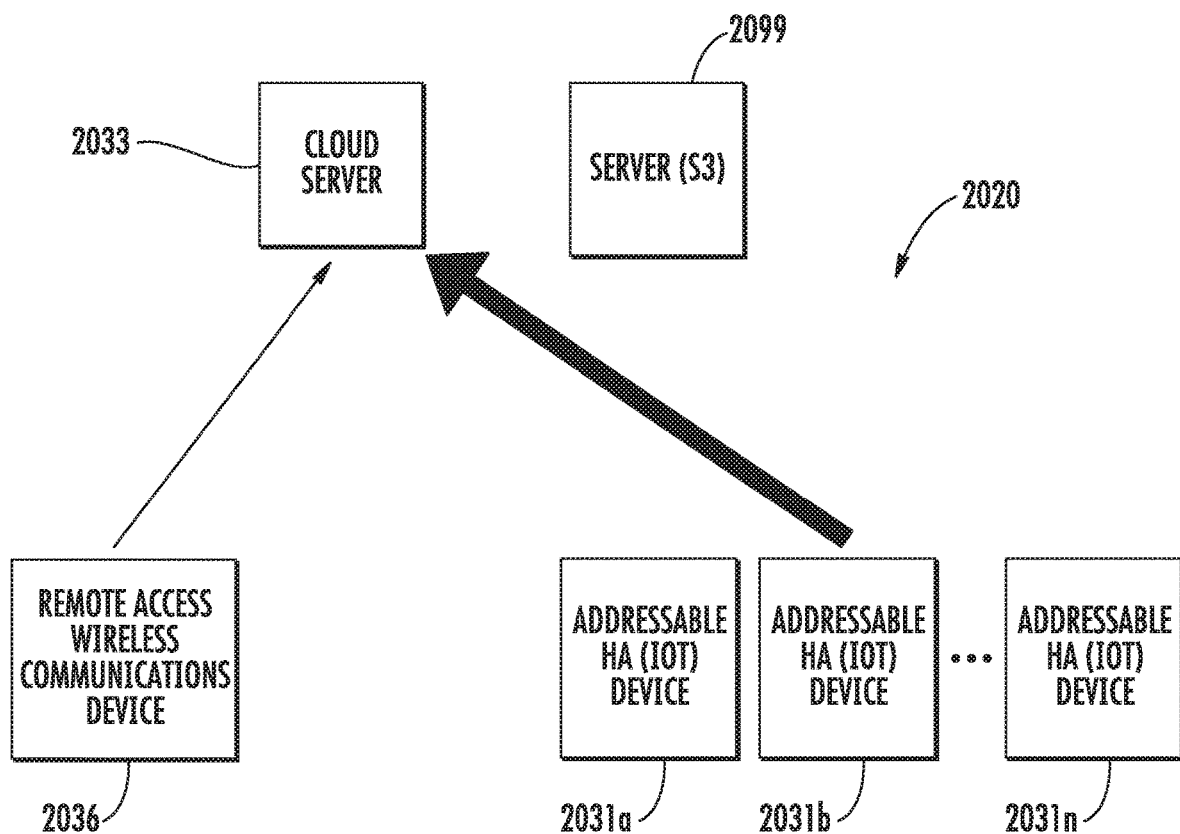

The given addressable HA device 2031a-2031n opens an SSH tunnel to the cloud server 2033 according to the instructions retrieved from the web-accessible location (FIG. 37d). The remote user via the remote access wireless communications device 2036, may then connect to the cloud-end of the tunnel permitting communication with, for example, by way of logging into, the given addressable HA device 2031a-2031n as though it were internet-visible (FIG. 37e).

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A home automation (HA) system comprising:
    a plurality of addressable HA devices within a community living facility, at least one of said plurality of addressable HA devices comprising at least one of a light switch and a thermostat within the community living facility, and the plurality of addressable HA devices communicating using a plurality of different wireless communications protocols;
    a user interface device configured to permit user social networking and generate user social networking data based thereon;
    an HA hub device within the community living facility and configured to provide communications for the plurality of addressable HA devices using respective different communications protocols from among the plurality of different wireless communications protocols; and a controller and a memory coupled thereto and configured to
store measured user health data for a plurality of users within the community living facility,
cooperate with said user interface device and said HA hub device to selectively communicate with said plurality of addressable HA devices for operation thereof,
determine user physical activity data for a given user within the community living facility over a period of time based upon the selective operation of said plurality of addressable HA devices, the physical activity data being indicative of a level of user activity measured from operation of the at least one of the light switch and the thermostat,
generate a plurality of user health indicators at intervals for the given user within the period of time, each based upon the user social networking data, user health data, and user physical activity data,
predict a decline in user health for the given user based upon declining user health indicators within the period of time,
determine aggregated health indicators for the plurality of users within the community living facility within the period of time,
communicate the user health indicator for the given user and the aggregated health indicators for the plurality of users within the community living facility to a remote device via the cloud, and
maintain anonymously the user health indicator for the given user and communicate the anonymous user health indicator for the given user and the aggregated health indicators for the plurality of users within the community living facility to a further user within the community living facility via a further user interface device associated with the further user.

2. The HA system of claim 1 wherein said user interface device is configured to generate the user social networking data based upon a time of social networking.

3. The HA system of claim 1 wherein said user interface device is configured to generate the user social networking data based upon a type of social networking activity of a plurality of different social networking activities performed via said user interface device.

4. The HA system of claim 3 wherein the type of social networking activity comprises at least one of photo sharing, live video chat, and operation of a social networking website.

5. The HA system of claim 1 wherein said user interface device comprises:
a portable housing;
a display carried by said portable housing;
wireless communications circuitry carried by said portable housing; and
a user interface device controller coupled to said display and said wireless communications circuitry and configured to perform at least one wireless communications function.

6. The HA system of claim 1 wherein each of said plurality of addressable HA devices comprises one of a room occupancy sensor, a bed sensor, a step counter, a heart rate monitor, a blood pressure monitor, a temperature sensor, and a weight scale.

7. A home automation (HA) system comprising:
a plurality of addressable HA devices within a community living facility, at least one of said plurality of addressable HA devices comprising at least one of a light switch and a thermostat within the community living facility, and the plurality of addressable HA devices communicating using a plurality of different wireless communications protocols;
an HA hub device within the community living facility and configured to provide communications for the plurality of addressable HA devices using respective different communications protocols from among the plurality of different wireless communications protocols;
a user interface device comprising
a portable housing,
a display carried by said portable housing,
wireless communications circuitry carried by said portable housing, and
a user interface device controller coupled to said display and said wireless communications circuitry and configured to
perform at least one wireless communications function, and
permit user social networking and generate user social networking data based thereon; and
a controller and a memory coupled thereto and configured to
store measured user health data for a plurality of users within the community living facility,
cooperate with said user interface device and said HA hub device to selectively communicate with said plurality of addressable HA devices for operation thereof,
determine user physical activity data for a given user within the community living facility over a period of time based upon the selective operation of said plurality of addressable HA devices, the physical activity data being indicative of a level of user activity measured from operation of the at least one of the light switch and the thermostat,
generate a plurality of user health indicators at intervals for the given user within the period of time, each based upon the user social networking data, user health data, and user physical activity data,
predict a decline in user health for the given user based upon declining user health indicators within the period of time,
determine aggregated health indicators for the plurality of users within the community living facility within the period of time,
communicate the user health indicator for the given user and the aggregated health indicators for the plurality of users within the community living facility to a remote device via the cloud,
maintain anonymously the user health indicator for the given user and communicate the anonymous user health indicator for the given user and the aggregated health indicators for the plurality of users within the community living facility to a further user within the community living facility via a further user interface device associated with the further user, and
generate a notification when the user health indicator exceeds a threshold.

8. The HA system of claim 7 wherein said user interface device is configured to generate the user social networking data based upon a time of social networking.

9. The HA system of claim 7 wherein said user interface device is configured to generate the user social networking data based upon a type of social networking activity of a plurality of different social networking activities performed via said user interface device.

10. The HA system of claim 9 wherein the type of social networking activity comprises at least one of photo sharing, live video chat, and operation of a social networking website.

11. A method of communicating a user health indicator in a home automation (HA) system comprising a plurality of addressable HA devices within a community facility, at least one of the plurality of addressable HA devices comprising at least one of a light switch and a thermostat within the community living facility, and the plurality of addressable HA devices communicating using a plurality of different wireless communications protocols, the method comprising:

permitting, via a user interface device, user social networking and generating user social networking data based thereon;

using an HA hub device within the community living facility to provide communications for the plurality of addressable HA devices using respective different communications protocols from among the plurality of different wireless communications protocols; and using a controller and a memory coupled thereto to
store measured user health data for a plurality of users within the community living facility,
cooperate with the user interface device and the HA hub device to selectively communicate with the plurality of addressable HA devices for operation thereof,
determine user physical activity data for a given user within the community living facility over a period of time based upon the selective operation of the plurality of addressable HA devices, the physical activity data being indicative of a level of user activity measured from operation of the at least one of the light switch and the thermostat,
generate the plurality of user health indicators at intervals for the given user within the period of time, each based upon the user social networking data, user health data, and user physical activity data,
predict a decline in user health for the given user based upon declining user health indicators within the period of time,
determine aggregated health indicators for the plurality of users within the community living facility within the period of time,
communicate the user health indicator for the given user and the aggregated health indicators for the plurality of users within the community living facility to a remote device via the cloud, and
maintain anonymously the user health indicator for the given user and communicate the anonymous user health indicator for the given user and the aggregated health indicators for the plurality of users within the community living facility to a further user within the community living facility via a further user interface device associated with the further user.

12. The method of claim 11 wherein generating the user social networking data comprises generating the user social networking data based upon a time of social networking.

13. The method of claim 11 wherein generating the user social networking data comprises generating the user social networking data based upon a type of social networking activity of a plurality of different social networking activities performed via the user interface device.

* * * * *